US010350287B2

(12) United States Patent
Audonnet et al.

(10) Patent No.: US 10,350,287 B2
(45) Date of Patent: Jul. 16, 2019

(54) HENDRA VIRUS RECOMBINANT COMPOSITIONS AND USES THEREOF

(71) Applicant: BOEHRINGER INGELHEIM ANIMAL HEALTH USA INC., Duluth, GA (US)

(72) Inventors: Jean-Christophe Audonnet, Lyons (FR); Jules Maarten Minke, Corbas (FR); Teshome Mebatsion, Watkinsville, GA (US); Catherine Charreyre, Lyons (FR)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 0 days.

(21) Appl. No.: 15/233,013

(22) Filed: Aug. 10, 2016

(65) Prior Publication Data

US 2017/0087242 A1    Mar. 30, 2017

Related U.S. Application Data

(62) Division of application No. 13/478,165, filed on May 23, 2012, now abandoned.

(60) Provisional application No. 61/491,037, filed on May 27, 2011.

(51) Int. Cl.
  *A61K 39/155*  (2006.01)
  *C07K 14/005*  (2006.01)
  *A61K 39/12*   (2006.01)
  *C12N 7/00*    (2006.01)
  *A61K 39/00*   (2006.01)

(52) U.S. Cl.
  CPC ............ *A61K 39/155* (2013.01); *A61K 39/12* (2013.01); *C07K 14/005* (2013.01); *C12N 7/00* (2013.01); *A61K 2039/505* (2013.01); *A61K 2039/5254* (2013.01); *A61K 2039/5256* (2013.01); *A61K 2039/53* (2013.01); *A61K 2039/545* (2013.01); *A61K 2039/70* (2013.01); *C12N 2710/24043* (2013.01); *C12N 2760/18222* (2013.01); *C12N 2760/18234* (2013.01); *C12N 2799/023* (2013.01)

(58) Field of Classification Search
  None
  See application file for complete search history.

(56) References Cited

U.S. PATENT DOCUMENTS

2007/0031455 A1    2/2007  Audonnet

FOREIGN PATENT DOCUMENTS

WO    WO2005/028673    3/2005
WO    WO2006/085979    8/2006

OTHER PUBLICATIONS

ATCC Converting TCID50 to MOI, accessed on Mar. 31, 2017 at «https://www.atcc.org/support/faqs/d3ce1/Converting%20TCID50%20to%20MOI-410.aspx».*
Gilbert et al., Current status for high titre poxvirus stock preparation in CEF under serum-free medium conditions: implication for vaccine development, 2005, Cytotechnology, vol. 48, pp. 79-88.*
Bossart et al., J Virol. 2002; 76:11186-98, "Membrane fusion tropism and heterotypic functional activities of the Nipah virus and Hendra virus envelope glycoproteins".
Bossart et al., J Virol. 2005; 79:6690-6702, "Receptor binding, fusion inhibition, and induction of cross-reactive neutralizing antibodies by a soluble G glycoprotein of Henda virus".
Chua et al., Lancet. 1999,354 (9186):1257-9, "Fatal encephalitis due to Nipah virus among pig-farmers in Malaysia".
Guillaume et al., Virology 2009; 387:459-465, "Acute Hendra virus infection: analysis of the pathogenesis and passive antibody protection in the hamster model".
Hooper PT, et al., Australian Vet J 1996; 74:244-5, "The retrospective diagnosis of a second outbreak of equine morbillibvirus infection".
Lam & Chua, Clin Infect Dis. May 1, 2002;34 Suppl 2:S48-51, "Nipah virus encephalitis outbreak in Malaysia".
Lee et al., Ann Neurol. Sep. 1999;46(3):428-32, "The neurological manifestations of Nipah virus encephalitis, a novel paramyxovirus".
McEachern et al., Vaccine 2008; 26:3842-3852, "A recombinant subunit vaccine formulation protects against lethal Nipah virus challenge in cats".
Paton et al., Lancet. Oct. 9, 1999;354(9186):1253-6, "Outbreak of Nipah-virus infection among abattoir workers in Singapore".
Rogers RJ, et al., Australia Vet J 1996; 74:243-4, "Investigation of a second focus of equine morbillivirus infection in costal Queensland".
Selvey LA, et al., Med J Australia 1995, 162:642-5, "Infection of humans and horses by a newly described morbillivirus".
Guillaume V et al., "Nipah Virus: Vaccination and passive protection studies in a hamster model", Journal of Virology, vol. 78, No. 2, P834-840.
Bossart et al., 2001, "Functional expression and membrane fusion tropism of the envelope glycoproteins of hendra virus", Virology 290, 121-135.
Gao et al. UpGene: Application of a Web-Based DNA Codon Optimization Algorithm, 2004, Biotechnology Progress, vol. 20, No. 2, pp. 443-448.
GenBank Accession # AF017149, Hendra Virus, complete genome, Apr. 1, 2003.

* cited by examiner (Continued)

Primary Examiner — Benjamin P Blumel
(74) Attorney, Agent, or Firm — Judy Jarecki-Black; Steffan Finnegan

(57) ABSTRACT

The present invention provides vectors that contain and express in vivo or in vitro one or more Hendra virus polypeptides or antigens that elicit an immune response in animal or human against Hendra virus and Nipah virus, compositions comprising said vectors and/or Hendra virus polypeptides, methods of vaccination against Hendra virus and Nipah virus, and kits for use with such methods and compositions.

11 Claims, 36 Drawing Sheets

Specification includes a Sequence Listing.

Figure 1

| SEQ ID NO | Type | Description |
|---|---|---|
| 1 | DNA | Wild-type DNA encoding Hendra virus G protein (AF017149.2) |
| 2 | DNA | Codon-optimized DNA encoding Hendra virus G protein |
| 3 | protein | Hendra virus G protein |
| 4 | DNA | Wild-type DNA encoding Hendra virus F protein (AF017149.2) |
| 5 | DNA | Codon-optimized DNA encoding Hendra virus F protein |
| 6 | protein | Hendra virus F protein |
| 7 | DNA | Part of p362-Hendra G plasmid sequence containing G gene and H6 promoter |
| 8 | DNA | Part of p362-Hendra G plasmid sequence containing G gene, H6 promoter and C5 arms |
| 9 | DNA | Entire p362-Hendra G plasmid sequence |
| 10 | DNA | Part of p362-Hendra F plasmid sequence containing F gene and H6 promoter |
| 11 | DNA | Part of p362-Hendra F plasmid sequence containing F gene, H6 promoter and C5 arms |
| 12 | DNA | Entire p362-Hendra F plasmid sequence |
| 13 | oligo | HenG.1F |
| 14 | oligo | HenG.1R |
| 15 | oligo | C5R.1F |
| 16 | oligo | C5L.2R |
| 17 | oligo | HenF.1F |
| 18 | oligo | HenF.1R |
| 19 | DNA | DNA encoding Nipah F protein |
| 20 | Protein | Nipah F protein |
| 21 | DNA | DNA encoding Nipah G protein |
| 22 | Protein | Nipah G protein |
| 23 | Protein | Hendra F protein Genbank accession No. AAB39505 |
| 24 | Protein | Hendra F protein Genbank accession No. AAV80428 |
| 25 | Protein | Hendra F protein Genbank accession No. NP_112026 |
| 26 | Protein | Hendra F protein Genbank accession No. AEQ38114 |
| 27 | Protein | Hendra F protein Genbank accession No. AEB21197 |
| 28 | Protein | Hendra G protein Genbank accession No. AAV80425 |
| 29 | Protein | Hendra G protein Genbank accession No. AEB21216 |
| 30 | Protein | Hendra G protein Genbank accession No. AEB21206 |
| 31 | Protein | Hendra G protein Genbank accession No. AAV80426 |
| 32 | Protein | Hendra G protein Genbank accession No. AEQ38108 |
| 33 | Protein | Hendra G protein Genbank accession No. AEQ38115 |

Figure 2
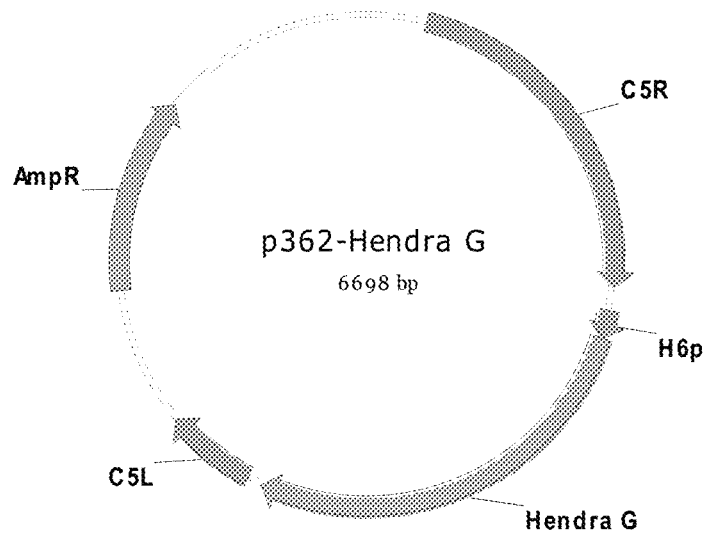
| | | | |
|---|---|---|---|
| C5R | Start: 248 End: 1783; | H6p | Start: 1881 End: 2004 |
| Hendra G | Start: 2005 End: 3816; | C5L | Start: 3880 End: 4284 |
| AmpR | Start: 4897 End: 5754 | | |
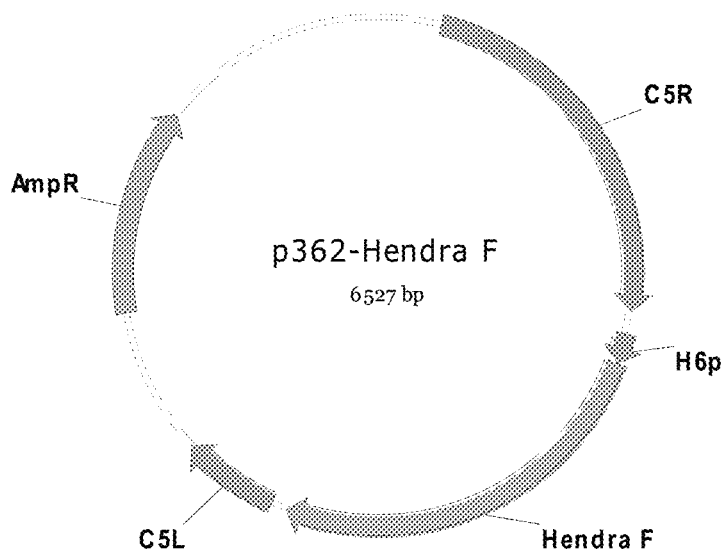
| | | | |
|---|---|---|---|
| C5R | Start: 248 End: 1783; | H6p | Start: 1881 End: 2004 |
| Hendra F | Start: 2005 End: 3645; | C5L | Start: 3709 End: 4113 |
| AmpR | Start: 4726 End: 5583 | | | vCP3004 (Hendra G) Southern Blot

| Lane: | Unique fragments hybridized with Hendra G prob

Western blot of vCP3004 (Hendra G)

Lane 1: Hendra-G pellet 5ul
Lane 2 : Hendra-G p

Southern blot of vCP3005 (Hendra F)

| Lane: |

Figure 6

Western Blot of vCP3005 (Hendra F)

| Lane 1: Hendra-G pellet 5ul |
| Lane 2 : Hendra-G pellet 10ul |
| Lane 3 : Hendra-G pellte 20ul |
| Lane 4 : ALVAC-G pellet 20ul |
| Lane 5 : CEF cell pellet |
| Lane 6 : Marker |

58kD ←

← F0 protein

Figure 7
Fusion Assay
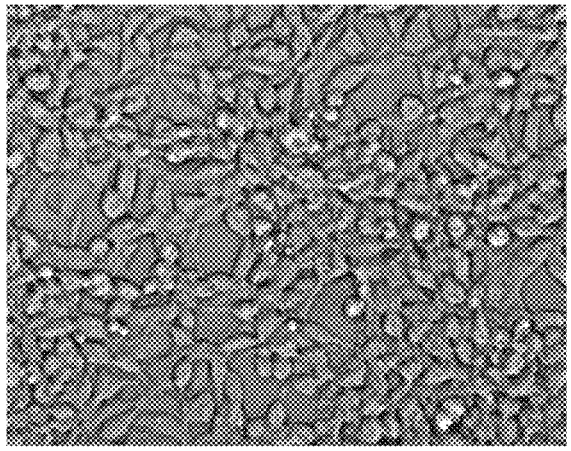
ALVAC-G (vCP3004)
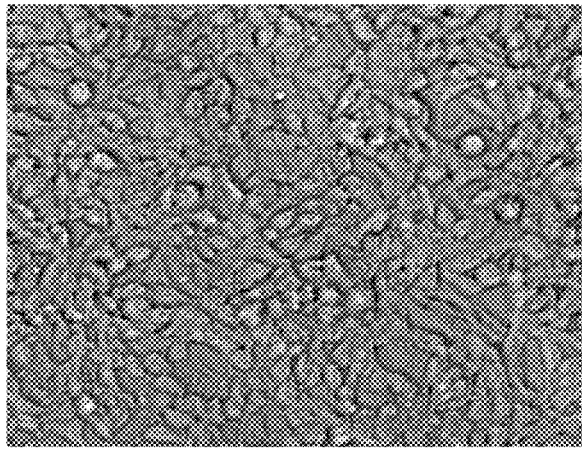
ALVAC-F (vCP3005)
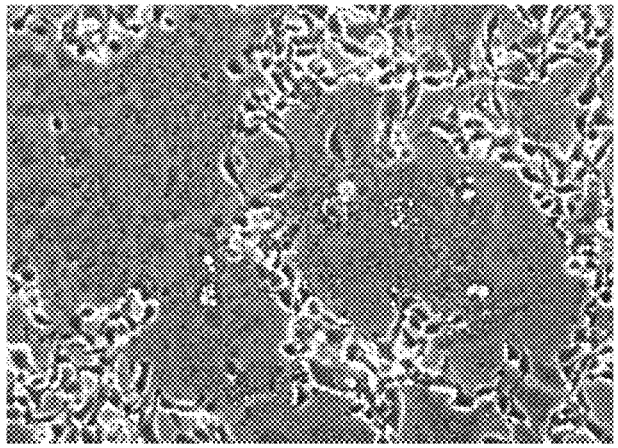
ALVAC-G (vCP3004) + ALVAC-F (vCP3005)

A.

HeV-G Binding assay - ELISA

| horse | Day 0 | Day 14 | Day 28 | Day 71 |
|---|---|---|---|---|
| 68486 | 469.5 | 429 | 470.5 | 1785 |
| 68612 | 140 | 180.5 | 163 | 6134.5 |
| 68871 | 625.5 | 475.5 | 823 | 9590.5 |
| 92604 | 239 | 1149 | 549 | 1781 |
| 68382 | 168 | 535.5 | 1519 | 5015 |
| 68473 | 242 | 407 | 5674.5 | 14668.5 |
| 68490 | 284 | 1111 | 5247 | 8588 |
| 68517 | 123 | 322.5 | 877 | 4324.5 |

B.

HeV-G Blocking assay - ELISA

|       | Day 0   | Day 14  | Day 28  | Day 71  |
|-------|---------|---------|---------|---------|
| 68486 | 15079.5 | 15048.5 | 15238.5 | 15902.5 |
| 68612 | 14693   | 14486   | 15556   | 10525   |
| 68871 | 14651.5 | 15313   | 14809.5 | 8111.5  |
| 92604 | 15266.5 | 14900.5 | 14403.5 | 12844   |
| 68382 | 14061   | 13187   | 11679.5 | 9625    |
| 68473 | 15051   | 14510.5 | 11220   | 5521    |
| 68490 | 16298.5 | 15341   | 11623.5 | 9500    |
| 68517 | 14830   | 15252   | 14024.5 | 12601.5 |

Figure 8C

C. SNT

HeV-R (Hendra- Redlands isolated in 2008)

|  | Day 0 | Day 14 | Day 28 | Day 70 |
|---|---|---|---|---|
| Horse # 68486 | <2 | <2 | 2, 2 | 32, 64 |
| Horse # 68612 | <2 | 8, 8 | 8, 8 | 128, 128 |
| Horse # 68871 | <2 | 2, 2 | 4, 4 | 32, 128 |
| Horse # 92604 | <2 | <2 | Toxic to 4, virus at 8 | 16, 128 |
| Horse # 68382 | <2 | 1, 1 | 16, 32 | 128, 128 |
| Horse # 68473 | <2 | 8, 8 | 32, 64 | 128, 128 |
| Horse # 68490 | <2 | 2, 4 | 16, 16 | 32, 64 |
| Horse # 68517 | <2 | 8, 8 | 16, 16 | 64, 128 |

NiV-G Binding assay – ELISA

| | Day 0 | Day 14 | Day 28 | Day 71 |
|---|---|---|---|---|
| 68486 | 478.5 | 572.5 | 2081 | 19958.5 |
| 68612 | 164 | 5070 | 7808.5 | 22931 |
| 68871 | 2023.5 | 1760 | 6930 | 22762 |
| 92604 | 291 | 1360 | 6497 | 20215 |
| 68382 | 137 | 2682 | 20393 | 22366 |
| 68473 | 211 | 10365 | 22799 | 23973.5 |
| 68490 | 114 | 3798.5 | 16286 | 22770 |
| 68517 | 123 | 9364 | 17364 | 23894.5 |

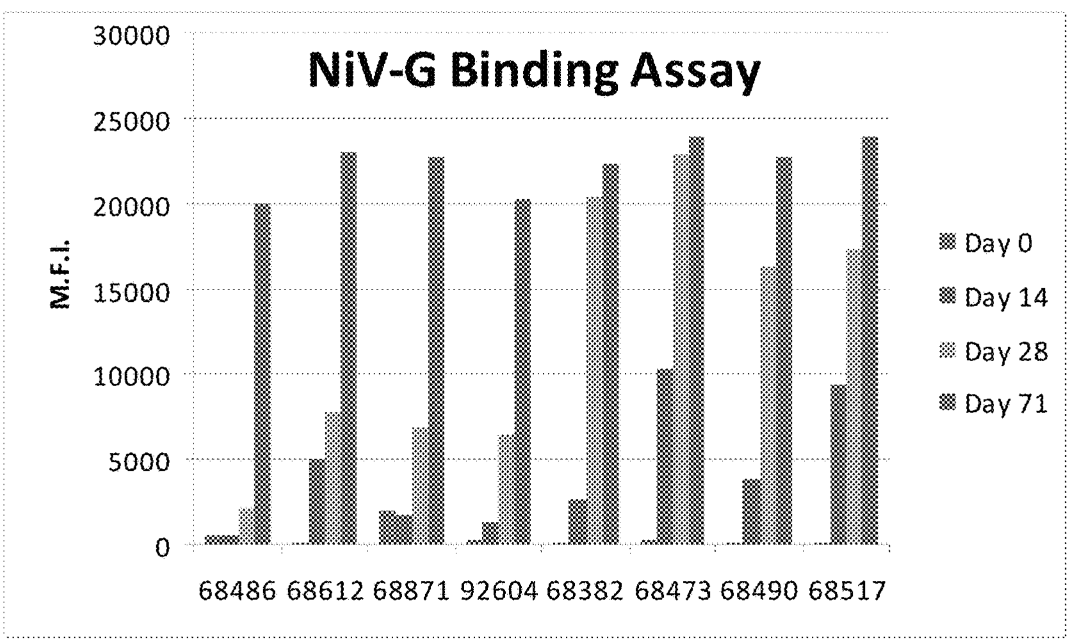

NiV-G Blocking assay – ELISA

|       | Day 0   | Day 14  | Day 28  | Day 71  |
|-------|---------|---------|---------|---------|
| 68486 | 23810.5 | 23720.5 | 23283   | 11623.5 |
| 68612 | 25463   | 25167   | 23392.5 | 8593    |
| 68871 | 25390.5 | 23559.5 | 23717.5 | 5227.5  |
| 92604 | 23706   | 23756   | 23563   | 16667.5 |
| 68382 | 24031.5 | 24946.5 | 15660   | 4688.5  |
| 68473 | 23936.5 | 24805   | 11890   | 1600    |
| 68490 | 23958.5 | 24957   | 14861   | 7876.5  |
| 68517 | 23770   | 23531.5 | 23149   | 7567.5  |

Figure 9C

C. SNT

NiV-B (Nipah-Bengladesh)

|              | Day 0                      | Day 14                   | Day 28                            | Day 70 |
|--------------|----------------------------|--------------------------|-----------------------------------|--------|
| Horse # 68486 | <2                        | <2                       | 2, 2                              | 4, 8   |
| Horse # 68612 | <2                        | <2                       | <2, 2                             | 16, 32 |
| Horse # 68871 | <2                        | 2, 2                     | 8, 8                              | 32, 64 |
| Horse # 92604 | <2                        | Toxic to 8, virus at 16  | Toxic to 8, virus at 16, 32       | 16, 64 |
| Horse # 68382 | <2                        | <2                       | 8, 16                             | 32, 32 |
| Horse # 68473 | <2                        | <2                       | 16, 32                            | 64, 64 |
| Horse # 68490 | Toxic to 8, virus at 16   | <2                       | 16, 16                            | 16, 32 |
| Horse # 68517 | <2                        | <2                       | 4, 8                              | 16, 32 |

SEQ ID NO:1 (wildtype DNA encoding Hendra G protein) 1815bp
ATGATGGCTGATTCCAAATTGGTAAGCCTGAACAATAATCTATCTGGTAAAATCAAGGATCAAGGTAAAG
TTATCAAGAATTATTACGGCACAATGGACATCAAGAAAATTAACGATGGGTTATTAGATAGTAAGATACT
TGGGGCGTTTAACACAGTGATAGCTTTGTTGGGATCAATCATCATCATTGTGATGAATATCATGATAATT
CAAAATTACACCAGAACGACTGATAATCAGGCACTAATCAAAGAGTCACTCCAGAGTGTACAGCAACAAA
TCAAAGCTTTAACAGACAAAATCGGGACAGAGATAGGCCCCAAAGTCTCACTAATTGACACATCCAGCAC
CATCACAATTCCTGCTAACATAGGGTTACTGGGATCCAAGATAAGTCAGTCTACCAGCAGTATTAATGAG
AATGTTAACGATAAATGCAAATTTACTCTTCCTCCTTTAAAGATTCATGAGTGTAATATCTCTTGTCCGA
ATCCTTTGCCTTTCAGAGAATACCGACCAATCTCACAAGGGGTGAGTGATCTTGTAGGACTGCCGAACCA
GATCTGTCTACAGAAGACAACATCAACAATCTTAAAGCCCAGGCTGATATCCTATACTCTACCAATTAAT
ACCAGAGAAGGGGTTTGCATCACTGACCCACTTTTGGCTGTTGATAATGGCTTCTTCGCCTATAGCCATC
TTGAAAAGATCGGATCATGTACTAGAGGAATTGCAAAACAAAGGATAATAGGGGTGGGTGAGGTATTGGA
TAGGGGTGATAAGGTGCCATCAATGTTTATGACCAATGTTTGGACACCACCCAATCCAAGCACCATCCAT
CATTGCAGCTCAACTTACCATGAAGATTTTTATTACACATTGTGCGCAGTGTCCCATGTGGGAGATCCTA
TCCTTAACAGTACTTCCTGGACAGAGTCACTGTCTCTGATTCGTCTTGCTGTAAGACCAAAAAGTGATAG
TGGAGACTACAATCAGAAATACATCGCTATAACTAAAGTTGAAAGAGGGAAGTACGATAAGGTGATGCCT
TACGGTCCATCAGGTATCAAGCAAGGGGATACATTGTACTTTCCGGCCGTCGGTTTTTTGCCAAGGACCG
AATTTCAATATAATGACTCTAATTGTCCCATAATTCATTGCAAGTACAGCAAAGCAGAAAACTGTAGGCT
TTCAATGGGTGTCAACTCCAAAAGTCATTATATTTTGAGATCAGGACTATTGAAGTATAATCTATCTCTT
GGAGGAGACATCATACTCCAATTTATCGAGATTGCTGACAATAGATTGACCATCGGTTCTCCTAGTAAGA
TATACAATTCCCTAGGTCAACCCGTTTTCTACCAGGCATCATATTCTTGGGATACGATGATTAAATTAGG
CGATGTTGATACCGTTGACCCTCTAAGAGTACAGTGGAGAAATAACAGTGTGATTTCTAGACCTGGACAG
TCACAGTGTCCTCGATTTAATGTCTGTCCCGAGGTATGCTGGGAAGGGACATATAATGATGCTTTTCTAA
TAGACCGGCTAAACTGGGTTAGTGCTGGTGTTTATTTAAACAGTAACCAAACTGCAGAGAACCCTGTGTT
TGCCGTATTCAAGGATAACGAGATCCTTTACCAAGTTCCACTGGCTGAAGATGACACAAATGCACAAAAA
ACCATCACAGATTGCTTCTTGCTGGAGAATGTCATATGGTGTATATCACTAGTAGAAATATACGATACAG
GAGACAGTGTGATAAGGCCAAAACTATTTGCAGTCAAGATACCTGCCCAATGTTCAGAGAGTTGA

SEQ ID NO:2 (codon-optimized DNA encoding Hendra G protein) 1812bp
ATGGCCGACTCCAAGCTGGTGTCTCTGAACAATAACCTGAGCGGCAAGATCAAAGACCAGGGCAAAGTGA
TCAAGAACTACTATGGAACCATGGACATCAAGAAGATCAACGACGGACTGCTGGATTCCAAGATCCTGGG
CGCCTTCAACACAGTGATCGCTCTGCTGGGCTCTATCATCATCATCGTGATGAACATCATGATCATCCAG
AATTACACCAGAACCACAGACAACCAGGCCCTGATCAAGGAGTCTCTGCAGAGCGTGCAGCAGCAGATCA
AGGCTCTGACCGACAAAATCGGGACAGAAATCGGACCCAAGGTGAGCCTGATCGATACCAGCTCCACCAT
CACAATCCCTGCCAACATCGGACTGCTGGGCTCCAAAATCAGCCAGTCCACCTCTAGCATCAACGAGAAT
GTGAACGACAAGTGCAAATTCACACTGCCCCCTCTGAAGATCCACGAGTGCAACATCAGCTGTCCAAATC
CCCTGCCTTTTAGGGAATACAGACCTATCAGCCAGGGAGTGTCCGACCTGGTGGGACTGCCAAACCAGAT
CTGTCTGCAGAAGACCACATCCACCATCCTGAAACCTAGGCTGATCTCTTACACCCTGCCAATCAACACA
AGAGAGGGCGTGTGCATCACAGACCCCCTGCTGGCCGTGGATAATGGGTTCTTTGCTTATAGCCATCTGG
AGAAGATCGGATCCTGTACCAGGGGCATCGCCAAACAGAGAATCATCGGGGTGGGAGAAGTGCTGGACAG
GGGCGATAAGGTGCCAAGCATGTTCATGACCAACGTGTGGACACCACCCAATCCCTCCACCATCCACCAT
TGCTCCTCTACATACCACGAGGACTTTTACTATACCCTGTGTGCCGTGTCCCATGTGGGCGATCCAATCC
TGAACTCTACCAGCTGGACAGAATCCCTGTCTCTGATCAGGCTGGCCGTGAGACCTAAGAGCGACTCCGG
GGATTACAATCAGAAGTATATCGCTATCACCAAAGTGGAGAGGGAAAGTACGACAAAGTGATGCCATAT
GGGCCCAGCGGAATCAAGCAGGGCGATACCCTGTACTTCCCGCCGTGGGGTTTCTGCCTAGAACAGAGT
TCCAGTACAACGACTCCAATTGCCCCATCATCCACTGTAAGTATTCTAAAGCTGAAAACTGCAGGCTGAG
CATGGGAGTGAATTCTAAGAGCCATTACATCCTGAGATCCGGCCTGCTGAAATATAACCTGTCTCTGGGC
GGGGACATCATCCTGCAGTTCATCGAGATCGCCGATAACAGACTGACCATCGGGTCCCCCTCAAGATCT
ACAATAGCCTGGGACAGCCTGTGTTTTACCAGGCTAGCTATTCCTGGGACACCATGATCAAACTGGGCGA
CGTGGATACAGTGGATCCTCTGCGCGTGCAGTGGCGGAATAACTCCGTGATCTCTAGGCCAGGACAGTCC

Figure 11B

CAGTGTCCCAGATTCAACGTGTGCCCTGAAGTGTGTTGGGAAGGCACCTACAACGACGCCTTTCTGATCG
ATAGGCTGAATTGGGTGTCTGCTGGGGTGTATCTGAATAGCAACCAGACAGCCGAGAACCCTGTGTTCGC
TGTGTTTAAGGACAATGAGATCCTGTACCAGGTGCCACTGGCCGAAGACGATACCAACGCTCAGAAAACC
ATCACAGATTGCTTCCTGCTGGAGAATGTGATCTGGTGTATCTCTCTGGTGGAAATCTATGACACCGGCG
ATAGCGTGATCAGACCCAAGCTGTTTGCCGTGAAAATCCCTGCTCAGTGCTCTGAAAGCTGA

SEQ ID NO:3  Hendra virus G protein

```
  1    MADSKLVSLN  NNLSGKIKDQ  GKVIKNYYGT  MDIKKINDGL  LDSKILGAFN
 51    TVIALLGSII  IIVMNIMIIQ  NYTRTTDNQA  LIKESLQSVQ  QQIKALTDKI
101    GTEIGPKVSL  IDTSSTITIP  ANIGLLGSKI  SQSTSSINEN  VNDKCKFTLP
151    PLKIHECNIS  CPNPLPFREY  RPISQGVSDL  VGLPNQICLQ  KTTSTILKPR
201    LISYTLPINT  REGVCITDPL  LAVDNGFFAY  SHLEKIGSCT  RGIAKQRIIG
251    VGEVLDRGDK  VPSMFMTNVW  TPPNPSTIHH  CSSTYHEDFY  YTLCAVSHVG
301    DPILNSTSWT  ESLSLIRLAV  RPKSDSGDYN  QKYIAITKVE  RGKYDKVMPY
351    GPSGIKQGDT  LYFPAVGFLP  RTEFQYNDSN  CPIIHCKYSK  AENCRLSMGV
401    NSKSHYILRS  GLLKYNLSLG  GDIILQFIEI  ADNRLTIGSP  SKIYNSLGQP
451    VFYQASYSWD  TMIKLGDVDT  VDPLRVQWRN  NSVISRPGQS  QCPRFNVCPE
501    VCWEGTYNDA  FLIDRLNWVS  AGVYLNSNQT  AENPVFAVFK  DNEILYQVPL
551    AEDDTNAQKT  ITDCFLLENV  IWCISLVEIY  DTGDSVIRPK  LFAVKIPAQC
```

SEQ ID NO:4 (wildtype DNA encoding Hendra F protein) 1641bp
ATGGCTACACAAGAGGTCAGGCTAAAGTGTTTGCTCTGTGGGATCATAGTTCTGGTTTTGTCATTAGAAG
GGCTAGGGATACTACATTATGAGAAACTTAGTAAGATAGGGCTGGTTAAAGGTATTACAAGAAAGTACAA
GATTAAGAGTAACCCTTTGACCAAGGATATTGTGATCAAAATGATCCCTAATGTCTCGAATGTCTCAAAG
TGCACCGGGACTGTTATGGAGAATTACAAAAGCAGACTCACAGGGATTCTCTCACCAATCAAAGGCGCCA
TCGAACTGTACAATAATAACACGCATGACCTAGTTGGTGATGTCAAGCTTGCAGGTGTGGTGATGGCAGG
GATTGCAATCGGGATAGCTACTGCTGCACAAATCACAGCAGGTGTTGCCTTATATGAGGCAATGAAGAAC
GCAGACAATATCAATAAACTCAAGAGCAGCATAGAGTCTACAAATGAGGCTGTTGTCAAATTACAGGAAA
CAGCTGAGAAAACAGTCTACGTCCTTACTGCTCTTCAAGATTACATCAACACTAACCTTGTTCCTACAAT
AGATCAAATTAGCTGCAAGCAAACAGAGCTCGCATTAGACTTGGCGTTGTCTAAGTATCTGTCTGATCTG
CTCTTTGTTTTCGGACCTAACTTACAGGATCCAGTCTCTAATTCCATGACTATCCAAGCAATATCTCAAG
CATTTGGGGGCAATTACGAAACCTTACTGAGAACGCTTGGTTACGCGACCGAGGACTTCGACGACCTTTT
AGAAAGTGATAGCATAGCAGGCCAGATAGTCTATGTAGATCTCAGTAGCTATTACATAATAGTAAGGGTG
TATTTTCCCATACTAACAGAGATCCAACAGGCTTATGTGCAGGAGTTGCTTCCAGTGAGTTTTAATAACG
ATAATTCAGAATGGATCAGCATTGTCCCGAATTTCGTGCTGATTAGGAACACGCTGATTTCAAATATAGA
AGTCAAGTACTGCTTAATCACCAAGAAAGTGTGATTTGTAATCAGGACTATGCTACACCCATGACGGCT
AGCGTGAGAGAATGCTTGACAGGATCCACAGATAAGTGCCCAAGGGAGTTAGTAGTCTCATCCCATGTTC
CAAGATTTGCCCTCTCAGGAGGAGTCTTGTTTGCAAATTGTATAAGTGTGACATGTCAGTGTCAGACTAC
TGGGAGGGCAATATCTCAATCAGGGAACAGACACTACTGATGATTGACAATACTACCTGCACAACAGTT
GTTCTAGGAAACATAATCATAAGCCTTGGAAAATATTTGGGATCAATAAATTACAATTCTGAGAGCATTG
CTGTTGGGCCACCAGTCTATACAGACAAAGTTGATATCTCAAGTCAGATATCTAGTATGAATCAATCACT
ACAACAATCTAAGGATTACATTAAAGAAGCTCAAAAGATCTTGGACACTGTGAATCCGTCGTTGATAAGT
ATGCTATCAATGATCATCCTTTATGTTTTGTCCATTGCAGCACTGTGCATTGGTCTGATCACTTTCATAA
GCTTTGTAATAGTTGAGAAAAGAGAGGGAATTACAGCAGGCTAGATGATAGGCAAGTGCGACCGGTCAG
TAATGGTGATCTGTATTATATTGGAACATAA

Figure 11C

SEQ ID NO:5 (codon-optimized DNA encoding Hendra F protein) 1641bp
ATGGCCACCCAGGAGGTGCGCCTGAAGTGCCTGCTGTGTGGCATCATCGTGCTGGTGCTGAGCCTGGAGG
GACTGGGAATCCTGCACTACGAAAAACTGTCCAAGATCGGCCTGGTGAAGGGGATCACCCGGAAGTATAA
AATCAAGAGCAATCCCCTGACAAAGGACATCGTGATCAAAATGATCCCTAATGTGAGCAACGTGTCCAAG
TGCACCGGCACAGTGATGGAGAACTACAAATCTAGGCTGACCGGGATCCTGAGCCCTATCAAGGGAGCCA
TCGAACTGTATAACAATAACACACATGACCTGGTGGGCGATGTGAAACTGGCCGGGGTGGTCATGGCCGG
AATCGCTATCGGCATCGCTACCGCTGCTCAGATCACAGCTGGAGTGGCTCTGTACGAGGCCATGAAGAAT
GCTGACAATATCAACAAACTGAAGAGCTCCATCGAGTCCACCAACGAAGCCGTGGTGAAGCTGCAGGAGA
CCGCTGAAAAAACAGTGTACGTGCTGACAGCCCTGCAGGACTATATCAATACCAACCTGGTGCCAACAAT
CGATCAGATCAGCTGTAAGCAGACCGAACTGGCCCTGGACCTGGCTCTGTCTAAATACCTGAGCGATCTG
CTGTTCGTGTTTGGCCCAAATCTGCAGGATCCCGTGTCCAACTCTATGACCATCCAGGCCATCTCCCAGG
CTTTCGGCGGGAACTACGAGACCCTGCTGAGGACACTGGGGTATGCCACCGAGGACTTTGACGATCTGCT
GGAAAGCGATTCCATCGCTGGACAGATCGTGTACGTGGACCTGTCTAGCTACTATATCATCGTGAGAGTG
TACTTCCCAATCCTGACCGAGATCCAGCAGGCCTATGTGCAGGAACTGCTGCCCGTGAGCTTCAATAACG
ATAATTCCGAGTGGATCTCTATCGTGCCTAACTTTGTGCTGATCCGCAATACCCTGATCTCTAACATCGA
AGTGAAGTACTGCCTGATCACAAAGAAAAGCGTGATCTGTAACCAGGACTATGCCACCCCCATGACAGCT
AGCGTGCGGGAGTGCCTGACCGGATCCACCGATAAGTGTCCTAGGGAACTGGTGGTGTCCTCTCACGTGC
CAAGATTCGCCCTGTCTGGAGGCGTGCTGTTTGCTAACTGCATCAGCGTGACCTGCCAGTGTCAGACCAC
AGGCAGAGCCATCTCTCAGAGCGGGGAGCAGACACTGCTGATGATCGACAATACCACATGTACCACAGTG
GTGCTGGGCAACATCATCATCTCCCTGGGGAAGTACCTGGGATCTATCAATTATAACTCCGAATCTATCG
CCGTGGGGCCCCCTGTGTACACCGACAAAGTGGACATCAGCAGCCAGATCTCTAGCATGAATCAGAGCCT
GCAGCAGTCCAAAGACTATATCAAGGAGGCCCAGAAAATCCTGGATACCGTGAACCCATCTCTGATCAGC
ATGCTGTCCATGATCATCCTGTACGTGCTGTCCATCGCCGCTCTGTGCATCGGACTGATCACCTTCATCA
GCTTTGTGATCGTGGAGAAGAAACGCGGCAATTACTCCCGGCTGGACGATAGGCAGGTGAGACCCGTGTC
TAACGGAGACCTGTACTATATCGGCACCTGA

SEQ ID NO:6  Hendra virus F protein
```
  1  MATQEVRLKC LLCGIIVLVL SLEGLGILHY EKLSKIGLVK GITRKYKIKS
 51  NPLTKDIVIK MIPNVSNVSK CTGTVMENYK SRLTGILSPI KGAIELYNNN
101  THDLVGDVKL AGVVMAGIAI GIATAAQITA GVALYEAMKN ADNINKLKSS
151  IESTNEAVVK LQETAEKTVY VLTALQDYIN TNLVPTIDQI SCKQTELALD
201  LALSKYLSDL LFVFGPNLQD PVSNSMTIQA ISQAFGGNYE TLLRTLGYAT
251  EDFDDLLESD SIAGQIVYVD LSSYYIIVRV YFPILTEIQQ AYVQELLPVS
301  FNNDNSEWIS IVPNFVLIRN TLISNIEVKY CLITKKSVIC NQDYATPMTA
351  SVRECLTGST DKCPRELVVS SHVPRFALSG GVLFANCISV TCQCQTTGRA
401  ISQSGEQTLL MIDNTTCTTV VLGNIIISLG KYLGSINYNS ESIAVGPPVY
451  TDKVDISSQI SSMNQSLQQS KDYIKEAQKI LDTVNPSLIS MLSMIILYVL
501  SIAALCIGLI TFISFVIVEK KRGNYSRLDD RQVRPVSNGD LYYIGT*
```

SEQ ID NO:7  P362-Hendra G plasmid containing H6 promoter and G gene

```
       => H6p
  1  TTCTTTATTCTATACTTAAAAAGTGAAAATAAATACAAAGGTTCTTGAGGGTTGTGTTAA
 61  ATTGAAAGCGAGAAATAATCATAAATTATTTCATTATCGCGATATCCGTTAAGTTTGTAT
       => Hendra G  (protein sequence SEQ ID NO:3)
             M   A   D   S   K   L   V   S   L   N   N   N   L   S   G   K   I   K   D
121  CGTAATGGCCGACTCCAAGCTGGTGTCTCTGAACAATAACCTGAGCGGCAAGATCAAAGA
       Q   G   K   V   I   K   N   Y   Y   G   T   M   D   I   K   K   I   N   D   G
181  CCAGGGCAAAGTGATCAAGAACTACTATGGAACCATGGACATCAAGAAGATCAACGACGG
       L   L   D   S   K   I   L   G   A   F   N   T   V   I   A   L   L   G   S   I
241  ACTGCTGGATTCCAAGATCCTGGGCGCCTTCAACACAGTGATCGCTCTGCTGGGCTCTAT
       I   I   I   V   M   N   I   M   I   I   Q   N   Y   T   R   T   T   D   N   Q
301  CATCATCATCGTGATGAACATCATGATCATCCAGAATTACACCAGAACCACAGACAACCA
       A   L   I   K   E   S   L   Q   S   V   Q   Q   Q   I   K   A   L   T   D   K
```

Figure 11D

```
 361 GGCCCTGATCAAGGAGTCTCTGCAGAGCGTGCAGCAGCAGATCAAGGCTCTGACCGACAA
      I  G  T  E  I  G  P  K  V  S  L  I  D  T  S  S  T  I  T  I
 421 AATCGGGACAGAAATCGGACCCAAGGTGAGCCTGATCGATACCAGCTCCACCATCACAAT
      P  A  N  I  G  L  L  G  S  K  I  S  Q  S  T  S  S  I  N  E
 481 CCCTGCCAACATCGGACTGCTGGGCTCCAAAATCAGCCAGTCCACCTCTAGCATCAACGA
      N  V  N  D  K  C  K  F  T  L  P  P  L  K  I  H  E  C  N  I
 541 GAATGTGAACGACAAGTGCAAATTCACACTGCCCCCTCTGAAGATCCACGAGTGCAACAT
      S  C  P  N  P  L  P  F  R  E  Y  R  P  I  S  Q  G  V  S  D
 601 CAGCTGTCCAAATCCCCTGCCTTTTAGGGAATACAGACCTATCAGCCAGGGAGTGTCCGA
      L  V  G  L  P  N  Q  I  C  L  Q  K  T  T  S  T  I  L  K  P
 661 CCTGGTGGGACTGCCAAACCAGATCTGTCTGCAGAAGACCACATCCACCATCCTGAAACC
      R  L  I  S  Y  T  L  P  I  N  T  R  E  G  V  C  I  T  D  P
 721 TAGGCTGATCTCTTACACCCTGCCAATCAACACAAGAGAGGGCGTGTGCATCACAGACCC
      L  L  A  V  D  N  G  F  F  A  Y  S  H  L  E  K  I  G  S  C
 781 CCTGCTGGCCGTGGATAATGGGTTCTTTGCTTATAGCCATCTGGAGAAGATCGGATCCTG
      T  R  G  I  A  K  Q  R  I  I  G  V  E  V  L  D  R  G  D
 841 TACCAGGGGCATCGCCAAACAGAGAATCATCGGGGTGGGAGAAGTGCTGGACAGGGGCGA
      K  V  P  S  M  F  M  T  N  V  W  T  P  P  N  P  S  T  I  H
 901 TAAGGTGCCAAGCATGTTCATGACCAACGTGTGGACACCACCCAATCCTCCACCATCCA
      H  C  S  S  T  Y  H  E  D  F  Y  Y  T  L  C  A  V  S  H  V
 961 CCATTGCTCCTCTACATACCACGAGGACTTTTACTATACCCTGTGTGCCGTGTCCCATGT
      G  D  P  I  L  N  S  T  S  W  T  E  S  L  S  I  R  L  A
1021 GGGCGATCCAATCCTGAACTCTACCAGCTGGACAGAATCCCTGTCTCTGATCAGGCTGGC
      V  R  P  K  S  D  S  G  D  Y  N  Q  K  Y  I  A  I  T  K  V
1081 CGTGAGACCTAAGAGCGACTCCGGGGATTACAATCAGAAGTATATCGCTATCACCAAAGT
      E  R  G  K  Y  D  K  V  M  P  Y  G  S  G  I  K  Q  G  R
1141 GGAGAGGGGAAAGTACGACAAAGTGATGCCATATGGGCCCAGCGGAATCAAGCAGGGCGA
      T  L  Y  F  P  A  V  G  F  L  P  R  T  E  F  Q  Y  N  D  S
1201 TACCCTGTACTTCCCCGCCGTGGGGTTTCTGCCTAGAACAGAGTTCCAGTACAACGACTC
      N  C  P  I  I  R  C  K  Y  S  K  A  E  N  C  R  L  S  M  G
1261 CAATTGCCCCATCATCCACTGTAAGTATTCTAAAGCTGAAAACTGCAGGCTGAGCATGGG
      V  N  S  K  S  H  Y  I  L  R  S  G  L  L  K  Y  N  L  S  L
1321 AGTGAATTCTAAGAGCCATTACATCCTGAGATCCGGCCTGCTGAAATATAACCTGTCTCT
      G  G  D  I  I  L  Q  F  I  E  I  A  D  N  R  L  T  I  G  S
1381 GGGCGGGGACATCATCCTGCAGTTCATCGAGATCGCCGATAACAGACTGACCATCGGGTC
      P  S  K  I  Y  N  S  L  G  Q  P  V  F  Y  Q  A  S  Y  S  W
1441 CCCCTCTAAGATCTACAATAGCCTGGGACAGCCTGTGTTTTACCAGGCTAGCTATTCCTG
      D  T  M  I  K  L  G  D  V  D  T  V  D  P  L  R  V  Q  W  R
1501 GGACACCATGATCAAACTGGGCGACGTGGATACAGTGGATCCTCTGCGCGTGCAGTGGCG
      N  N  S  V  I  S  R  P  G  Q  S  Q  C  P  R  F  N  V  C  P
1561 GAATAACTCCGTGATCTCTAGGCCAGGACAGTCCCAGTGTCCCAGATTCAACGTGTGCCC
      E  V  C  W  E  G  T  Y  N  D  A  F  L  I  D  R  L  N  W  V
1621 TGAAGTGTGTTGGGAAGGCACCTACAACGACGCCTTTCTGATCGATAGGCTGAATTGGGT
      S  A  G  V  Y  L  N  S  N  Q  T  A  E  N  P  V  F  A  V  F
1681 GTCTGCTGGGGTGTATCTGAATAGCAACCAGACAGCCGAGAACCCTGTGTTCGCTGTGTT
      K  D  N  E  I  L  Y  Q  V  P  L  A  E  D  D  T  N  A  Q  K
1741 TAAGGACAATGAGATCCTGTACCAGGTGCCACTGGCCGAAGACGATACCAACGCTCAGAA
      T  I  T  D  C  F  L  L  E  N  V  I  W  C  I  S  L  V  E  I
1801 AACCATCACAGATTGCTTCCTGCTGGAGAATGTGATCTGGTGTATCTCTCTGGTGGAAAT
      Y  D  T  G  D  S  V  I  R  P  K  L  F  A  V  K  I  P  A  Q
1861 CTATGACACCGGCGATAGCGTGATCAGACCCAAGCTGTTTGCCGTGAAAATCCCTGCTCA
      C  S  E  S  *
1921 GTGCTCTGAAAGCTGA
```

SEQ ID NO:8   P362-Hendra G plasmid containing H6 promoter, G gene and C5 arms

```
                                   M13R
                         GGAAA CAGCTATGAC CATGATTACG AATTGCGGCC
          => C5R
         GCAATTCTGA ATGTTAAATG TTATACTTTG GATGAAGCTA TAAATATGCA TTGGAAAAT
         AATCCATTA AAGAAGGAT TCAAATACTA CAAAACCTAA GCGATAATAT GTTAACTAAG
         CTTATTCTTA ACGACGCTTT AATATACAC AAATAAACAT AATTTTTGTA TAACCTAACA
         AATAACTAAA ACATAAAAAT AATAAAAGGA AATGTAATAT CGTAATTATT TTACTCAGGA
         ATGGGGTTAA ATATTTATAT CACGTGTATA TCTATACTGT TATCGTATAC TCTTTACAAT
         TACTATTACG AATATGCAAG AGAATAATAAG ATTACGTATT TAAGAGAATC TTGTCATGAT
         AATTGGGTAC GACATAGTGA TAAATGCTAT TTCGCATCGT TACATAAAGT CAGTTGGAAA
```

Figure 11E

```
GATGGATTTG ACAGATGTAA CTTAATAGCT GCAAAAATGT TAAATAACAG CATTCTATCG
GAAGATAGGA TACCAGTTAT ATTATACAAA AATCACTGGT TGGATAAAAC AGATTCTGCA
ATATTCGTAA AAGATGAAGA TTACTGCGAA TTTGTAAACT ATGACAATAA AAAGCCATTT
ATCTCAACGA CATCGTGTAA TTCTTCCATG TTTTATGTAT GTGTTCAGA TATTATGAGA
TTACTATAAA CTTTTGTAT ACTTATATTC CGTACACTAT ATTAATCATG AAGAAAATGA
AAAAGTATAG AAGCTGTTCA CGAGCGGTTG TTGAAAACAA CAAAATTATA CATTCAAGAT
GGCTACATA TACGTCTGTG AGGCTATCAT GGATAATGAC AATGCATCTC TAAATAGGTT
TTTGGACAAT GGATTCGACC CTAACACGGA ATATGGTACT CTACAATCTC CTCTTGAAAT
GGCTGTAATG TTCAAGAATA CCGAGGCTAT AAAAATCTTG ATGAGGTATG GAGCTAAACC
TGTAGTTACT GAATGCACAA CTTCTTGTCT GCATGATGCG GTGTTGAGAG ACGACTACAA
AATAGTGAAA GATCTGTTGA AGAATAACTA TGTAAACAAT GTTCTTACA GCGGAGGCTT
TACTCCTTTG TGTTGGCAG CTTACCTTAA CAAAGTTAAT TTGGTTAAGA TTCTATTGGC
TCATTCGGCG GATGTAGATA TTTCAAACAC GGATCGGTTA ACTCCTCTAC ATATAGCCGT
ATCAAATAAA AATTTAACAA TGGTTAAACT TCTATTGAAC AAAGGTGCTG ATACTGACTT
GCTGGATAAC ATGGACGTA CTCCTTAAT GATCGCTGTA CAATCTGGAA ATATTGAAAT
ATGAGCACA CTACTTAAAA AAATAAAAT GTCCAGAACT GGGAAAAATT GATCTTGCCA
GCTGTAATTC ATGGTAGAAA AGAAGTGCTC AGGCTACTTT TCAACAAAGG AGCAGATGTA
AACTACATCT TGAAAGAAA TGGAAAATCA TATACTGTTT TGGAATTGAT TAAAGAAAGT
TACTCTGAGA CACAAAAGAG GTAGCTGAAG TGGTACTCTC AAAGGTACGT GACTAATTAG
CTATAAAAAG GATCCGGGTT AATTAATTAG TCATCAGGCA GGGCGAGAAC GAGACTATCT
                         ⇒ Hǫp
GCTCGTTAAT TAATTAGAGC TTCTTTATTC TATACTTAAA AAGTGAAAAT AAATACAAAG
GTTCTTGAGG GTTGTGTTAA ATTGAAAGCG AGAAATAATC ATAAATTATT TCATTATCGC
                         ⇒ Hendra G (protein sequence SEQ ID NO:3)
    EcoRV                           M   A   D   S   K   L   V   S   L   N   N
GATATCCGTT AAGTTCTAT CGTAATGGCC GACTCCAAGC TGGTGTCTCT GAACAATAAC
  L   S   G   I   K   D   Q   G   K   V   I   K   N   Y   Y   G   T   M   D
CTGAGCGGCA AGATCAAAGA CCAGGGCAAA GTGATCAAGA ACTACTATGG AACCATGGAC
  I   K   K   I   N   D   G   L   L   D   S   K   I   L   G   A   F   N   T   V
ATCAAGAAGA TCAACGACGG ACTGCTGGAT TCCAAGATCC TGGGCGCCTT CAACACAGTG
  I   A   L   L   G   S   I   I   I   V   M   N   I   M   I   I   Q   N   Y
ATCGCTCTGC TGGGCTCTAT CATCATCATC GTGATGAACA TCATGATCAT CCAGAATTAC
  T   R   T   T   D   N   Q   A   L   I   K   E   S   L   Q   S   V   Q   Q   Q
ACCAGAACCA CAGACAACCA GGCCCTGATC AAGGAGTCTC TGCAGAGCGT GCAGCAGCAG
  I   K   A   L   T   D   K   I   G   T   E   I   G   P   K   V   S   L   I   D
ATCAAGGCTC TGACCGACAA AATCGGGACA GAAATCGGAC CCAAGGTGAG CCTGATCGAT
  T   S   S   T   I   T   I   P   A   N   I   G   L   L   G   S   K   I   S   Q
ACCAGCTCCA CCATCACAAT CCCTGCCAAC ATCGGACTGC TGGGCTCCAA AATCAGCCAG
  S   T   S   S   I   N   E   N   V   N   D   K   C   K   F   T   L   P   P   L
TCCACCTCTA GCATCAACGA GAATGTGAAC GACAAGTGCA AATTCACACT GCCCCCTCTG
  K   I   H   E   C   N   I   S   C   P   N   P   L   P   F   R   E   Y   R   P
AAGATCCACG AGTGCAACAT CAGCTGTCCA AATCCCCTGC CTTTTAGGGA ATACAGACCT
  I   S   Q   G   V   S   D   L   V   G   L   P   N   Q   I   C   L   Q   K   T
ATCAGCCAGG GAGTGTCCGA CCTGGTGGGA CTGCCAAACC AGATCTGTCT GCAGAAGACC
  T   S   T   I   L   K   P   R   L   I   S   Y   T   L   F   I   N   T   R   E
ACATCCACCA TCCTGAAACC TAGGCTGATC TCTTACACCC TGTTCATCAA CACAAGAGAG
  G   V   C   I   T   D   F   L   L   A   V   D   N   G   F   F   A   Y   S   H
GGCGTGTGCA TCACAGACCC CCTGCTGGCC GTGGATAATG GGTTCTTTGC TTATAGCCAT
  L   E   K   I   G   S   C   T   R   G   I   A   K   Q   R   I   I   G   V   G
CTGGAGAAGA TCGGATCCTG TACCAGGGGC ATCGCCAAAC AGAGAATCAT CGGGGTGGGA
  E   V   L   D   R   G   D   K   V   P   S   M   F   M   T   N   V   W   T   P
GAAGTGCTGG ACAGGGGCGA TAAGGTGCCA AGCATGTTCA TGACCAACGT GTGGACACCA
  P   N   P   S   T   I   H   H   C   S   S   T   Y   H   E   D   F   Y   Y   T
CCCAATCCCT CCACCATCCA CCATTGCTCC TCTACATACC ACGAGGACTT TTACTATACC
  L   C   A   V   S   H   V   G   D   P   I   L   N   S   T   W   T   E   S
CTGTGTGCCG TGTCCCATGT GGGCGATCCA ATCCTGAACT CTACCAGCTG GACAGAATCC
  L   S   L   I   R   L   A   V   R   P   K   S   D   S   G   D   Y   N   Q   K
CTGTCTCTGA TCAGGCTGGC CGTGAGACCT AAGAGCGACT CCGGGGATTA CAATCAGAAG
  Y   I   A   I   T   K   V   E   R   G   K   Y   D   K   V   M   P   Y   G   P
TATATCGCTA TCACCAAAGT GGAGAGGGGA AAGTACGACA AAGTGATGCC ATATGGGCCC
  S   G   I   K   Q   G   D   T   L   Y   F   P   A   V   G   F   L   P   R   T
AGCGGAATCA AGCAGGGCGA TACCCTGTAC TTCCCCGCCG TGGGGTTTCT GCCTAGAACA
  E   F   Q   Y   N   D   S   N   C   P   I   I   H   C   K   Y   S   K   A   E
GAGTTCCAGT ACAACGACTC CAATTGCCCC ATCATCCACT GTAAGTATTC TAAAGCTGAA
  N   C   R   L   S   M   G   V   N   S   K   S   H   Y   I   L   R   S   G   L
AACTGCAGGC TGAGCATGGG AGTGAATTCT AAGAGCCATT ACATCCTGAG ATCCGGCCTG
```

Figure 11F

```
          L   K   Y   N       L   S   L       G   G   D       I   I   L   Q       F   I   E       I   A   D
CTGAAATATA ACCTGTCTCT GGGCGGGGAC ATCATCCTGC AGTTCATCGA GATCGCCGAT
          N   R   L   T       I   G   S       P   S   K       I   Y   N   S       L   G   Q       P   V   F
AACAGACTGA CCATCGGGTC CCCCTCTAAG ATCTACAATA GCCTGGGACA GCCTGTGTTT
          Y   Q   A   S       Y   S   W       D   T   M       I   K   L   G       D   V   D       T   V   D
TACCAGGCTA GCTATTCCTG GGACACCATG ATCAAACTGG GCGACGTGGA TACAGTGGAT
          P   L   R   V       Q   W   R       N   N   S       V   I   S   R       P   G   Q       S   Q   C
CCTCTGCGCG TGCAGTGGCG GAATAACTCC GTGATCTCTA GGCCAGGACA GTCCCAGTGT
          P   F   N       W   E   G   T       Y   N   D       A   F   L
CCCAGATTCA ACGTGTGCCC TGAAGTGTGT GGGAAGGCA CCTACAACGA CGCCTTTCTG
          I   D   R   L       N   W   V       S   A   G       V   Y   L   N       S   N   Q       T   A   E
ATCGATAGGC TGAATTGGGT GTCTGCTGGG GTGTATCTGA ATAGCAACCA GACAGCCGAG
          N   P   V   F       A   V   F       K   D   N       E   I   L   Y       Q   V   P       L   A   E
AACCCTGTGT TCGCTGTGTT TAAGGACAAT GAGATCCTGT ACCAGGTGCC ACTGGCCGAA
          D   D   T   N       A   Q   K       T   I   T       D   C   F   L       L   E   N       V   I   W
GACGACACCA ACGTCAGAA AACCATCACA GATTGCTTCC TGCTGGAGAA TGTGATCTGG
          C   I   S   L       V   E   I       Y   D   T       G   D   S   V       I   R   P       K   L   F
TGTATCTCTC TGGTGGAAAT CTATGACACC GGCGATAGCG TGATCAGACC CAAGCTGTTT
          A   V   K   I       P   A   Q       C   S   E       S   *                Kpn I
GCCGTGAAAA TCCCTGCTCA GTGCTCTGAA AGCTGATTTT TATGGTACCC TCGAGTCTAG
AATCGATCCC GGGTTTTTAT GACTAGTTAA TCACGGCCGC TTATAAAGAT CTAAAATGCA
TAATTTCTAA ATAATGAAAA AAAGTACATC ATGAGCAACG CGTTAGTATA TTTTACAATG
GAGATTAACG CTCTATACCG TTCTATGTTT ATTGATTCAG ATGATGTTTT AGAAAAGAAA
GTTATTGAAT ATGAAACTT TAATGAAGAT GAAGATGACG ACGATGATGA TTGTTGTAAA
TCTGTTTTAG ATGAAGAAGA TGACGCGCTA AAGTATACTA TGGTTACAAA GTATAAGTCT
ATACTACTAA TGGCGACTTG TGCAAGAAGG TATAGTATAG TCAAAATGTT GTTAGATTAT
GATTATGAAA AACCAAATAA ATCAGATCCA TATCTAAAGG TATCTCCTTT GCACATAATT
TCATCTATTC CTAGTTTAGA ATACCTGCAG CCAAGCTTGG CACTGGCCGT CGTTTTAC
                                              ← M13F
```

SEQ ID NO:10 Plasmid p362-Hendra F containing H6 promoter and F gene

```
      S  F  N  N  D  N  S  E  W  I  S  I  V  P  N  F  V  L  I  R
1021  GAGCTTCAATAACGATAATTCCGAGTGGATCTCTATCGTGCCTAACTTTGTGCTGATCCG
      N  T  L  I  S  N  I  E  V  K  Y  C  L  I  T  K  K  S  V  I
1081  CAATACCCTGATCTCTAACATCGAAGTGAAGTACTGCCTGATCACAAAGAAAAGCGTGAT
      C  N  Q  D  Y  A  T  P  M  T  A  S  V  R  E  C  L  T  G  S
1141  CTGTAACCAGGACTATGCCACCCCCATGACAGCTAGCGTGCGGGAGTGCCTGACCGGATC
      T  D  K  C  P  R  E  L  V  V  S  S  H  V  P  R  F  A  L  S
1201  CACCGATAAGTGTCCTAGGGAACTGGTGGTGTCCTCTCACGTGCCAAGATTCGCCCTGTC
      G  G  V  L  F  A  N  C  I  S  V  T  C  Q  C  Q  T  T  G  R
1261  TGGAGGCGTGCTGTTTGCTAACTGCATCAGCGTGACCTGCCAGTGTCAGACCACAGGCAG
      A  I  S  Q  S  G  E  Q  T  L  L  M  I  D  N  T  T  C  T  T
1321  AGCCATCTCTCAGAGCGGGGAGCAGACACTGCTGATGATCGACAATACCACATGTACCAC
      V  V  L  G  N  I  I  I  S  L  G  K  Y  L  G  S  I  N  Y  N
1381  AGTGGTGCTGGGCAACATCATCATCTCCCTGGGGAAGTACCTGGGATCTATCAATTATAA
      S  E  S  I  A  V  G  P  P  V  Y  T  D  K  V  D  I  S  S  Q
1441  CTCCGAATCTATCGCCGTGGGGCCCCCTGTGTACACCGACAAAGTGGACATCAGCAGCCA
      I  S  S  M  N  Q  S  L  Q  Q  S  K  D  Y  I  K  E  A  Q  K
1501  GATCTCTAGCATGAATCAGAGCCTGCAGCAGTCCAAAGACTATATCAAGGAGGCCCAGAA
      I  L  D  T  V  N  P  S  L  I  S  M  L  S  M  I  I  L  Y  V
1561  AATCCTGGATACCGTGAACCCATCTCTGATCAGCATGCTGTCCATGATCATCCTGTACGT
      L  S  I  A  A  L  C  I  G  L  I  T  F  I  S  F  V  I  V  E
1621  GCTGTCCATCGCCGCTCTGTGCATCGGACTGATCACCTTCATCAGCTTTGTGATCGTGGA
      K  K  R  G  N  Y  S  R  L  D  D  R  Q  V  R  P  V  S  N  G
1681  GAAGAAACGCGGCAATTACTCCCGGCTGGACGATAGGCAGGTGAGACCCGTGTCTAACGG
      D  L  Y  Y  I  G  T  *
1741  AGACCTGTACTATATCGGCACCTGA
```

SEQ ID NO:11 Plasmid p362-Hendra F containing C5 arms, H6 promoter and F gene

```
                                          ⇒ M13R
                                 GGAAA CAGCTATGAC CATGATTACG AATTGCGGCC
           ⇒ C5R
GCAATTCTGA ATGTTAAATG TTATACTTTG GATGAAGCTA TAAATATGCA TTGGAAAAAT
AATCCATTTA AAGAAAGGAT TCAAATACTA CAAAACCTAA GCGATAATAT GTTAACTAAG
CTTATTCTTA ACGACGCTTT AAATATACAC AAATAAACAT AATTTTTGTA TAACCTAACA
AATAACTAAA ACATAAAAAT AATAAAAGGA AATGTAATAT CGTAATTATT TTACTCAGGA
ATGGGGTTAA ATATTTATAT CACGTGTATA TCTATACTGT TATCGTATAC TCTTTACAAT
TACTATTACG AATATGCAAG AGATAATAAG ATTACGTATT TAAGAGAATC TTGTCATGAT
AATTGGGTAC GACATAGTGA TAAATGCTAT TTCGCATCGT TACATAAAGT CAGTTGGAAA
GATGGATTTG ACAGATGTAA CTTAATAGGT GCAAAAATGT TAAATAACAG CATTCTATCG
GAAGATAGGA TACCAGTTAT ATTATACAAA AATCACTGGT TGGATAAAAC AGATTCTGCA
ATATTCGTAA AAGATGAAGA TTACTGCGAA TTTGTAAACT ATGACAATAA AAAGCCATTT
ATCTCAACGA CATCGTGTAA TTCTTCCATG TTTTATGTAT GTGTTTCAGA TATTATGAGA
TTACTATAAA CTTTTTGTAT ACTTATATTC CGTAAACTAT ATTAATCATG AAGAAAATGA
AAAAGTATAG AAGCTGTTCA CGAGCGGTTG TTGAAAACAA CAAAATTATA CATTCAAGAT
GGCTTACATA TACGTCTGTG AGGCTATCAT GGATAATGAC AATGCATCTC TAAATAGGTT
TTTGGACAAT GGATTCGACC CTAACACGGA ATATGGTACT CTACAATCTC CTCTTGAAAT
GGCTGTAATG TTCAAGAATA CCGAGGCTAT AAAAATCTTG ATGAGGTATG GAGCTAAACC
TGTAGTTACT GAATGCACAA CTTCTTGTCT GCATGATGCG GTGTTGAGAG ACGACTACAA
AATAGTGAAA GATCTGTTGA AGAATAACTA TGTAAACAAT GTTCTTTACA GCGGAGGCTT
TACTCCTTTG TGTTTGGCAG CTTACCTTAA CAAAGTTAAT TTGGTTAAAC TTCTATTGGC
TCATTCGGCG GATGTAGATA TTTCAAACAC GGATCGGTTA ACTCCTCTAC ATATAGCCGT
ATCAAATAAA AATTTAACAA TGGTTAAACT TCTATTGAAC AAAGGTGCTG ATACTGACTT
GCTGGATAAC ATGGGACGTA CTCCTTTAAT GATCGCTGTA CAATCTGGAA ATATTGAAAT
ATGTAGCACA CTACTTAAAA AAAATAAAAT GTCCAGAACT GGGAAAAATT GATCTTGCCA
GCTGTAATTC ATGGTAGAAA AGAAGTGCTC AGGCTACTTT TCAACAAAGG AGCAGATGTA
AACTACATCT TTGAAAGAAA TGGAAAATCA TATACTGTTT TGGAATTGAT TAAAGAAAGT
TACTCTGAGA CACAAAAGAG GTAGCTGAAG TGGTACTCTC AAAGGTACGT GACTAATTAG
CTATAAAAAG GATCCGGGTT AATTAATTAG TCATCAGGCA GGGCGAGAAC GAGACTATCT
GCTCGTTAAT TAATTAGAGC TTCTTTATTC TATACTTAAA AAGTGAAAAT AAATACAAAG
GTTCTTGAGG GTTGTGTTAA ATTGAAAGCG AGAAATAATC ATAAATTATT TCATTATCGC
                                 ⇒ Hendra F (protein sequnce SEQ ID NO:6)
EcoRV                            M  A   T  Q  E  V   R  L  K   C  L  L
GATATCCGTT AAGTTTGTAT CGTAATGGCC ACCCAGGAGG TGCGCCTGAA GTGCCTGCTG
```

Figure 11H

```
          C  G  I  I  V  L  V    L  S  L    E  G  L  G    I  L  H    Y  E  K
         TGTGGCATCA TCGTGCTGGT GCTGAGCCTG GAGGGACTGG GAATCCTGCA CTACGAAAAA
          L  S  K  I    G  L  V    K  G  I    T  R  K  Y  K  I  K    S  N  P
         CTGTCCAAGA TCGGCCTGGT GAAGGGGATC ACCCGGAAGT ATAAAATCAA GAGCAATCCC
          L  T  K  D    I  V  I    K  M  I    P  N  V  S    N  V  S    K  C  T
         CTGACAAAGG ACATCGTGAT CAAAATGATC CCTAATGTGA GCAACGTGTC CAAGTGCACC
          G  T  V  M    E  N  Y    K  S  R    L  T  G  I  L  S  P    I  K  G
         GGCACAGTGA TGGAGAACTA CAAATCTAGG CTGACCGGTA TCCTGAGCCC TATCAAGGGA
          A  I  E  L    Y  N  N    N  T  H    D  L  V  G    D  V  K    L  A  G
         GCCATCGAAC TGTATAACAA TAACACACAT GACCTGGTGG GCGATGTGAA ACTGGCCGGG
          V  V  M  A    G  I  A    I  G  I    A  T  A  A    Q  I  T    A  G  V
         GTGGTCATGG CCGGAATCGC TATCGGCATC GCTACCGCTG CTCAGATCAC AGCTGGAGTG
          A  L  Y  E    A  M  K    N  A  D    N  I  N  K    L  K  S    S  I  E
         GCTCTGTACG AGGCCATGAA GAATGCTGAC AATATCAACA AACTGAAGAG CTCCATCGAG
          S  T  N  E    A  V  V    K  L  Q    E  T  A  E    K  T  V    Y  V  L
         TCCACCAACG AAGCCGTGGT GAAGCTGCAG GAGACCGCTG AAAAAACAGT GTACGTGCTG
          T  A  L  Q    D  Y  I    N  T  N    L  V  P  T    I  D  Q    I  S  C
         ACAGCCCTGC AGGACTATAT CAATACCAAC CTGGTGCCAA CAATCGATCA GATCAGCTGT
          K  Q  T  E    L  A  L    D  L  A    L  S  K  Y    L  S  D    L  L  F
         AAGCAGACCG AACTGGCCCT GGACCTGGCT CTGTCTAAAT ACCTGAGCGA TCTGCTGTTC
          V  F  G  P    N  L  Q    D  P  V    S  N  S  M    T  I  Q    A  I  S
         GTGTTTGGCC CAAATCTGCA GGATCCCGTG TCCAACTCTA TGACCATCCA GGCCATCTCC
          Q  A  F  G    G  N  Y    E  T  L    L  R  T  L    G  Y  A    T  E  D
         CAGGCTTTCG GCGGGAACTA CGAGACCCTG CTGAGGACAC TGGGGTATGC CACCGAGGAC
          F  D  D  L    L  E  S    D  S  I    A  G  Q  I    V  Y  V    D  L  S
         TTTGACGATC TGCTGGAAAG CGATTCCATC GCTGGACAGA TCGTGTACGT GGACCTGTCT
          S  Y  Y  I    I  V  R    V  Y  F    P  I  L  T    E  I  Q    Q  A  Y
         AGCTACTATA TCATCGTGAG AGTGTACTTC CCAATCCTGA CCGAGATCCA GCAGGCCTAT
          V  Q  E  L    L  P  V    S  F  N    N  D  N  S    E  W  I    S  I  V
         GTGCAGGAAC TGCTGCCCGT GAGCTTCAAT AACGATAATT CCGAGTGGAT CTCTATCGTG

P  N  F  V    L  I  R    N  T  L    I  S  N  I    E  V  K    Y  C  L
         CCTAACTTTG TGCTGATCCG CAATACCCTG ATCTCTAACA TCGAAGTGAA GTACTGCCTG
          I  T  K  K    S  V  I    C  N  Q    D  Y  A  T    P  M  T    A  S  V
         ATCACAAAGA AAAGCGTGAT CTGTAACCAG GACTATGCCA CCCCCATGAC AGCTAGCGTG
          R  E  C  L    T  G  S    T  D  K    C  P  R  E    L  V  V    S  S  H
         CGGGAGTGCC TGACCGGATC CACCGATAAG TGTCCTAGGG AACTGGTGGT GTCCTCTCAC
          V  P  R  F    A  L  S    G  G  V    L  F  A  N    C  I  S    V  T  C
         GTGCCAAGAT TCGCCCTGTC TGGAGGCGTG CTGTTTGCTA ACTGCATCAG CGTGACCTGC
          Q  C  Q  T    T  G  R    A  I  S    Q  S  G  E    Q  T  L    L  M  I
         CAGTGTCAGA CCACAGGCAG AGCCATCTCT CAGAGCGGGG AGCAGACACT GCTGATGATC
          D  N  T  T    C  T  T    V  V  L    G  N  I  I    I  S  L    G  K  Y
         GACAATACCA CATGTACCAC AGTGGTGCTG GGCAACATCA TCATCTCCCT GGGGAAGTAC
          L  G  S  I    N  Y  N    S  E  S    I  A  V  G    P  P  V    Y  T  D
         CTGGGATCTA TCAATTATAA CTCCGAATCT ATCGCCGTGG GGCCCCCTGT GTACACCGAC
          K  V  D  I    S  S  Q    I  S  S    M  N  Q  S    L  Q  Q    S  K  D
         AAAGTGGACA TCAGCAGCCA GATCTCTAGC ATGAATCAGA GCCTGCAGCA GTCCAAAGAC
          Y  I  K  E    A  Q  K    I  L  D    T  V  N  P    S  L  I    S  M  L
         TATATCAAGG AGGCCCAGAA AATCCTGGAT ACCGTGAACC CATCTCTGAT CAGCATGCTG
          S  M  I  I    L  Y  V    L  S  I    A  A  L  C    I  G  L    I  T  F
         TCCATGATCA TCCTGTACGT GCTGTCCATC GCCGCTCTGT GCATCGGACT GATCACCTTC
          I  S  F  V    I  V  E    K  K  R    G  N  Y  S    R  L  D    D  R  Q
         ATCAGCTTTG TGATCGTGGA GAAGAAACGC GGCAATTACT CCCGGCTGGA CGATAGGCAG
          V  R  P  V    S  N  G    D  L  Y    Y  I  G  T    *            KpnI
         GTGAGACCCG TGTCTAACGG AGACCTGTAC TATATCGGCA CCTGATTTTT ATGGTACCCT
                                                                    => CSL
         CGAGTCTAGA ATCGATCCCG GGTTTTTATG ACTAGTTAAT CACGGCCGCT TATAAAGATC
         TAAAATGCAT AATTTCTAAA TAATGAAAAA AAGTACATCA TGAGCAACGC GTTAGTATAT
         TTTACAATGG AGATTAACGC TCTATACCGT TCTATGTTTA TTGATTCAGA TGATGTTTTA
         GAAAAGAAG TTATTGAATA TGAAAACTTT AATGAAGATG AAGATGACGA CGATGATTAT
         TGTTGTAAAT CTGTTTTAGA TGAAGAAGAT GACGCGTAAA AGTATACTAT GGTTACAAAG
         TATAAGTCTA TACTACTAAT GGCGACTTGT GCAAGAAGGT ATAGTATAGT GAAAATGTTG
         TTAGATTATG ATTATGAAAA ACCAAATAAA TCAGATCCAT ATCTAAAGGT ATCTCTTTG
         CACATAATTT CATCTATTCC TAGTTTAGAA TACCTGCAGC CAAGCTTGGC ACTGGCCGTC
         GTTTTAC
         <- M13F
```

Figure 11I

SEQ ID NO:19   Nipah F gene

```
atggtag
ttatacttga caagagatgt tattgtaatc ttttaatatt gattttgatg atctcggagt
gtagtgttgg gattctacat tatgagaaat tgagtaaaat tggacttgtc aaaggagtaa
caagaaaata caagattaaa agcaatcctc tcacaaaaga cattgttata aaaatgattc
cgaatgtgtc gaacatgtct cagtgcacag ggagtgtcat ggaaaattat aaaacacgat
taaacggtat cttaacacct ataaagggag cgttagagat ctacaaaaac aacactcatg
accttgtcgg tgatgtgaga ttagccggag ttataatggc aggagttgct attgggattg
caaccgcagc tcaaatcact gcaggtgtag cactatatga ggcaatgaag aatgctgaca
acatcaacaa actcaaaagc agcattgaat caactaatga agctgtcgtt aaacttcaag
agactgcaga aaagacagtc tatgtgctga ctgctctaca ggattacatt aatactaatt
tagtaccgac aattgacaag ataagctgca aacagacaga actctcacta gatctggcat
tatcaaagta cctctctgat ttgcttttg tatttggccc caaccttcaa gacccagttt
ctaattcaat gactatacag gctatatctc aggcattcgg tggaaattat gaaacactgc
taagaacatt gggttacgct acagaagact tgatgatct tctagaaagt gacagcataa
caggtcaaat catctatgtt gatctaagta gctactatat aattgtcagg gtttattttc
ctattctgac tgaaattcaa caggcctata tccaagagtt gttaccagtg agcttcaaca
atgataattc agaatggatc agtattgtcc caaatttcat attggtaagg aatacattaa
tatcaaatat agagattgga ttttgcctaa ttacaaagag gagcgtgatc tgcaaccaag
attatgccac acctatgacc aacaacatga gagaatgttt aacgggatcg actgagaagt
gtcctcgaga gctggttgtt tcatcacatg ttcccagatt tgcactatct aacggggttc
tgtttgccaa ttgcataagt gttacatgtc agtgtcaaac aacaggcagg caatctcac
aatcaggaga acaaactctg ctgatgattg acaacaccac ctgtcctaca gccgtactcg
gtaatgtgat tatcagctta gggaaatatc tggggtcagt aaattataat tctgaaggca
ttgctatcgg tcctccagtc tttacagata aagttgatat atcaagtcag atatccagca
tgaatcagtc cttacaacag tctaaggact atatcaaaga ggctcaacga ctccttgata
ctgttaatcc atcattaata agcatgttgt ctatgatcat actgtatgta ttatcgatcg
catcgttgtg tataggggttg attacattta tcagttttat cattgttgag aaaagagaa
acacctacag cagattagag gataggagag tcagacctac aagcagtggg gatctctact
acattgggac atag
```

SEQ ID NO:20   Nipah F protein

```
MVVILDKRCYCNLLILILMISECSVGILHYEKLSKIGLVKGVTRKYKIKSNPLTKDIVIKMIPNVSNMSQCTGSVMENYKTRLNGILTP
IKGALEIYKNNTHDLVGDVRLAGVIMAGVAIGIATAAQITAGVALYEAMKNADNINKLKSSIESTNEAVVKLQETAEKTVYVLTALQDY
INTNLVPTIDKISCKQTELSLDLALSKYLSDLLFVFGPNLQDPVSNSMTIQAISQAFGGNYETLLRTLGYATEDFDDLLESDSITGQII
YVDLSSYYIIVRVYFPILTEIQQAYIQELLPVSFNNDNSEWISIVPNFILVRNTLISNIEIGFCLITKRSVICNQDYATPMTNNMRECL
TGSTEKCPRELVVSSHVPRFALSNGVLFANCISVTCQCQTTGRAISQSGEQTLLMIDNTTCPTAVLGNVIISLGKYLGSVNYNSEGIAI
GPPVFTDKVDISSQISSMNQSLQQSKDYIKEAQRLLDTVNPSLISMLSMIILYVLSIASLCIGLITFISFIIVEKKRNTYSRLEDRRVR
PTSSGDLYYIGT
```

SEQ ID NO:21   Nipah G gene

```
       atgccggc agaaaacaag aaagttagat tcgaaaatac tacttcagac aaagggaaaa
ttcctagtaa agttattaag agctactacg gaaccatgga cattaagaaa ataaatgaag
gattattgga cagcaaaata ttaagtgctt tcaacacagt aatagcattg ctggatcta
tcgtgatcat agtgatgaat ataatgatca tccaaaatta cacaagatca acagacaatc
aggccgtgat caaagatgcg ttgcagggta tccaacagca gatcaaaggg cttgctgaca
aaatcggcac agagataggg cccaaagtat cactgattga cacatccagt accattacta
tcccagctaa cattgggctg ttaggttcaa agatcagcca gtcgactgca agtataaatg
agaatgtgaa tgaaaaatgc aaattcacac tgcctccctt gaaaatccac gaatgtaaca
tttcttgtcc taacccactc ccttttagag agtataggcc acagacagaa ggggtgagca
```

Figure 11J

```
atctagtagg attacctaat aatatttgcc tgcaaaagac atctaatcag atattgaagc
caaagctgat ttcatacact ttacccgtag tcggtcaaag tggtacctgt atcacagacc
cattgctggc tatggacgag ggctattttg catatagcca cctggaaaga atcggatcat
gttcaagagg ggtctccaaa caaagaataa taggagttgg agaggtacta gacagaggtg
atgaagttcc ttctttattt atgaccaatg tctggacccc accaaatcca aacaccgttt
accactgtag tgctgtatac aacaatgaat tctattatgt actttgtgca gtgtcaactg
ttggagaccc tattctgaat agcacctact ggtccggatc tctaatgatg acccgtctag
ctgtgaaacc caagagtaat ggtggggtt acaatcaaca tcaacttgcc ctacgaagta
tcgagaaagg gaggtatgat aaagttatgc cgtatggacc ttcaggcatc aaacagggtg
acaccctgta ttttcctgct gtaggatttt tggtcaggac agagtttaaa tacaatgatt
caaattgtcc catcacgaag tgtcaataca gtaaacctga aaattgcagg ctatctatgg
ggattagacc aaacagccat tatatccttc gatctggact attaaaatac aatctatcag
atggggagaa ccccaaagtt gtattcattg aaatatctga tcaaagatta tctattggat
ctcctagcaa aatctatgat tctttgggtc aacctgtttt ctaccaagcg tcattttcat
gggatactat gattaaattt ggagatgttc taacagtcaa ccctctggtt gtcaattggc
gtaataacac ggtaatatca agacccgggc aatcacaatg ccctagattc aatacatgtc
cagagatctg ctgggaagga gtttataatg atgcattcct aattgacaga atcaattgga
taagcgcggg tgtattcctt gacagcaatc agaccgcaga aaatcctgtt tttactgtat
tcaaagataa tgaaatactt tatagggcac aactggcttc tgaggacacc aatgcacaaa
aaacaataac taattgtttt ctcttgaaga ataagatttg gtgcatatca ttggttgaga
tatatgacac aggagacaat gtcataagac ccaaactatt cgcggttaag ataccagagc
aatgtacata a
```

SEQ ID NO:22   Nipah G protein
MPAENKKVRFENTTSDKGKIPSKVIKSYYGTMDIKKINEGLLDSKILSAFNTVIALLGSIVIIVMNIMIIQNYTRSTDNQAVIKDALQG
IQQQIKGLADKIGTEIGPKVSLIDTSSTITIPANIGLLGSKISQSTASINENVNEKCKFTLPPLKIHECNISCPNPLPFREYRPQTEGV
SNLVGLPNNICLQKTSNQILKPKLISYTLPVVGQSGTCITDPLLAMDEGYFAYSHLEPIGSCSRGVSKQRIIGVGEVLDRGDEVPSLFM
TNVWTPPNPNTVYHCSAVYNNEFYYVLCAVSTVGDPILNSTYWSGSLMMTRLAVKPKSNGGGYNQHQLALRSIEKGRYDKVMPYGPSGI
KQGDTLYFPAVGFLVRTEFKYNDSNCPITKCQYSKPENCRLSMGIRPNSHYILRSGLLKYNLSDGENPKVVFIEISDQRLSIGSPSKIY
DSLGQPVFYQASFSWDTMIKFGDVLTVNPLVVNWRNNTVISRPGQSQCPRFNTCPEICWEGVYNDAFLIDRINWISAGVFLDSNQTAEN
PVFTVFKDNEILYRAQLASEDTNAQKTITNCFLLKNKIWCISLVEIYDTGDNVIRPKLFAVKIPEQCT

Figure 12A

| | | 1 | 50 |
|---|---|---|---|
| AAB39505 | (1) | | TRKYKIKS |
| AAV80428 | (1) | MVVILDRCYCNLL...SECS...GILHYEKLSKIGLVKG | TRKYKIKS |
| NP_112026 | (1) | MVVILDRCYCNLL...SECS...GILHYEKLSKIGLVKG | TRKYKIKS |
| AEQ38114 | (1) | | TRKYKIKS |
| AEB21197 | (1) | | TRKYKIKS |
| SEQ ID NO:6 | (1) | | TRKYKIKS |

| | | 51 | 100 |
|---|---|---|---|
| AAB39505 | (51) | NPLTKDIVIKMIPNVSM.KCTG.VMENYK.KL.IL.PIKGA..YKNN | |
| AAV80428 | (51) | NPLTKDIVIKMIPNVSM.GQCTG.VMENYK.RLNGIL.PIKGA..YKNN | |
| NP_112026 | (51) | NPLTKDIVIKMIPNVSM.GQCTG.VMENYK.RLNGIL.PIKGA..YKNN | |
| AEQ38114 | (51) | NPLTKDIVIKMIPNVSM.KCTG.VMENYK.RL.IL.PIKGA..YKNN | |
| AEB21197 | (51) | NPLTKDIVIKMIPNVSM.KCTG.VMENYK.RL.IL.PIKGA..YKNN | |
| SEQ ID NO:6 | (51) | NPLTKDIVIKMIPNVSM.KCTG.VMENYK.RL.IL.PIKGA..YKNN | |

| | | 101 | 150 |
|---|---|---|---|
| AAB39505 | (101) | THDLVGDV.LAGV.MAG.AIGIATAAQITAGVALYEAMKNADNINKLKSS | |
| AAV80428 | (101) | THDLVGDV.LAGV.MAG.AIGIATAAQITAGVALYEAMSNADNINKLKSS | |
| NP_112026 | (101) | THDLVGDV.LAGV.MAG.AIGIATAAQITAGVALYEAMKNADNINKLKSS | |
| AEQ38114 | (101) | THDLVGDV.LAGV.MAG.AIGIATAAQITAGVALYEAMKNADNINKLKSS | |
| AEB21197 | (101) | THDLVGDV.LAGV.MAG.AIGIATAAQITAGVALYEAMSNADNINKLKSS | |
| SEQ ID NO:6 | (101) | THDLVGDV.LAGV.MAG.AIGIATAAQITAGVALYEAMKNADNINKLKSS | |

| | | 151 | 200 |
|---|---|---|---|
| AAB39505 | (151) | IESTNEAVVKLQETAEKTVYVLTALQDYINTNLVFTID.ISCKQTEL.LD | |
| AAV80428 | (151) | IESTNEAVVKLQETAEKTVYVLTALQDYINTNLVFTIDKISCKQTEL.LD | |
| NP_112026 | (151) | IESTNEAVVKLQETAERTVYVLTALQDYINTNLVFTIDKISCKQTEL.LD | |
| AEQ38114 | (151) | IESTNEAVVKLQETAEKTVYVLTALQDYINTNLVFTID.ISCKQTEL.LD | |
| AEB21197 | (151) | IESTNEAVVKLQETAEKTVYVLTALQDYINTNLVFTID.ISCKQTEL.LD | |
| SEQ ID NO:6 | (151) | IESTNEAVVKLQETAEKTVYVLTALQDYINTNLVFTID.ISCKQTEL.LD | |

| | | 201 | 250 |
|---|---|---|---|
| AAB39505 | (201) | LALSKYL-L.CSC.GPRLQDPVSNSMTIQAISQAFGGNYETLLRTLGYAT | |
| AAV80428 | (201) | LALSKYL....GPNLQDPVSNSMTIQAISQAFGGNYETLLKTLGYAT | |
| NP_112026 | (201) | LALSKYL....GPNLQDPVSNSMTIQAISQAFGGNYETLLRTLGYAT | |
| AEQ38114 | (201) | LALSKYL....GPRLQDPVSNSMTIQAISQAFGGNYETLLRTLGYAT | |
| AEB21197 | (201) | LALSKYL....GPNLQDPVSNSMTIQAISQAFGGNYETLLRTLGYAT | |
| SEQ ID NO:6 | (201) | LALSKYL....GPNLQDPVSNSMTIQAISQAFGGNYETLLRTLGYAT | |

| | | 251 | 300 |
|---|---|---|---|
| AAB39505 | (250) | EDFDDLLESDSI.GQI.YVDLSSYYIIVRVYFPILTEIQQAY.ELLPVS | |
| AAV80428 | (251) | EDFDDLLESDSI.GQI.YVDLSSYYIIVRVYFPILTEIQQAY.ELLPVS | |
| NP_112026 | (251) | EDFDDLLESDSI.GQI.YVDLSSYYIIVRVYFPILTEIQQAY.ELLPVS | |
| AEQ38114 | (251) | EDFDDLLESDSI.GQI.YVDLSSYYIIVRVYFPILTEIQQAY.ELLPVS | |
| AEB21197 | (251) | EDFDDLLESDG.GQI.YVDLSSYYIIVRVYFPILTEIQQAY.ELLPVS | |
| SEQ ID NO:6 | (251) | EDFDDLLESDSIAGQI.YVDLSSYYIIVRVYFPILTEIQQAY.ELLPVS | |

| | | 301 | 350 |
|---|---|---|---|
| AAB39505 | (300) | FNNDNSEWISIVPNF...RNTLISNIE..CLITK.SVICNQDYATPMT | |
| AAV80428 | (301) | FNNDNSEWISIVPNF...RNTLISNIEG.CLITR.SVICNQDYATPMIN | |
| NP_112026 | (301) | FNNDNSEWISIVPNF...RNTLISNIEG.CLITR.SVICNQDYATPMIN | |
| AEQ38114 | (301) | FNNDNSEWISIVPNF...RNTLISNIE..CLITR.SVICNQDYATPMT | |
| AEB21197 | (301) | FNNDNSEWISIVPNF...RNTLISNIE..CLITR.SVICNQDYATPMT | |
| SEQ ID NO:6 | (301) | FNNDNSEWISIVPNF...RNTLISNIE..CLITR.SVICNQDYATPMT | |

Figure 12B

```
                    351                                              400
AAB39505   (350)  ▓RECLTGST▓KCPRELVVSSHVPRFALS▓GVLFANCISVTCQCQTTGRA
AAV80428   (351)  N▓RECLTGST▓KCPRELVVSSHVPRFALSNGVLFANCISVTCQCQTTGRA
NP_112026  (351)  N▓RECLTGST▓KCPRELVVSSHVPRFALSNGVLFANCISVTCQCQTTGRA
AEQ38114   (351)  ▓▓RECLTGST▓KCPRELVVSSHVPRFALS▓GVLFANCISVTCQCQTTGRA
AEB21197   (351)  ▓▓RECLTGST▓KCPRELVVSSHVPRFALS▓GVLFANCISVTCQCQTTGRA
SEQ ID NO:6 (351) ▓▓RECLTGST▓KCPRELVVSSHVPRFALS▓GVLFANCISVTCQCQTTGRA 401                                              450
AAB39505   (400)  ISQSREQTLLMIDNTTC▓▓VLGN▓ISLPKYIGS▓KL▓VLR▓L▓KHQS
AAV80428   (401)  ISQS▓EQTLLMIDNTTCPTAVLGN▓ISL▓KYIGS▓▓▓▓-G▓▓▓
NP_112026  (401)  ISQS▓EQTLLMIDNTTCPTAVLGN▓ISL▓KYIGS▓▓▓▓-G▓▓▓
AEQ38114   (401)  ISQS▓EQTLLMIDNTTC▓▓VLGN▓ISL▓KYIGS▓▓▓▓-▓▓▓▓
AEB21197   (401)  ISQS▓EQTLLMIDNTTC▓▓VLGN▓ISL▓KYIGS▓▓▓▓-▓▓▓▓
SEQ ID NO:6 (401) ISQS▓EQTLLMIDNTTC▓▓VLGN▓ISL▓KYIGS▓▓▓▓-▓▓▓▓

451                                              500
AAB39505   (450)  IQTKVDISSQISSMNQSLQQSKDYIKEAQ▓LDTVNPSLISMLSMIILYV
AAV80428   (450)  ▓▓KVDISSQISSMNQSLQQSKDYIKEAQ▓LDTVNPSLISMLSMIILYV
NP_112026  (450)  ▓▓KVDISSQISSMNQSLQQSKDYIKEAQ▓LDTVNPSLISMLSMIILYV
AEQ38114   (450)  ▓▓KVDISSQISSMNQSLQQSKDYIKEAQ▓LDTVNPSLISMLSMIILYV
AEB21197   (450)  ▓▓KVDISSQISSMNQSLQQSKDYIKEAQ▓LDTVNPSLISMLSMIILYV
SEQ ID NO:6 (450) ▓▓KVDISSQISSMNQSLQQSKDYIKEAQ▓LDTVNPSLISMLSMIILYV 501                                              550
AAB39505   (500)  LSIA▓LCIGLITFISR▓IVEKK▓▓YSRL▓DR▓VRP▓S▓GDLYYIGT---
AAV80428   (500)  LSIA▓LCIGLITFISR▓IVEKKSNTYSRL▓DRKVRPTSSGDLYYIGTDTY
NP_112026  (500)  LSIA▓LCIGLITFISR▓IVEKKSNTYSRL▓DRKVRPTSSGDLYYIGT---
AEQ38114   (500)  LSIA▓LCIGLITFISR▓IVEKK▓▓YSRL▓DR▓VRP▓S▓GDLYYIGT---
AEB21197   (500)  LSIA▓LCIGLITFISR▓IVEKK▓▓YSRL▓DR▓VRP▓S▓GDLYYIGT---
SEQ ID NO:6 (500) LSIA▓LCIGLITFISR▓IVEKK▓▓YSRL▓DR▓VRP▓S▓GDLYYIGT---

551
AAB39505   (547)  ---
AAV80428   (550)  RYI
NP_112026  (547)  ---
AEQ38114   (547)  ---
AEB21197   (547)  ---
SEQ ID NO:6 (547) ---
```

AAB39505: SEQ ID NO:23;   AAV80428: SEQ ID NO:24;
NP_112026: SEQ ID NO:25;   AEQ38114: SEQ ID NO:26;
AEB21197: SEQ ID NO:27;

| SEQ ID NO: | 6 | 23 | 24 | 25 | 26 | 27 |
|---|---|---|---|---|---|---|
| 6 | 100% | 96% | 93% | 94% | 99% | 99% |
| 23 | | 100% | 90% | 91% | 96% | 96% |
| 24 | | | 100% | 98% | 93% | 93% |
| 25 | | | | 100% | 94% | 94% |
| 26 | | | | | 100% | 99% |
| 27 | | | | | | 100% |

Figure 12C

```
                    1                                                    50
AAV80425      (1)   MGPA NKKVRFENTTSLEGKIPSAVIKSYYGTMDIKKIN GLLDSKILSA
SEQ ID NO:3   (1)   --MA SK V  P NN  SG K  K   KVIK YYGTMDIKKIN GLLDSKIL A
AEB21216      (1)   - MA SK V  P NN  SG K  K   KVIK YYGTMDIKKIN GLLDSKIL A
AEB21206      (1)   - MA SK V  P NN  SG K  K   KVIK YYGTMDIKKIN GLLDSKIL A
AAV80426      (1)   - MA SK V  P NN  SG K  K   KVIK YYGTMDIKKIN GLLDSKIL A
AEQ38108      (1)   - MA SK V  P NN  SG K  K   KVIK YYGTMDIKKIN GLLDSKIL A
AEQ38115      (1)   - MA SK V  P NN  SG K  K   KVIK YYGTMDIKKIN GLLDSKIL A 51                                                   100
AAV80425      (51)  FNTVIALLGSI  IVNNIMIIQNYTR TDNQA IK LQG QQQIK LAD
SEQ ID NO:3   (49)  FNTVIALLGSI  IVNNIMIIQNYTR TDNQA IK LQ  QQQIN I D
AEB21216      (50)  FNTVIALLGSI  IVNNIMIIQNYTR TDNQA IK LQ  QQQIK I D
AEB21206      (50)  FNTVIALLGSI  IVNNIMIIQNYTR TDNQA IK LQ  QQQIK I D
AAV80426      (50)  FNTVIALLGSI  IVNNIMIIQNYTR TDNQA IK LQ  QQQIK I D
AEQ38108      (50)  FNTVIALLGSI  IVNNIMIIQNY R TDNQA IK LQ  QQQIK I D
AEQ38115      (50)  FNTVIALLGSI  IVNNIMIIQNYTR TDNQA IK LQ  QQQIK I D 101                                                  150
AAV80425      (101) KIGTEIGPKVSLIDTSSTITIPANIGLLGSKISQ T SINENVN KCKFT
SEQ ID NO:3   (99)  KIGTEIGPKVSLIDTSSTITIPANIGLLGSKISQ T SINENVN KCKFT
AEB21216      (100) KIGTEIGPKVSLIDTSSTITIPANIGLLGSKISQ T SINENVN KCKFT
AEB21206      (100) KIGTEIGPKVSLIDTSSTITIPANIGLLGSKISQ T SINENVN KCKFT
AAV80426      (100) KIGTEIGPKVSLIDTSSTITIPANIGLLGSKISQCT SINENVN KCKFT
AEQ38108      (100) KIGTEIGPKVSLIDTSSTITIPANIGLLGSKISQ T SINENVN KCKFT
AEQ38115      (100) KIGTEIGPKVSLIDTSSTITIPANIGLLGSKISQ T SINENVN KCKFT 151                                                  200
AAV80425      (151) LPPLKIHECNISCPNPLPFKEYRPQ EGVSNLVGLPN ICLQKT NQILK
SEQ ID NO:3   (149) LPPLKIHECNISCPNPLPFKEYRP  GVS LVGLPN ICLQKT  ILK
AEB21216      (150) LPPLKIHECNISCPNPLPFKEYRP  GVS LVGLPN ICLQKT  ILK
AEB21206      (150) LPPLKIHECNISCPNPLPFKEYRP  GVS LVGLPN ICLQKT  ILK
AAV80426      (150) LPPLKIHECNISCPNPLPFKEYRP  GVS LVGLPN ICLQKT  ILK
AEQ38108      (150) LPPLKIHECNISCPNPLPFKEYRP  GVS LVGLPN ICLQKT  ILK
AEQ38115      (150) LPPLKIHECNISCPNPLPFKEYRP  GVS LVGLPN ICLQKT  ILK 201                                                  250
AAV80425      (201) P LISYTL  VGQSGTCITDPLLA  EG  AYSHLE IGSC PG KQRI
SEQ ID NO:3   (199) P LISYTLP        CITDPLLA  G   AYSHLE IGSC RG  KQRI
AEB21216      (200) P LISYTLP        CITDPLLA  G   AYSHLE IGSC RG  KQRI
AEB21206      (200) P LISYTLP        CITDPLLA  G   AYSHLE IGSC RG  KQRI
AAV80426      (200) P LISYTLP        CITDPLLA  G   AYSHLE IGSC RG  KQRI
AEQ38108      (200) P LISYTLP        CITDPLLA  G   AYSHLE IGSC RG  KQRI
AEQ38115      (200) P LISYTLP        CITDPLLA  G   AYSHLE IGSC RG  KQRI 251                                                  300
AAV80425      (251) IGVGEVLDRGDEVPS PNTNVWTPPRPNT  CS VYNN FYYVLCRVST
SEQ ID NO:3   (249) IGVGEVLDRG  VPS PNTNVWTPPNP   CS  Y N  FYY LCAVS
AEB21216      (250) IGVGEVLDRG  VPS PNTNVWTPPNP   CS  Y N  FYY LCAVS
AEB21206      (250) IGVGEVLDRG  VPS PNTNVWTPPNP   CS  Y N  FYY LCAVS
AAV80426      (250) IGVGEVLDRG  VPS PNTNVWTPPNP   CS  Y N  FYY LCAVS
AEQ38108      (250) IGVGEVLDRG  VPS PNTNVWTPPNP   CS  Y N  FYY LCAVS
AEQ38115      (250) IGVGEVLDRG  VPS PNTNVWTPPNP   CS  Y N  FYY LCAVS
```

Figure 12D

```
              301                                              350
AAV80425   (301) VGDPILNSTYW GSEM TRLAV FFSNGGGYNQHQ  RS    YDKVM
SEQ ID NO:3(299) VGDPILNST W  SL   RLAV PKS  G YNQ       G YDKVM
AEB21216   (300) VGDPILNST W  SL   RLAV PKS  G YNQ       G YDKVM
AEB21206   (300) VGDPILNST W  SL   RLAV PKS  G NYQ       G YDKVM
AAV80426   (300) VGDPILNST W  SL   RLAV PKS  G YNQ       G YDKVM
AEQ38108   (300) VGDPILNST W  SL   RLAV PKS  G YNQ       G YDKVM
AEQ38115   (300) VGDPILNST W  SL   RLAV PKS NG YNQ       G YDKVM 351                                              400
AAV80425   (351) PYGPSGIKQGD TLYFPAVGFLVRTEF KYNDSNCPITKQQYSKPENCRLSM
SEQ ID NO:3(349) PYGPSGIKQGD TLYFPAVG L  TEF YNDSNCPI  C YSK ENCRLSM
AEB21216   (350) PYGPSGIKQGD TLYFPAVG L  TEF YNDSNCPI  C YSK ENCRLSM
AEB21206   (350) PYGPSGIKQGD TLYFPAVG L  TEF YNDSNCPI  C YSK ENCRLSM
AAV80426   (350) PYGPSGIKQGD TLYFPAVG L  TEF YNDSNCPI  C YSK ENCRLSM
AEQ38108   (350) PYGPSGIKQGN TLYFPAVG L  TEF YNDSNCPI  C YSK ENCRLSM
AEQ38115   (350) PYGPSGIKQGD TLYFPAVG L  TEF YNDSNCPI  C YSK ENCRLSM 401                                              450
AAV80425   (401) G RPNSHYILRSGLLKYNLSDGENPK VFIEI   RL IGSPSKIYDSLG
SEQ ID NO:3(399) G   SHYILRSGLLKYNL         FIEI  DRL IGSPSKIY SLG
AEB21216   (400) G   SHYILRSGLLKYNL         FIEI  DRL IGSPSKIY SLG
AEB21206   (400) G   SHYILRSGLLKYNL         FIEI  DRL IGSPSKIY SLG
AAV80426   (400) G   SHYILRSGLLKYNL         FIEI  DRL IGSPSKIY SLG
AEQ38108   (400) G   SHYILRSGLLKYNL         FIEI  DRL IGSPSKIY SLG
AEQ38115   (400) G   SHYILRSGLLKYNL         FIEI  DRL IGSPSKIY SLG 451                                              500
AAV80425   (451) QPVFYQAS SWDTMIKFGD LT VNF LV  WRNN VISRPGQSQCPRFNTC
SEQ ID NO:3(449) QPVFYQAS SWDTMIK GD   TV F  V  WRNN VISRPGQSQCPRFN C
AEB21216   (450) QPVFYQAS SWDTMIK GD   TV F  V  WRNN VISRPGQSQCPRFN C
AEB21206   (450) QPVFYQAS SWDTMIK GD   TV F  V  WRNN VISRPGQSQCPRFN C
AAV80426   (450) QPVFYQAS SWDTMIK GD   TV F  V  WRNN VISRPGQSQCPRFN C
AEQ38108   (450) QPVFYQAS SWDTMIK GD   TV F  V  WRNN VISRPGQSQCPRFN C
AEQ38115   (450) QPVFYQAS SWDTMIK GD   TV F  V  WRNN VISRPKGQSQCPRFN C 501                                              550
AAV80425   (501) PE CWEGVYNDAFLIDR  NW  SAGV LDSNQTAENPVFTVFKDNEILYRA
SEQ ID NO:3(499) PE CWEG YNDAFLIDR  NW SAGV L SNQTAENPVF VFKDNEILY
AEB21216   (500) PE CWEG YNDAFLIDR  NW SAGV L SNQTAENPVF VFKDNEILY
AEB21206   (500) PE CWEG YNDAFLIDR  NW SAGV L SNQTAENPVF VFKDNEILY
AAV80426   (500) PE CWEG YNDAFLIDR  NW SAGV L SNQTAENPVF VFKDNEILY
AEQ38108   (500) PE CWEG YNDAFLIDR  NW SAGV L SNQTAENPVF VFKDNEILY
AEQ38115   (500) PE CWEG YNDAFLIDR  NW SAGV L SNQTAENPVF VFKDNEILY 551                                              600
AAV80425   (551) QLAS  DTNAQKTITNCFLLKNKIWCISLVEIYDTG DNVIRPSLFAVKIPE
SEQ ID NO:3(549)  LA  DTNAQKTIT CFLL N IWCISLVEIYDTGD VIRPKLFAVKIP
AEB21216   (550)  LA  DTNAQKTIT CFLL N IWCISLVEIYDTGD VIRPKLFAVKIP
AEB21206   (550)  LA  DTNAQKTIT CFLL N IWCISLVEIYDTGD VIRPKLFAVKIP
AAV80426   (550)  LA  DTNAQKTIT CFLL N IWCISLVEIYDTGD VIRPKLFAVKIP
AEQ38108   (550)  LA  DTNAQKTIT CFLL N IWCISLVEIYDTGD VIRPKLFAVKIP
AEQ38115   (550)  LA  DTNAQKTIT CFLL N IWCISLVEIYDTGD VIRPKLFAVKIP
```

Figure 12E

```
                    601          614
AAV80425     (601)  ▓YPYDVPDYA---
SEQ ID NO:3  (599)  ▓▓-----------
AEB21216     (600)  ▓▓▓----------
AEB21206     (600)  ▓▓▓----------
AAV80426     (600)  ▓▓▓YPYDVPDYA
AEQ38108     (600)  ▓▓▓----------
AEQ38115     (600)  ▓▓▓----------
```

AAV80425: SEQ ID NO:28;   AEB21216: SEQ ID NO:29;
AEB21206: SEQ ID NO:30;   AAV80426: SEQ ID NO:31;
AEQ38108: SEQ ID NO:32;   AEQ38115: SEQ ID NO:33

| SEQ ID NO: | 3 | 28 | 29 | 30 | 31 | 32 | 33 |
|---|---|---|---|---|---|---|---|
| 3 | 100% | 85% | 99% | 99% | 97% | 99% | 99% |
| 28 |  | 100% | 85% | 85% | 86% | 85% | 85% |
| 29 |  |  | 100% | 99% | 99% | 99% | 99% |
| 30 |  |  |  | 100% | 99% | 99% | 99% |
| 31 |  |  |  |  | 100% | 99% | 98% |
| 32 |  |  |  |  |  | 100% | 99% |
| 33 |  |  |  |  |  |  | 100% |

Figure 12F

```
                     1                                                50
SEQ ID NO:1    (1)   ATGATXXCTGATTCCAAATXGXTAAGCXTXAACAAXAATCXATCTXXTAA
SEQ ID NO:2    (1)   ---ATXGCCGACTCCAAGCTGXTGTCTXTGAACAATAACCTGAGCGGCAA 51                                               100
SEQ ID NO:1    (51)  AATCAAGCATCAAGGTAAAGTTATCAAGAATTATTACGGCACAATGGACX
SEQ ID NO:2    (48)  GATCAAAGACCAGGXCAAAGTXGATCAAGAACTACTATGGAXCATXGACX 101                                              150
SEQ ID NO:1    (101) TCAAGAAAATTAAXGATXGGTXATXAGATAGTAAGATACTTGGXGXGTXT
SEQ ID NO:2    (98)  TCAAGAAGATCAACXACXGXACXGCXGGAXTCCAAGATCCTGGXCGXCTXC 151                                              200
SEQ ID NO:1    (151) AACACAGTXATAGXTTXGTTXGGATXAATXATXATXATTGTXGATXAATAX
SEQ ID NO:2    (148) AACACAGTXGATXCGXXCTXGCXGGXCXTATCATXATCATCGXGATGAACAX 201                                              250
SEQ ID NO:1    (201) XATXGATAAXTCAAAAXTTACXACCAGAACGACXTXATAATXCAGGXACTAAXCA
SEQ ID NO:2    (198) XATXGATCAXCCAGAAXTTACXACCAGAACCACXAGACAACCXAGGXCCXTGAXCX 251                                              300
SEQ ID NO:1    (251) AAGAGTXACTCCAGAGTXTXACAXCAACAAAXTCAAAGCTTTAACAGACAAA
SEQ ID NO:2    (248) AGXAGTCTXTGCXAXAGCXGTGCAGCXAGCAGATXAAGXGCTCTGACCXACAAA 301                                              350
SEQ ID NO:1    (301) ATXGGXACAGAAGATAGXCCXCAAAXGXCTCACXAAXTGACACATCXAGXAC
SEQ ID NO:2    (298) ATXGGXACAGAAATXGGACCXCAAGXTGAGCXTGATCXATAXCAGCTCCAX 351                                              400
SEQ ID NO:1    (351) XATXACAATTCCTXGXTAACATAGGGTXACTXGGATXCAAGATAAGTXAGX
SEQ ID NO:2    (348) XATXACAATXCCTXGCXCAACAXCXGGACTGCTGGXCTCCAAAATXCAGCCAGX 401                                              450
SEQ ID NO:1    (401) CTACXAGCAGTATXAATXGAXGAATGXTAAXGATAAATXGCAAAXTTACTCXXT
SEQ ID NO:2    (398) XCACCTCTAGCATCAACXGAGAATXCGAACXGACAAGXTGXAAATTCACACTG 451                                              500
SEQ ID NO:1    (451) XXTCCTTTAAAXGATTCATGXAGTXTAATATCTCTTGTXCXGAATCXTTTGXC
SEQ ID NO:2    (448) XCCXCXCTGAAGATCCACXAGTXGCAACATCAGCTXTXCAAATCCCTGCXC 501                                              550
SEQ ID NO:1    (501) TXTCAGAGAATACCGACXAATCTCAXXAAGXGGXTXAGTXATCTTXTAGXAC
SEQ ID NO:2    (498) TXTTAGGGAATACAGACCCTATCAGCXAGGXAGTGTCCGACCTGGTGGXGAC 551                                              600
SEQ ID NO:1    (551) XGCXGAACXAGATXCTGTCXTACAGAAGACAACXATCAAXAATXTTAAAGCCC
SEQ ID NO:2    (548) XGCCAAACXAGATXCXGTCXTGCXAGAAGACCACATXCACCATCCXGAAACXT 601                                              650
SEQ ID NO:1    (601) AXGGCTXGATAXCCTATACTCXACCAAXTAATACCAGAXGAAGXGGXTTGCAT
SEQ ID NO:2    (598) AXGGCTXGATCTCXTTACACCXGCXCAATCAACACAAGAGAGGGCCTGXGCAT 651                                              700
SEQ ID NO:1    (651) CAXCTGAXXCCACTTTTGGXXTGTXATAATXGCTTXTTCXXCTATAXCCAT
SEQ ID NO:2    (648) CACAGACXCCCTXGCTGGXCCXTGGATAATXGGGTTCTTTGCXTTATAXCCATC 701                                              750
SEQ ID NO:1    (701) TTGAAAXGATXGGATCAXGTACTAGAGGAATTGCAAAACXAAGGATAAXTA
SEQ ID NO:2    (698) XGGAGAAGATCGGATCCXGTACCAGGGCATCGCCAAACAGAGAATCAXC
```

Figure 12G

```
                          751                                           800
SEQ ID NO:1      (751)    GGGGTGGGTGAGGTATTGATAGGGGTGATAAGGTGCCATCAATGTTTAT
SEQ ID NO:2      (748)    GGGGTGGGAGAAGTGCTGGACAGGGGCGATAAGGTGCCAAGCATGTTCAT 801                                           850
SEQ ID NO:1      (801)    ACCCAATGTTTGGACACCACGGCAATGGAAGCACCATCCATCATTGGAGCT
SEQ ID NO:2      (798)    GACCAACGTGTGGACACCACGGCAATCCCTCCACCATCCACCATTGCTCCT 851                                           900
SEQ ID NO:1      (851)    CAACTTACCCATGAAGATTTTTATTACACATTGTGCGCAGTGTCCCATGGG
SEQ ID NO:2      (848)    CTACATACCACGAGGACTTTTACTATACCCTGTGTGCCGTGTCCCATGTG 901                                           950
SEQ ID NO:1      (901)    GGAGATCCTATCCTTAACAGTACTTCCTGGACAGAGTCACTGTCTCTGAT
SEQ ID NO:2      (898)    GGCGATCCAATCCTGAAATCTACCAGCTGGACAGAATCCTGTCTCTGAT 951                                           1000
SEQ ID NO:1      (951)    TCGTCTTGCTGTAAGACCAAAAAGTGATAGTGGAGACTACAATCAGAAAT
SEQ ID NO:2      (948)    CACGCTGGCCCGTGAGACTAAGAGCGACTCCGGCATTACAATCAGAAGT 1001                                          1050
SEQ ID NO:1      (1001)   ACATCGCTATAACTAAAGTTGAAGGAGGGAAGTACGATAAGGTGATGCCT
SEQ ID NO:2      (998)    ATATCGCTATCACCAAAGTGGAGAGGGGAAAGTACGACAAAGTGATGCCA 1051                                          1100
SEQ ID NO:1      (1051)   TACGGTCCATCAGGTATCAAGCAAGGGGATACATTGTACTTTCCGGGCGT
SEQ ID NO:2      (1048)   TATGGGCCCAGCGGAATCAAGCAGGGCGATACCCTGTACTTCCCCGGCGT 1101                                          1150
SEQ ID NO:1      (1101)   CGGTTTTTTGCCAAGGAGCGAATTTCAATATAATGACTCTAATTGTCCCA
SEQ ID NO:2      (1098)   GGGGTTTCTGCCTAGAAAAGAGTTCCAGTACAACGACTCAATTGCCCCA 1151                                          1200
SEQ ID NO:1      (1151)   TAATTCATTGCAAGTACAGCAAAGCACAAAAACTGTAGCCTTTCAATGCGT
SEQ ID NO:2      (1148)   TCATCCACTGTAAGTATTCTAAAGCTGAAAACTGCAGGCTGAGCATGGGA 1201                                          1250
SEQ ID NO:1      (1201)   GTCAACTCCAAAAGTCATTATATTTGAGATCAGGACTATTGAAGTATAA
SEQ ID NO:2      (1198)   GTGAATTCTAAGAGCCATTACATCCTGAGATCCGGCCTGCTGAAATATAA 1251                                          1300
SEQ ID NO:1      (1251)   TCTATCTCTTGGAGGAGACATCATACTCCAATTTATCGAGATTGCTGACA
SEQ ID NO:2      (1248)   CCTGTCTCTGGGCGGGGACATCATCCTGCAGTTCATCGAGATCGCCGATA 1301                                          1350
SEQ ID NO:1      (1301)   ATAGATTGACCATCGGTTCTCCTAGTAAGATATACAATTCCCTAGGTCAA
SEQ ID NO:2      (1298)   ACAGACTGACCATCGGCGTCCCCTCTAAGATCTACAATAGCCTGGGACAG 1351                                          1400
SEQ ID NO:1      (1351)   CCCGTTTTCTACCAGGATCATATTCTTGGATACGATGATTAAATTAGG
SEQ ID NO:2      (1348)   CCTGTGTTTTACCAGGGTAGCTATCCTGGGACACCATGATCAAACTGGG 1401                                          1450
SEQ ID NO:1      (1401)   GGATGTTGATACCGTTGACCCTCTAAGAGTACAGTGGAGAAATAACAGTG
SEQ ID NO:2      (1398)   GGACGTGGATACAGTGGATCCTCTGCCCGTGCAGTGGCGGAATAACTCCG 1451                                          1500
SEQ ID NO:1      (1451)   TGATTTCTAGACTTGGACAGTCACAGTGTCCTCGATTAATGTCTGTCCC
SEQ ID NO:2      (1448)   TGATCTCTAGGCCAGGACAGTCCAGTGTCCCAGATTCAACCTGTGCCCT
```

Figure 12H

```
              1501                                              1550
SEQ ID NO:1  (1501) GAGGTATGCTGCAAGGGACATATAATGATGCTTTTCTAATAGACCGGCT
SEQ ID NO:2  (1498) GAACTGTGTTGGGAAGGCACCTACAACGACGCCTTTCTGATCGATAGGCT 1551                                              1600
SEQ ID NO:1  (1551) AAACTGGGTTAGTGCTGGTGTTTATTAAACAGTAACCAAACTGCAGAGA
SEQ ID NO:2  (1548) GAATTGGGTGTCTGCTGGGTGTATCTGAATAGCAACAGACAGCCGAGA 1601                                              1650
SEQ ID NO:1  (1601) ACCCTGTGTTTCCGTATTCAAGGATAACGAGATCCTTACCAAGTTCCA
SEQ ID NO:2  (1598) ACCCTGTGTCGCTGTGTTAAGGACAATGAGATCCTGTACCAGGTGCCA 1651                                              1700
SEQ ID NO:1  (1651) CTGGCTGAAGATGACACAAATGCACAAAAAACCATCACAGATTGCTTCTT
SEQ ID NO:2  (1648) CTGGCCCAAGACGATACCAACGGTCAGAAAACCATCACAGATTGCTGCT 1701                                              1750
SEQ ID NO:1  (1701) GCTGGAGAATGTCATAGTGGTATAATCACTAGTAGAAATATACGATACAG
SEQ ID NO:2  (1698) GCTGGAGAATGTGATCTGGGTATCGCTGGTGGAAATCTATGACACCG 1751                                              1800
SEQ ID NO:1  (1751) GAGACAGTGTGATAAGGTTAAAACTATTTGCAGTCAAGATACCTGCCGA
SEQ ID NO:2  (1748) GCGATAGCGTGATCAGACTCAAGCTGTTTGCCGGAAAATCCTGCTCAG 1801      1815
SEQ ID NO:1  (1801) TGTTCAAGAGTGA
SEQ ID NO:2  (1798) TGCTCTGAAAGCTGA
```

Sequence identity is 76% between SEQ ID NO:1 and SEQ ID NO:2.

Figure 12I

```
                      1                                                  50
SEQ ID NO:4     (1)   ATGGCTACAACAAGAGGTCAAGCTAAAGTGTTTGCTCTGTGGATCATAGT
SEQ ID NO:5     (1)   ATGGCCACCCAGGAGGTGCGCCTGAAGTGCCTGCTGTGGCATCATCGT 51                                                 100
SEQ ID NO:4    (51)   TCTGGTTTGTCATTAGAAGGGCTAGGGATACTACATTATGAGAAACTTA
SEQ ID NO:5    (51)   GCTGGTGCTGAGCCTGGAGGGACTGGGAATCCTGCACTACGAAAACTGT 101                                                150
SEQ ID NO:4   (101)   GTAAGATAGGGCTGGTAAAGGTATTACAAGAAAGTACAAGATTAAGAGT
SEQ ID NO:5   (101)   CCAAGATCGGCCTGGTGAAGGGGATCACCCGGAGTATAAAATCAAGAGC 151                                                200
SEQ ID NO:4   (151)   AACCCTTTGACCAAGGATATTGTGATCAAAATGATCCCTAATTCTCGAA
SEQ ID NO:5   (151)   AATCCCTGACAAAGGACATCGTGATCAAAATGATCCCTAATTGAGCAA 201                                                250
SEQ ID NO:4   (201)   TGTCTCAAAGTGCACCGGACTGTTATGGAGAATTACAAAGCAGACTCA
SEQ ID NO:5   (201)   CGTGTCCAAGTGCACCGGCACAGTGATGGAGAACTACAAATCTAGCGA 251                                                300
SEQ ID NO:4   (251)   CAGGGATTCCTCAGCAATCAAAGGCGCGATCGAACTGTACAATAATAAC
SEQ ID NO:5   (251)   CCGGGATCCTGAGCCCTATCAAGGGAGCCATCGAACTGTATAACAATAAC 301                                                350
SEQ ID NO:4   (301)   ACGCATGACCTAGTTGGTGATGTCAAGCTTGCAGGTGTGGTGATGGCAGG
SEQ ID NO:5   (301)   ACACATGACCTGGTGGGCGATGTGAAACTGGCCGGGGTGGTCATGGCCGG 351                                                400
SEQ ID NO:4   (351)   GATTCAATCGGATAGCTACTGCTGCACAAATCACAGCAGGTGTTGCCT
SEQ ID NO:5   (351)   AATCCTTAGCGGCATCGCTACCGCTGCTCAGATCACAGCTGAGTGCCTC 401                                                450
SEQ ID NO:4   (401)   TATATGAGGCAATGAAGAACGCAGACAATATCAATAAACTCAAGAGCAGC
SEQ ID NO:5   (401)   TGTACGAGGCCATGAAGAATGCTGACAATATCAACAAACTGAAGAGCTCC 451                                                500
SEQ ID NO:4   (451)   ATAGAGTCTACAAATCAGGCTGTTGTCAAATTACAGGAAACAGCTGAGAA
SEQ ID NO:5   (451)   ATCGAGTCCACCAACCAAGCCGTGGTGAAGCTGCAGGAGACCGCTGAAAA 501                                                550
SEQ ID NO:4   (501)   AACAGTCTACGTCCTTACTGCTCTTCAAGATTACATCAACACTAACCTTG
SEQ ID NO:5   (501)   AACAGTGTACGTGCTGACAGCCCTGCAGGACTATATCAATACCAACCTGG 551                                                600
SEQ ID NO:4   (551)   TTGCTACAATAGATCAAATTAGCTGCAAGCAAACAGAGCTCGTATTAGAC
SEQ ID NO:5   (551)   TGCCAACAATCGATCAGATCAGCTGTAAGCAGACCGAACTGGCCCTGGAC 601                                                650
SEQ ID NO:4   (601)   TTGGGGTTGTCTAAGTATCTGTCTGATCTGCTCTTGTTTTCGACCTAA
SEQ ID NO:5   (601)   CTGGCTCTGTCTAAAATACCTGAGCCATCTGCTGTTCGTGTTGCCCAAA 651                                                700
SEQ ID NO:4   (651)   CTTACAGGATCCAGTCTCTAATTCCATTACTATCCAAGCAATATCTCAAG
SEQ ID NO:5   (651)   TCTGCAGGATCCCTGTCCAACTTTATGACCATCAGGCCATCTCCAGG 701                                                750
SEQ ID NO:4   (701)   CATTTGGGGCAATTACGAAACCTTACTAGAAGCTTGTTACGGACC
SEQ ID NO:5   (701)   CTTTCGGCCTGGAACTACGAGACCCTGCTGACGACACTGGGGTATGCCACC
```

Figure 12J

```
                  751                                              800
SEQ ID NO:4 (751) GAGGACTTCGACGACCTTTTAGAAAGTGATAGCATAGCAGGCCAGATAGT
SEQ ID NO:5 (751) GAGGACTTTGACGATCTGCTGGAAAGCGATTCCATCGGTGGACAGATCGG 801                                              850
SEQ ID NO:4 (801) CTATGTAGATCTCAGTAGCTATTACATAATAGTAAGGGTGTATTTTCCCA
SEQ ID NO:5 (801) GTACCTGGACCTGTCTAGCTACTATATCATCGTGAGATGTACTTCCCAA 851                                              900
SEQ ID NO:4 (851) TACTAACAGAGATCCAACAGGCTTATGTGCAGGAGTTGCTTCCAGTGAGT
SEQ ID NO:5 (851) TCCTGACCGAGATCCAGCAGGCCTATGTGCAGGAACTGCTGCCTGAGC 901                                              950
SEQ ID NO:4 (901) TTAATAACGATAATTCAGAATGGATCAGCATTGTCCGGAATTTCGTGCT
SEQ ID NO:5 (901) TTCAATAACGATAATTCCGAGTGGATCTCTATCGTGCCTAACTTTGTGCT 951                                             1000
SEQ ID NO:4 (951) GATTAGGAACACGGTGATTTCAAATATAGAAGTCAAGTACTGCTTAATCA
SEQ ID NO:5 (951) GATCCGCAATACCGTCATCTCTAACATCGAAGTGAAGTACTGCCTGATCA 1001                                            1050
SEQ ID NO:4 (1001) CCAAGAAAAGTGTGATTTGTAATCAGGACTATGCTACACCATGACGGCT
SEQ ID NO:5 (1001) CAAAGAAAAGCGTGATCTGTAACCAGGACTATGCCACCCCATGACAGCT 1051                                            1100
SEQ ID NO:4 (1051) AGCCTGAGAGAATGCTTGACAGGATCCACAGATAAGTGCCAAGGGAGTT
SEQ ID NO:5 (1051) AGCCGTCCGGCAGTGCCTGACCGGATCCACCGATAAGTGTCCTAGGGAACT 1101                                            1150
SEQ ID NO:4 (1101) AGTAGTCTCATCCATGTTCCAAGATTTGCCCTCTCAGGAGGAGTCTTGT
SEQ ID NO:5 (1101) GGTGGTGTCCTCTCACGTGCCAAGATTCGCCCTGTCTGGAGGCGTGCTGT 1151                                            1200
SEQ ID NO:4 (1151) TTGCAAATTGTATAAGTGTGACATGTCAGTGTCAGACTACTGGGAGGGCA
SEQ ID NO:5 (1151) TTGCTAACTGCATCAGCGTGACCTGCCAGTGTCAGACCACAGGCAGAGCC 1201                                            1250
SEQ ID NO:4 (1201) ATATCTCAATCAGGGGAACAGACACTACTGATGATTCACAATACTACCTG
SEQ ID NO:5 (1201) ATCCTTCAGAGCGGGAGCAGACACTGCTGATGATCCACAATACCACATG 1251                                            1300
SEQ ID NO:4 (1251) CACAACAGTGTTTCTAGCAAAACATAATCATAAGCCTTCCAAAATATTTGG
SEQ ID NO:5 (1251) TACCACAGTGGTGCTGGGCAACATCATCATCTCCCTGGGGAAGTACCTGG 1301                                            1350
SEQ ID NO:4 (1301) GATCAATAAATTACAATTCTGAGAGCATTGCTGTTGGCCACCAGTCTAT
SEQ ID NO:5 (1301) GATCTATCAATTATAACTCCGAATCTATCGCCGTGGGGCCCCTGTGTAC 1351                                            1400
SEQ ID NO:4 (1351) ACAGACAAAGTTGATATTCAAGTCAGATATCTAGTAGAATCAATCACT
SEQ ID NO:5 (1351) ACCGACAAAGTGGACATCAGCAGCCAGATCTCTAGCATGAATCAGAGCCT 1401                                            1450
SEQ ID NO:4 (1401) ACAACAATCTAAGGATTACATTAAAGAAGCTCAAAAGATTTGGACACTG
SEQ ID NO:5 (1401) GCAGCAGTCCAAAGACTATATCAAGGAGGCCCAGAAAATCCTGGATACCG 1451                                            1500
SEQ ID NO:4 (1451) TGAATCCGTGGTTGATAAGTATGCTATCAATGATCCTTTATGTTTG
SEQ ID NO:5 (1451) TGAACCCATCTCCGATCAGCATGCCTGTCCATGATCATCCTGTACGTGCTG
```

Figure 12K

```
                    1501                                              1550
SEQ ID NO:4  (1501) TCCATTGCAGCACTTTGCATTGGTCTGATCACTTTCATAAGTTTTCTAAT
SEQ ID NO:5  (1501) TCCATCGCCGCTCTTGTCCATCGGACTGATCACCTTCATCAGCTTTGTGAT 1551                                              1600
SEQ ID NO:4  (1551) AGTTGAGAAAAGAGAGGAATTACAGCAGGCTAGATGATAGGCAAGTGC
SEQ ID NO:5  (1551) CGTGGAGAAGAAACGCGGCAATTACTCCCGGCTGGACGATAGGCAGGTGA 1601                                1641
SEQ ID NO:4  (1601) AACGGTCAGTAATGGTGATCTGTATTATATTGGAACATAA
SEQ ID NO:5  (1601) CACCCCGGTCAACGGAGACCTGTACTATATCGGCACCGGA
```

Sequence identity is 75% between SEQ ID NO:4 and SEQ ID NO:5.

SEQUENCE LISTING

<160> NUMBER OF SEQ ID NOS: 33

<210> SEQ ID NO 1
<211> LENGTH: 1815
<212> TYPE: DNA
<213> ORGANISM: artificial sequence
<220> FEATURE:
<223> OTHER INFORMATION: Hendra virus wildtype DNA encoding G protien

<400> SEQUENCE: 1

| | |
|---|---|
| atgatggctg attccaaatt ggtaagcctg aacaataatc tatctggtaa aatcaaggat | 60 |
| caaggtaaag ttatcaagaa ttattacggc acaatggaca tcaagaaaat taacgatggg | 120 |
| ttattagata gtaagatact tggggcgttt aacacagtga tagctttgtt gggatcaatc | 180 |
| atcatcattg tgatgaatat catgataatt caaaattaca ccagaacgac tgataatcag | 240 |
| gcactaatca aagagtcact ccagagtgta cagcaacaaa tcaaagcttt aacagacaaa | 300 |
| atcgggacag atataggccc caaagtctca ctaattgaca catccagcac catcacaatt | 360 |
| cctgctaaca tagggttact gggatccaag ataagtcagt ctaccagcag tattaatgag | 420 |
| aatgttaacg ataaatgcaa atttactctt cctccttaa agattcatga gtgtaatatc | 480 |
| tcttgtccga atcctttgcc tttcagagaa taccgaccaa tctcacaagg ggtgagtgat | 540 |
| cttgtaggac tgccgaacca gatctgtcta cagaagacaa catcaacaat cttaaagccc | 600 |
| aggctgatat cctatactct accaattaat accagagaag gggtttgcat cactgaccca | 660 |
| cttttggctg ttgataatgg cttcttcgcc tatagccatc ttgaaaagat cggatcatgt | 720 |
| actagaggaa ttgcaaaaca aaggataata ggggtgggtg aggtattgga taggggtgat | 780 |
| aaggtgccat caatgtttat gaccaatgtt tggacaccac ccaatccaag caccatccat | 840 |
| cattgcagct caacttacca tgaagatttt tattacacat tgtgcgcagt gtcccatgtg | 900 |
| ggagatccta tccttaacag tacttcctgg acagagtcac tgtctctgat tcgtcttgct | 960 |
| gtaagaccaa aaagtgatag tggagactac aatcagaaat acatcgctat aactaaagtt | 1020 |
| gaaagaggga agtacgataa ggtgatgcct tacggtccat caggtatcaa gcaaggggat | 1080 |
| acattgtact ttccggccgt cggttttttg ccaaggaccg aatttcaata taatgactct | 1140 |
| aattgtccca taattcattg caagtacagc aaagcagaaa actgtaggct ttcaatgggt | 1200 |
| gtcaactcca aaagtcatta tattttgaga tcaggactat tgaagtataa tctatctctt | 1260 |
| ggaggagaca tcatactcca atttatcgag attgctgaca atagattgac catcggttct | 1320 |
| cctagtaaga tatacaattc cctaggtcaa cccgttttct accaggcatc atattcttgg | 1380 |
| gatacgatga ttaaattagg cgatgttgat accgttgacc ctctaagagt acagtggaga | 1440 |
| aataacagtg tgatttctag acctggacag tcacagtgtc ctcgatttaa tgtctgtccc | 1500 |
| gaggtatgct gggaagggac atataatgat gcttttctaa tagaccggct aaactgggtt | 1560 |
| agtgctggtg tttattttaaa cagtaaccaa actgcagaga accctgtgtt tgccgtattc | 1620 |
| aaggataacg agatcccttta ccaagttcca ctggctgaag atgacacaaa tgcacaaaaa | 1680 |
| accatcacag attgcttctt gctggagaat gtcatatggt gtatatcact agtagaaata | 1740 |
| tacgatacag gagacagtgt gataaggcca aaactatttg cagtcaagat acctgcccaa | 1800 |
| tgttcagaga gttga | 1815 |

<210> SEQ ID NO 2
<211> LENGTH: 1812
<212> TYPE: DNA
<213> ORGANISM: artificial sequence
<220> FEATURE:
<223> OTHER INFORMATION: codon-optimized DNA encoding Hendra G protein

<400> SEQUENCE: 2

| | |
|---|---|
| atggccgact ccaagctggt gtctctgaac aataacctga gcggcaagat caaagaccag | 60 |
| ggcaaagtga tcaagaacta ctatggaacc atggacatca agaagatcaa cgacggactg | 120 |
| ctggattcca gatcctgggg cgccttcaac acagtgatcg ctctgctggg ctctatcatc | 180 |
| atcatcgtga tgaacatcat gatcatccag aattacacca gaaccacaga caaccaggcc | 240 |

```
ctgatcaagg agtctctgca gagcgtgcag cagcagatca aggctctgac cgacaaaatc    300
gggacagaaa tcggacccaa ggtgagcctg atcgatacca gctccaccat cacaatccct    360
gccaacatcg gactgctggg ctccaaaatc agccagtcca cctctagcat caacgagaat    420
gtgaacgaca agtgcaaatt cacactgccc cctctgaaga tccacgagtg caacatcagc    480
tgtccaaatc ccctgccttt tagggaatac agacctatca gccagggagt gtccgacctg    540
gtgggactgc aaaccagatc tgtctgcag aagaccacat ccaccatcct gaaacctagg     600
ctgatctctt acaccctgcc aatcaacaca agagagggcg tgtgcatcac agacccctg     660
ctggccgtgg ataatgggtt ctttgcttat agccatctgg agaagatcgg atcctgtacc    720
agggcatcg ccaaacagag aatcatcggg gtgggagaag tgctggacag gggcgataag     780
gtgccaagca tgttcatgac caacgtgtgg acaccaccca tccctccac catccaccat     840
tgctcctcta cataccacga ggactttac tataccctgt gtgccgtgtc ccatgtgggc     900
gatccaatcc tgaactctac cagctggaca gaatccctgt ctctgatcag gctggccgtg    960
agacctaaga gcgactccgg ggattacaat cagaagtata tcgctatcac caaagtggag   1020
aggggaaagt acgacaaagt gatgccatat gggcccagcg gaatcaagca gggcgatacc   1080
ctgtacttcc ccgccgtggg gtttctgcct agaacagagt tccagtacaa cgactccaat   1140
tgccccatca tccactgtaa gtattctaaa gctgaaaact gcaggctgag catgggagtg   1200
aattctaaga gccattacat cctgagatcc ggcctgctga atataaccct gtctctgggc   1260
ggggacatca tcctgcagtt catcgagatc gccgataaca gactgaccat cgggtccccc   1320
tctaagatct acaatagcct gggacagcct gtgttttacc aggctagcta ttcctgggac   1380
accatgatca aactgggcga cgtggataca gtggatcctc tgcgcgtgca gtggcggaat   1440
aactccgtga tctctaggcc aggacagtcc cagtgtccca gattcaacgt gtgccctgaa   1500
gtgtgttggg aaggcaccta caacgacgcc tttctgatcg ataggctgaa ttgggtgtct   1560
gctggggtgt atctgaatag caaccagaca gccgagaacc ctgtgttcgc tgtgtttaag   1620
gacaatgaga tcctgtacca ggtgccactg gccgaagacg ataccaacgc tcagaaaacc   1680
atcacagatt gcttcctgct ggagaatgtg atctggtgta tctctctggt ggaaatctat   1740
gacaccggcg atagcgtgat cagacccaag ctgtttgccg tgaaaatccc tgctcagtgc   1800
tctgaaagct ga                                                        1812
```

<210> SEQ ID NO 3
<211> LENGTH: 600
<212> TYPE: PRT
<213> ORGANISM: artificial sequence
<220> FEATURE:
<223> OTHER INFORMATION: Hendra G protein

<400> SEQUENCE: 3

Met Ala Asp Ser Lys Leu Val Ser Leu Asn Asn Asn Leu Ser Gly Lys
1               5                   10                  15

Ile Lys Asp Gln Gly Lys Val Ile Lys Asn Tyr Tyr Gly Thr Met Asp
                20                  25                  30

Ile Lys Lys Ile Asn Asp Gly Leu Leu Asp Ser Lys Ile Leu Gly Ala
            35                  40                  45

Phe Asn Thr Val Ile Ala Leu Leu Gly Ser Ile Ile Ile Ile Val Met
        50                  55                  60

Asn Ile Met Ile Ile Gln Asn Tyr Thr Arg Thr Thr Asp Asn Gln Ala
65                  70                  75                  80

```
Leu Ile Lys Glu Ser Leu Gln Ser Val Gln Gln Ile Lys Ala Leu
                85                  90                  95

Thr Asp Lys Ile Gly Thr Glu Ile Gly Pro Lys Val Ser Leu Ile Asp
            100                 105                 110

Thr Ser Ser Thr Ile Thr Ile Pro Ala Asn Ile Gly Leu Leu Gly Ser
        115                 120                 125

Lys Ile Ser Gln Ser Thr Ser Ser Ile Asn Glu Asn Val Asn Asp Lys
    130                 135                 140

Cys Lys Phe Thr Leu Pro Pro Leu Lys Ile His Glu Cys Asn Ile Ser
145                 150                 155                 160

Cys Pro Asn Pro Leu Pro Phe Arg Glu Tyr Arg Pro Ile Ser Gln Gly
                165                 170                 175

Val Ser Asp Leu Val Gly Leu Pro Asn Gln Ile Cys Leu Gln Lys Thr
            180                 185                 190

Thr Ser Thr Ile Leu Lys Pro Arg Leu Ile Ser Tyr Thr Leu Pro Ile
        195                 200                 205

Asn Thr Arg Glu Gly Val Cys Ile Thr Asp Pro Leu Leu Ala Val Asp
    210                 215                 220

Asn Gly Phe Phe Ala Tyr Ser His Leu Glu Lys Ile Gly Ser Cys Thr
225                 230                 235                 240

Arg Gly Ile Ala Lys Gln Arg Ile Ile Gly Val Gly Glu Val Leu Asp
                245                 250                 255

Arg Gly Asp Lys Val Pro Ser Met Phe Met Thr Asn Val Trp Thr Pro
            260                 265                 270

Pro Asn Pro Ser Thr Ile His His Cys Ser Ser Thr Tyr His Glu Asp
        275                 280                 285

Phe Tyr Tyr Thr Leu Cys Ala Val Ser His Val Gly Asp Pro Ile Leu
    290                 295                 300

Asn Ser Thr Ser Trp Thr Glu Ser Leu Ser Leu Ile Arg Leu Ala Val
305                 310                 315                 320

Arg Pro Lys Ser Asp Ser Gly Asp Tyr Asn Gln Lys Tyr Ile Ala Ile
                325                 330                 335

Thr Lys Val Glu Arg Gly Lys Tyr Asp Lys Val Met Pro Tyr Gly Pro
            340                 345                 350

Ser Gly Ile Lys Gln Gly Asp Thr Leu Tyr Phe Pro Ala Val Gly Phe
        355                 360                 365

Leu Pro Arg Thr Glu Phe Gln Tyr Asn Asp Ser Asn Cys Pro Ile Ile
    370                 375                 380

His Cys Lys Tyr Ser Lys Ala Glu Asn Cys Arg Leu Ser Met Gly Val
385                 390                 395                 400

Asn Ser Lys Ser His Tyr Ile Leu Arg Ser Gly Leu Leu Lys Tyr Asn
                405                 410                 415

Leu Ser Leu Gly Gly Asp Ile Ile Leu Gln Phe Ile Glu Ile Ala Asp
            420                 425                 430

Asn Arg Leu Thr Ile Gly Ser Pro Ser Lys Ile Tyr Asn Ser Leu Gly
        435                 440                 445

Gln Pro Val Phe Tyr Gln Ala Ser Tyr Ser Trp Asp Thr Met Ile Lys
    450                 455                 460

Leu Gly Asp Val Asp Thr Val Asp Pro Leu Arg Val Gln Trp Arg Asn
465                 470                 475                 480

Asn Ser Val Ile Ser Arg Pro Gly Gln Ser Gln Cys Pro Arg Phe Asn
                485                 490                 495
```

```
Val Cys Pro Glu Val Cys Trp Glu Gly Thr Tyr Asn Asp Ala Phe Leu
            500                 505                 510
Ile Asp Arg Leu Asn Trp Val Ser Ala Gly Val Tyr Leu Asn Ser Asn
        515                 520                 525
Gln Thr Ala Glu Asn Pro Val Phe Ala Val Phe Lys Asp Asn Glu Ile
    530                 535                 540
Leu Tyr Gln Val Pro Leu Ala Glu Asp Asp Thr Asn Ala Gln Lys Thr
545                 550                 555                 560
Ile Thr Asp Cys Phe Leu Leu Glu Asn Val Ile Trp Cys Ile Ser Leu
                565                 570                 575
Val Glu Ile Tyr Asp Thr Gly Asp Ser Val Ile Arg Pro Lys Leu Phe
            580                 585                 590
Ala Val Lys Ile Pro Ala Gln Cys
            595                 600

<210> SEQ ID NO 4
<211> LENGTH: 1641
<212> TYPE: DNA
<213> ORGANISM: artificial sequence
<220> FEATURE:
<223> OTHER INFORMATION: wildtype DNA encoding Hendra F protein

<400> SEQUENCE: 4
atggctacac aagaggtcag gctaaagtgt ttgctctgtg ggatcatagt tctggttttg     60
tcattagaag ggctagggat actacattat gagaaactta gtaagatagg gctggttaaa    120
ggtattacaa gaaagtacaa gattaagagt aacccttTga ccaaggatat tgtgatcaaa    180
atgatcccta atgtctcgaa tgtctcaaag tgcaccggga ctgttatgga gaattacaaa    240
agcagactca gggattctct ctcaccaatc aaaggcgcca tcgaactgta caataataac    300
acgcatgacc tagttggtga tgtcaagctt gcaggtgtgg tgatggcagg gattgcaatc    360
gggatagcta ctgctgcaca aatcacagca ggtgttgcct atatgaggc aatgaagaac    420 gcagacaata tcaataaact caagagcagc atagagtcta caaatgaggc tgttgtcaaa    480
ttacaggaaa cagctgagaa acagtctac gtccttactg ctcttcaaga ttacatcaac    540
actaaccttg ttcctacaat agatcaaatt agctgcaagc aaacagagct cgcattagac    600
ttggcgttgt ctaagtatct gtctgatctg ctctttgttt tcggacctaa cttacaggat    660
ccagtctcta attccatgac tatccaagca atatctcaag catttgggg caattacgaa    720 accttactga aacgcttgg ttacgcgacc gaggacttcg acgacctttt agaaagtgat    780
agcatagcag ccagatagt ctatgtgat ctcagtagct attacataat agtaagggtg    840
tattttccca tactaacaga gatccaacag gcttatgtgc aggagttgct tccagtgagt    900
tttaataacg ataattcaga atggatcagc attgtcccga atttcgtgct gattaggaac    960
acgctgattt caaatataga agtcaagtac tgcttaatca ccaagaaaag tgtgatttgt   1020
aatcaggact atgctacacc catgacggct agcgtgagag aatgcttgac aggatccaca   1080
gataagtgcc aagggagtt agtagtctca tcccatgttc caagatttgc cctctcagga   1140
ggagtcttgt ttgcaaattg tataagtgtg acatgtcagt gtcagactac tgggagggca   1200
atatctcaat caggggaaca gacactactg atgattgaca atactacctg cacaacagtt   1260
gttctaggaa acataatcat aagccttgga aaatatttgg gatcaataaa ttacaattct   1320
gagagcattg ctgttgggcc accagtctat acagacaaag ttgatatctc aagtcagata   1380
tctagtatga atcaatcact acaacaatct aaggattaca ttaagaagc tcaaaagatc   1440
```

| ttggacactg tgaatccgtc gttgataagt atgctatcaa tgatcatcct ttatgttttg | 1500 |
| tccattgcag cactgtgcat tggtctgatc actttcataa gctttgtaat agttgagaaa | 1560 |
| aagagaggga attacagcag gctagatgat aggcaagtgc gaccggtcag taatggtgat | 1620 |
| ctgtattata ttggaacata a | 1641 |

```
<210> SEQ ID NO 5
<211> LENGTH: 1641
<212> TYPE: DNA
<213> ORGANISM: artificial sequence
<220> FEATURE:
<223> OTHER INFORMATION: codon-optimized DNA encoding Hendra F protein

<400> SEQUENCE: 5
```

| atggccaccc aggaggtgcg cctgaagtgc ctgctgtgtg gcatcatcgt gctggtgctg | 60 |
| agcctggagg gactgggaat cctgcactac gaaaaactgt ccaagatcgg cctggtgaag | 120 |
| gggatcaccc ggaagtataa aatcaagagc aatcccctga caaggacat cgtgatcaaa | 180 |
| atgatcccta atgtgagcaa cgtgtccaag tgcaccggca cagtgatgga gaactacaaa | 240 |
| tctaggctga ccgggatcct gagccctatc aagggagcca tcgaactgta taacaataac | 300 |
| acacatgacc tggtgggcga tgtgaaactg gccggggtgg tcatggccgg aatcgctatc | 360 |
| ggcatcgcta ccgctgctca gatcacagct ggagtggctc tgtacgaggc catgaagaat | 420 |
| gctgacaata tcaacaaact gaagagctcc atcgagtcca ccaacgaagc cgtggtgaag | 480 |
| ctgcaggaga ccgctgaaaa aacagtgtac gtgctgacag ccctgcagga ctatatcaat | 540 |
| accaacctgg tgccaacaat cgatcagatc agctgtaagc agaccgaact ggccctggac | 600 |
| ctggctctgt ctaaatacct gagcgatctg ctgttcgtgt ttggcccaaa tctgcaggat | 660 |
| cccgtgtcca actctatgac catccaggcc atctcccagg cttcggcgg aactacgag | 720 |
| accctgctga ggacactggg gtatgccacc gaggactttg acgatctgct ggaaagcgat | 780 |
| tccatcgctg acagatcgt gtacgtggac ctgtctagct actatatcat cgtgagagtg | 840 |
| tacttcccaa tcctgaccga gatccagcag gcctatgtgc aggaactgct gcccgtgagc | 900 |
| ttcaataacg ataattccga gtggatctct atcgtgccta actttgtgct gatccgcaat | 960 |
| accctgatct ctaacatcga agtgaagtac tgcctgatca caaagaaaag cgtgatctgt | 1020 |
| aaccaggact atgccacccc catgacagct agcgtgcggg agtgcctgac cggatccacc | 1080 |
| gataagtgtc ctagggaact ggtggtgtcc tctcacgtgc aagattcgc cctgtctgga | 1140 |
| ggcgtgctgt ttgctaactg catcagcgtg acctgccagt gtcagaccac aggcagagcc | 1200 |
| atctctcaga gcggggagca gacactgctg atgatcgaca taccacatg taccacagtg | 1260 |
| gtgctgggca acatcatcat ctccctgggg aagtacctgg atctatcaa ttataactcc | 1320 |
| gaatctatcg ccgtggggcc ccctgtgtac accgacaaag tggacatcag cagccagatc | 1380 |
| tctagcatga atcagagcct gcagcagtcc aaagactata tcaaggaggc cagaaaatc | 1440 |
| ctggataccg tgaacccatc tctgatcagc atgctgtcca tgatcatcct gtacgtgctg | 1500 |
| tccatcgccg ctctgtgcat cggactgatc accttcatca gctttgtgat cgtggagaag | 1560 |
| aaacgcggca attactcccg gctggacgat aggcaggtga gacccgtgtc taacggagac | 1620 |
| ctgtactata tcggcaccctg a | 1641 |

```
<210> SEQ ID NO 6
<211> LENGTH: 546
<212> TYPE: PRT
<213> ORGANISM: artificial sequence
```

-continued

```
<220> FEATURE:
<223> OTHER INFORMATION: Hendra F protein

<400> SEQUENCE: 6

Met Ala Thr Gln Glu Val Arg Leu Lys Cys Leu Leu Cys Gly Ile Ile
1               5                   10                  15

Val Leu Val Leu Ser Leu Glu Gly Leu Gly Ile Leu His Tyr Glu Lys
            20                  25                  30

Leu Ser Lys Ile Gly Leu Val Lys Gly Ile Thr Arg Lys Tyr Lys Ile
        35                  40                  45

Lys Ser Asn Pro Leu Thr Lys Asp Ile Val Ile Lys Met Ile Pro Asn
    50                  55                  60

Val Ser Asn Val Ser Lys Cys Thr Gly Thr Val Met Glu Asn Tyr Lys
65                  70                  75                  80

Ser Arg Leu Thr Gly Ile Leu Ser Pro Ile Lys Gly Ala Ile Glu Leu
                85                  90                  95

Tyr Asn Asn Asn Thr His Asp Leu Val Gly Asp Val Lys Leu Ala Gly
            100                 105                 110

Val Val Met Ala Gly Ile Ala Ile Gly Ile Ala Thr Ala Ala Gln Ile
        115                 120                 125

Thr Ala Gly Val Ala Leu Tyr Glu Ala Met Lys Asn Ala Asp Asn Ile
    130                 135                 140

Asn Lys Leu Lys Ser Ser Ile Glu Ser Thr Asn Glu Ala Val Val Lys
145                 150                 155                 160

Leu Gln Glu Thr Ala Glu Lys Thr Val Tyr Val Leu Thr Ala Leu Gln
                165                 170                 175

Asp Tyr Ile Asn Thr Asn Leu Val Pro Thr Ile Asp Gln Ile Ser Cys
            180                 185                 190

Lys Gln Thr Glu Leu Ala Leu Asp Leu Ala Leu Ser Lys Tyr Leu Ser
        195                 200                 205

Asp Leu Leu Phe Val Phe Gly Pro Asn Leu Gln Asp Pro Val Ser Asn
    210                 215                 220

Ser Met Thr Ile Gln Ala Ile Ser Gln Ala Phe Gly Gly Asn Tyr Glu
225                 230                 235                 240

Thr Leu Leu Arg Thr Leu Gly Tyr Ala Thr Glu Asp Phe Asp Asp Leu
                245                 250                 255

Leu Glu Ser Asp Ser Ile Ala Gly Gln Ile Val Tyr Val Asp Leu Ser
            260                 265                 270

Ser Tyr Tyr Ile Ile Val Arg Val Tyr Phe Pro Ile Leu Thr Glu Ile
        275                 280                 285

Gln Gln Ala Tyr Val Gln Glu Leu Leu Pro Val Ser Phe Asn Asn Asp
    290                 295                 300

Asn Ser Glu Trp Ile Ser Ile Val Pro Asn Phe Val Leu Ile Arg Asn
305                 310                 315                 320

Thr Leu Ile Ser Asn Ile Glu Val Lys Tyr Cys Leu Ile Thr Lys Lys
                325                 330                 335

Ser Val Ile Cys Asn Gln Asp Tyr Ala Thr Pro Met Thr Ala Ser Val
            340                 345                 350

Arg Glu Cys Leu Thr Gly Ser Thr Asp Lys Cys Pro Arg Glu Leu Val
        355                 360                 365

Val Ser Ser His Val Pro Arg Phe Ala Leu Ser Gly Gly Val Leu Phe
    370                 375                 380

Ala Asn Cys Ile Ser Val Thr Cys Gln Cys Gln Thr Thr Gly Arg Ala
385                 390                 395                 400
```

-continued

```
Ile Ser Gln Ser Gly Glu Gln Thr Leu Leu Met Ile Asp Asn Thr Thr
                405                 410                 415

Cys Thr Thr Val Val Leu Gly Asn Ile Ile Ile Ser Leu Gly Lys Tyr
            420                 425                 430

Leu Gly Ser Ile Asn Tyr Asn Ser Glu Ser Ile Ala Val Gly Pro Pro
        435                 440                 445

Val Tyr Thr Asp Lys Val Asp Ile Ser Ser Gln Ile Ser Ser Met Asn
    450                 455                 460
Gln Ser Leu Gln Gln Ser Lys Asp Tyr Ile Lys Glu Ala Gln Lys Ile
465                 470                 475                 480
Leu Asp Thr Val Asn Pro Ser Leu Ile Ser Met Leu Ser Met Ile Ile
                485                 490                 495
Leu Tyr Val Leu Ser Ile Ala Ala Leu Cys Ile Gly Leu Ile Thr Phe
            500                 505                 510
Ile Ser Phe Val Ile Val Glu Lys Lys Arg Gly Asn Tyr Ser Arg Leu
        515                 520                 525
Asp Asp Arg Gln Val Arg Pro Val Ser Asn Gly Asp Leu Tyr Tyr Ile
    530                 535                 540
Gly Thr
545
```

<210> SEQ ID NO 7
<211> LENGTH: 1936
<212> TYPE: DNA
<213> ORGANISM: artificial sequence
<220> FEATURE:
<223> OTHER INFORMATION: part of plasmid p362 containing Hendra G and H6 promoter

<400> SEQUENCE: 7

```
ttctttattc tatacttaaa aagtgaaaat aaatacaaag gttcttgagg gttgtgttaa      60
attgaaagcg agaaataatc ataaattatt tcattatcgc gatatccgtt aagtttgtat     120
cgtaatggcc gactccaagc tggtgtctct gaacaataac ctgagcggca agatcaaaga     180
ccagggcaaa gtgatcaaga actactatgg aaccatggac atcaagaaga tcaacgacgg     240
actgctggat tccaagatcc tgggcgcctt caacacagtg atcgctctgc tgggctctat     300
catcatcatc gtgatgaaca tcatgatcat ccagaattac accagaacca cagacaacca     360
ggccctgatc aaggagtctc tgcagagcgt gcagcagcag atcaaggctc tgaccgacaa     420 aatcggaca gaaatcggac ccaaggtgag cctgatcgat accagctcca ccatcacaat      480
ccctgccaac atcggactgc tgggctccaa aatcagccag tccacctcta gcatcaacga     540
gaatgtgaac gacaagtgca aattcacact gccccctctg aagatccacg agtgcaacat     600
cagctgtcca aatcccctgc cttttaggga atacagacct atcagccagg gagtgtccga     660
cctggtggga ctgccaaacc agatctgtct gcagaagacc acatccacca tcctgaaacc     720
taggctgatc tcttacaccc tgccaatcaa cacaagagag ggcgtgtgca tcacagaccc     780
cctgctggcc gtggataatg ggttctttgc ttatagccat ctggagaaga tcggatcctg     840
taccaggggc atcgccaaac agagaatcat cggggtggga gaagtgctgg acaggggcga     900
taaggtgcca agcatgttca tgaccaacgt gtggacacca cccaatccct ccaccatcca     960
ccattgctcc tctacatacc acgaggactt ttactatacc ctgtgtgccg tgtcccatgt    1020
gggcgatcca atcctgaact ctaccagctg gacagaatcc ctgtctctga tcaggctggc    1080
cgtgagacct aagagcgact ccggggatta caatcagaag tatatcgcta tcaccaaagt    1140
```

| | |
|---|---|
| ggagagggga aagtacgaca aagtgatgcc atatgggccc agcggaatca agcagggcga | 1200 |
| taccctgtac ttccccgccg tggggtttct gcctagaaca gagttccagt acaacgactc | 1260 |
| caattgcccc atcatccact gtaagtattc taaagctgaa aactgcaggc tgagcatggg | 1320 |
| agtgaattct aagagccatt acatcctgag atccggcctg ctgaaatata acctgtctct | 1380 |
| gggcggggac atcatcctgc agttcatcga gatcgccgat aacagactga ccatcgggtc | 1440 |
| cccctctaag atctacaata gcctgggaca gcctgtgttt taccaggcta gctattcctg | 1500 |
| ggacaccatg atcaaactgg gcgacgtgga tacagtggat cctctgcgcg tgcagtggcg | 1560 |
| gaataactcc gtgatctcta ggccaggaca gtcccagtgt cccagattca acgtgtgccc | 1620 |
| tgaagtgtgt tgggaaggca cctacaacga cgcctttctg atcgataggc tgaattgggt | 1680 |
| gtctgctggg gtgtatctga atagcaacca gacagccgag aaccctgtgt cgctgtgtt | 1740 |
| taaggacaat gagatcctgt accaggtgcc actggccgaa gacgatacca acgctcagaa | 1800 |
| aaccatcaca gattgcttcc tgctggagaa tgtgatctgg tgtatctctc tggtggaaat | 1860 |
| ctatgacacc ggcgatagcg tgatcagacc caagctgttt gccgtgaaaa tccctgctca | 1920 |
| gtgctctgaa agctga | 1936 |

<210> SEQ ID NO 8
<211> LENGTH: 4113
<212> TYPE: DNA
<213> ORGANISM: artificial sequence
<220> FEATURE:
<223> OTHER INFORMATION: part p362 plasmid containing G gene, H6
      promoter and C5 arms

<400> SEQUENCE: 8

| | |
|---|---|
| ggaaacagct atgaccatga ttacgaattg cggccgcaat tctgaatgtt aaatgttata | 60 |
| ctttggatga agctataaat atgcattgga aaaataatcc atttaaagaa aggattcaaa | 120 |
| tactacaaaa cctaagcgat aatatgttaa ctaagcttat tcttaacgac gctttaaata | 180 |
| tacacaaata aacataattt ttgtataacc taacaaataa ctaaaacata aaaataataa | 240 |
| aaggaaatgt aatatcgtaa ttattttact caggaatggg gttaaatatt tatatcacgt | 300 |
| gtatatctat actgttatcg tatactcttt acaattacta ttacgaatat gcaagagata | 360 |
| ataagattac gtatttaaga gaatcttgtc atgataattg ggtacgacat agtgataaat | 420 |
| gctatttcgc atcgttacat aaagtcagtt ggaaagatgg atttgacaga tgtaacttaa | 480 |
| taggtgcaaa aatgttaaat aacagcattc tatcggaaga taggatacca gttatattat | 540 |
| acaaaaatca ctggttggat aaaacagatt ctgcaatatt cgtaaaagat gaagattact | 600 |
| gcgaatttgt aaactatgac aataaaaagc catttatctc aacgacatcg tgtaattctt | 660 |
| ccatgtttta tgtatgtgtt tcagatatta tgagattact ataaactttt tgtatactta | 720 |
| tattccgtaa actatattaa tcatgaagaa aatgaaaaag tatagaagct gttcacgagc | 780 |
| ggttgttgaa acaacaaaa ttatacattc aagatggctt acatatacgt ctgtgaggct | 840 |
| atcatggata atgacaatgc atctctaaat aggttttttgg acaatggatt cgaccctaac | 900 |
| acggaatatg gtactctaca atctcctctt gaaatggctg taatgttcaa gaataccgag | 960 |
| gctataaaaa tcttgatgag gtatggagct aaacctgtag ttactgaatg cacaacttct | 1020 |
| tgtctgcatg atgcggtgtt gagagacgac tacaaaatag tgaagatct gttgaagaat | 1080 |
| aactatgtaa acaatgttct ttacagcgga ggctttactc ctttgtgttt ggcagcttac | 1140 |
| cttaacaaag ttaatttggt taaacttcta ttggctcatt cggcggatgt agatatttca | 1200 |

```
aacacggatc ggttaactcc tctacatata gccgtatcaa ataaaaattt aacaatggtt    1260
aaacttctat tgaacaaagg tgctgatact gacttgctgg ataacatggg acgtactcct    1320
ttaatgatcg ctgtacaatc tggaaatatt gaaatatgta gcacactact taaaaaaaat    1380
aaaatgtcca gaactgggaa aaattgatct tgccagctgt aattcatggt agaaaagaag    1440
tgctcaggct acttttcaac aaaggagcag atgtaaacta catctttgaa agaaatggaa    1500
aatcatatac tgttttggaa ttgattaaag aaagttactc tgagacacaa aagaggtagc    1560
tgaagtggta ctctcaaagg tacgtgacta attagctata aaaaggatcc gggttaatta    1620
attagtcatc aggcagggcg agaacgagac tatctgctcg ttaattaatt agagcttctt    1680
tattctatac ttaaaaagtg aaaataaata caaaggttct tgagggttgt gttaaattga    1740
aagcgagaaa taatcataaa ttatttcatt atcgcgatat ccgttaagtt tgtatcgtaa    1800
tggccgactc caagctggtg tctctgaaca ataacctgag cggcaagatc aaagaccagg    1860
gcaaagtgat caagaactac tatgaaccca tggacatcaa gaagatcaac gacggactgc    1920
tggattccaa gatcctgggc gccttcaaca cagtgatcgc tctgctgggc tctatcatca    1980
tcatcgtgat gaacatcatg atcatccaga attacaccag aacccagaca aaccaggccc    2040
tgatcaagga gtctctgcag agcgtgcagc agcagatcaa ggctctgacc gacaaaatcg    2100
ggacagaaat cggacccaag gtgagcctga tcgataccag ctccaccatc acaatccctg    2160
ccaacatcgg actgctgggc tccaaaatca gccagtccac ctctagcatc aacgagaatg    2220
tgaacgacaa gtgcaaattc acactgcccc ctctgaagat ccacgagtgc aacatcagct    2280
gtccaaatcc cctgccttt agggaataca gacctatcag ccagggagtg tccgacctgg    2340
tgggactgcc aaaccagatc tgtctgcaga agaccacatc caccatcctg aaacctaggc    2400
tgatctctta caccctgcca atcaacacaa gagagggcgt gtgcatcaca gacccctgc    2460 tggccgtgga taatgggttc tttgcttata gccatctgga agatcggaa tcctgtacca    2520 ggggcatcgc caaacagaga atcatcgggg tgggagaagt gctggacagg ggcgataagg    2580
tgccaagcat gttcatgacc aacgtgtgga caccacccaa tccctccacc atccaccatt    2640
gctcctctac ataccacgag gacttttact atacccctgtg tgccgtgtcc catgtgggcg    2700
atccaatcct gaactctacc agctggacag aatccctgtc tctgatcagg ctggccgtga    2760
gacctaagag cgactccggg gattacaatc agaagtatat cgctatcacc aaagtggaga    2820
ggggaaagta cgacaaagtg atgccatatg ggcccagcgg aatcaagcag ggcgataccc    2880
tgtacttccc cgccgtgggg tttctgccta gaacagagtt ccagtacaac gactccaatt    2940
gccccatcat ccactgtaag tattctaaag ctgaaaactg caggctgagc atgggagtga    3000
attctaagag ccattacatc ctgagatccg gcctgctgaa atataacctg tctctgggcg    3060
gggacatcat cctgcagttc atcgagatcg ccgataacag actgaccatc gggtcccct    3120 ctaagatcta caatagcctg gacagcctgt gttttacca ggctagctat tcctgggaca    3180
ccatgatcaa actgggcgac gtggatacag tggatcctct gcgcgtgcag tggcggaata    3240
actccgtgat ctctaggcca ggacagtccc agtgtcccag attcaacgtg tgccctgaag    3300
tgtgttggga aggcacctac aacgacgcct ttctgatcga taggctgaat tgggtgtctg    3360
ctggggtgta tctgaatagc aaccagacag ccgagaaccc tgtgttcgct gtgtttaagg    3420
acaatgagat cctgtaccag gtgccactgg ccgaagacga taccaacgct cagaaaacca    3480
tcacagattg cttcctgctg gagaatgtga tctggtgtat ctctctggtg gaaatctatg    3540
```

| | |
|---|---:|
| acaccggcga tagcgtgatc agacccaagc tgtttgccgt gaaaatccct gctcagtgct | 3600 |
| ctgaaagctg attttatgg taccctcgag tctagaatcg atcccgggtt tttatgacta | 3660 |
| gttaatcacg gccgcttata aagatctaaa atgcataatt tctaaataat gaaaaaagt | 3720 |
| acatcatgag caacgcgtta gtatatttta caatggagat aacgctcta taccgttcta | 3780 |
| tgtttattga ttcagatgat gttttagaaa agaaagttat tgaatatgaa aactttaatg | 3840 |
| aagatgaaga tgacgacgat gattattgtt gtaaatctgt tttagatgaa gaagatgacg | 3900 |
| cgctaaagta tactatggtt acaaagtata agtctatact actaatggcg acttgtgcaa | 3960 |
| gaaggtatag tatagtgaaa atgttgttag attatgatta tgaaaaacca aataaatcag | 4020 |
| atccatatct aaaggtatct cctttgcaca taatttcatc tattcctagt ttagaatacc | 4080 |
| tgcagccaag cttggcactg gccgtcgttt tac | 4113 |

<210> SEQ ID NO 9
<211> LENGTH: 6698
<212> TYPE: DNA
<213> ORGANISM: artificial sequence
<220> FEATURE:
<223> OTHER INFORMATION: entire p362 plasmid sequence

<400> SEQUENCE: 9

| | |
|---|---:|
| gcgcccaata cgcaaaccgc ctctccccgc gcgttggccg attcattaat gcagctggca | 60 |
| cgacaggttt cccgactgga aagcgggcag tgagcgcaac gcaattaatg tgagttagct | 120 |
| cactcattag gcaccccagg ctttacactt tatgcttccg gctcgtatgt tgtgtggaat | 180 |
| tgtgagcgga taacaatttc acacaggaaa cagctatgac catgattacg aattgcggcc | 240 |
| gcaattctga atgttaaatg ttatactttg gatgaagcta taaatatgca ttggaaaaat | 300 |
| aatccattta agaaaggat tcaaatacta caaaacctaa gcgataatat gttaactaag | 360 |
| cttattctta acgacgcttt aaatatacac aaataaacat aattttgta taacctaaca | 420 |
| aataactaaa acataaaaat aataaaagga aatgtaaat cgtaattatt ttactcagga | 480 |
| atggggttaa atatttatat cacgtgtata tctatactgt tatcgtatac tctttacaat | 540 |
| tactattacg aatatgcaag agataataag attacgtatt taagagaatc ttgtcatgat | 600 |
| aattgggtac gacatagtga taaatgctat ttcgcatcgt tacataaagt cagttggaaa | 660 |
| gatggatttg acagatgtaa cttaataggt gcaaaatgt taaataacag cattctatcg | 720 |
| gaagatagga taccagttat attatacaaa aatcactggt tggataaaac agattctgca | 780 |
| atattcgtaa aagatgaaga ttactgcgaa tttgtaaact atgacaataa aaagccattt | 840 |
| atctcaacga catcgtgtaa ttcttccatg ttttatgtat gtgtttcaga tattatgaga | 900 |
| ttactataaa cttttttgtat acttatattc cgtaaactat attaatcatg aagaaaatga | 960 |
| aaaagtatag aagctgttca cgagcggttg ttgaaaacaa caaaattata cattcaagat | 1020 |
| ggcttacata tacgtctgtg aggctatcat ggataatgac aatgcatctc taaataggtt | 1080 |
| tttggacaat ggattcgacc ctaacacgga atatggtact ctacaatctc ctcttgaaat | 1140 |
| ggctgtaatg ttcaagaata ccgaggctat aaaaatcttg atgaggtatg gagctaaacc | 1200 |
| tgtagttact gaatgcacaa cttccttgtct gcatgatgcg gtgttgagag acgactacaa | 1260 |
| aatagtgaaa gatctgttga agaataacta tgtaaacaat gttctttaca gcggaggctt | 1320 |
| tactcctttg tgtttggcag cttaccttaa caaagttaat ttggttaaac ttctattggc | 1380 |
| tcattcggcg gatgtagata tttcaaacac ggatcggtta actcctctac atatagccgt | 1440 |
| atcaaataaa aatttaacaa tggttaaact tctattgaac aaaggtgctg atactgactt | 1500 |

```
gctggataac atgggacgta ctcctttaat gatcgctgta caatctggaa atattgaaat    1560
atgtagcaca ctacttaaaa aaataaaat gtccagaact gggaaaaatt gatcttgcca     1620
gctgtaattc atggtagaaa agaagtgctc aggctacttt tcaacaaagg agcagatgta    1680
aactacatct ttgaaagaaa tggaaaatca tatactgttt tggaattgat taaagaaagt    1740
tactctgaga cacaaaagag gtagctgaag tggtactctc aaaggtacgt gactaattag    1800
ctataaaaag gatccgggtt aattaattag tcatcaggca gggcgagaac gagactatct    1860
gctcgttaat taattagagc ttctttattc tatacttaaa aagtgaaaat aaatacaaag    1920
gttcttgagg gttgtgttaa attgaaagcg agaaataatc ataaattatt tcattatcgc    1980
gatatccgtt aagtttgtat cgtaatggcc gactccaagc tggtgtctct gaacaataac    2040
ctgagcggca agatcaaaga ccagggcaaa gtgatcaaga actactatgg aaccatggac    2100
atcaagaaga tcaacgacgg actgctggat tccaagatcc tgggcgcctt caacacagtg    2160
atcgctctgc tgggctctat catcatcatc gtgatgaaca tcatgatcat ccagaattac    2220
accagaacca cagacaacca ggccctgatc aaggagtctc tgcagagcgt gcagcagcag    2280
atcaaggctc tgaccgacaa aatcgggaca gaaatcggac ccaaggtgag cctgatcgat    2340
accagctcca ccatcacaat ccctgccaac atcggactgc tgggctccaa aatcagccag    2400
tccacctcta gcatcaacga gaatgtgaac gacaagtgca aattcacact gccccctctg    2460
aagatccacg agtgcaacat cagctgtcca aatccctgc cttttaggga atacagacct    2520
atcagccagg gagtgtccga cctggtggga ctgccaaacc agatctgtct gcagaagacc    2580
acatccacca tcctgaaacc taggctgatc tcttacaccc tgccaatcaa cacaagagag    2640
ggcgtgtgca tcacagaccc cctgctggcc gtggataatg ggttctttgc ttatagccat    2700
ctggagaaga tcggatcctg taccagggc atcgccaaac agagaatcat cggggtggga    2760
gaagtgctgg acaggggcga taaggtgcca agcatgttca tgaccaacgt gtggacacca    2820
cccaatccct ccaccatcca ccattgctcc tctacatacc acgaggactt ttactatacc    2880
ctgtgtgccg tgtcccatgt gggcgatcca atcctgaact ctaccagctg gacagaatcc    2940
ctgtctctga tcaggctggc cgtgagacct aagagcgact ccggggatta caatcagaag    3000
tatatcgcta tcaccaaagt ggagaggga aagtacgaca aagtgatgcc atatgggccc    3060
agcggaatca agcagggcga taccctgtac ttccccgccg tggggtttct gcctagaaca    3120
gagttccagt acaacgactc caattgcccc atcatccact gtaagtattc taaagctgaa    3180
aactgcaggc tgagcatggg agtgaattct aagagccatt acatcctgag atccggcctg    3240
ctgaaatata acctgtctct gggcgggac atcatcctgc agttcatcga gatcgccgat    3300
aacagactga ccatcgggtc cccctctaag atctacaata gcctgggaca gcctgtgttt    3360
taccaggcta gctattcctg ggacaccatg atcaaactgg gcgacgtgga tacagtggat    3420
cctctgcgcg tgcagtggcg gaataactcc gtgatctcta ggccaggaca gtcccagtgt    3480
cccagattca acgtgtgccc tgaagtgtgt tgggaaggca cctacaacga cgccttctg    3540 atcgataggc tgaattgggt gtctgctggg gtgtatctga atagcaacca gacagccgag    3600
aaccctgtgt tcgctgtgtt taaggacaat gagatcctgt accaggtgcc actggccgaa    3660
gacgatacca acgctcagaa aaccatcaca gattgcttcc tgctggagaa tgtgatctgg    3720
tgtatctctc tggtggaaat ctatgacacc ggcgatagcg tgatcagacc caagctgttt    3780
gccgtgaaaa tccctgctca gtgctctgaa agctgatttt tatggtaccc tcgagtctag    3840
```

-continued

```
aatcgatccc gggttttat gactagttaa tcacggccgc ttataaagat ctaaaatgca    3900
taatttctaa ataatgaaaa aaagtacatc atgagcaacg cgttagtata ttttacaatg    3960
gagattaacg ctctataccg ttctatgttt attgattcag atgatgtttt agaaaagaaa    4020
gttattgaat atgaaaactt taatgaagat gaagatgacg acgatgatta ttgttgtaaa    4080
tctgttttag atgaagaaga tgacgcgcta aagtatacta tggttacaaa gtataagtct    4140
atactactaa tggcgacttg tgcaagaagg tatagtatag tgaaaatgtt gttagattat    4200
gattatgaaa aaccaaataa atcagatcca tatctaaagg tatctccttt gcacataatt    4260
tcatctattc ctagtttaga ataacctgcag ccaagcttgg cactggccgt cgttttacaa    4320
cgtcgtgact gggaaaaccc tggcgttacc caacttaatc gccttgcagc acatccccct    4380
ttcgccagct ggcgtaatag cgaagaggcc cgcaccgatc gcccttccca acagttgcgc    4440
agcctgaatg gcgaatggcg cctgatgcgg tattttctcc ttacgcatct gtgcggtatt    4500
tcacaccgca tatggtgcac tctcagtaca atctgctctg atgccgcata gttaagccag    4560
ccccgacacc cgccaacacc cgctgacgcg ccctgacggg cttgtctgct cccggcatcc    4620
gcttacagac aagctgtgac cgtctccggg agctgcatgt gtcagaggtt ttcaccgtca    4680
tcaccgaaac gcgcgagacg aaagggcctc gtgatacgcc tatttttata ggttaatgtc    4740
atgataataa tggtttctta cgtcaggt ggcacttttc ggggaaatgt gcgcggaacc    4800
cctatttgtt tatttttcta aatacattca aatatgtatc cgctcatgag acaataaccc    4860
tgataaatgc ttcaataata ttgaaaaagg aagagtatga gtattcaaca tttccgtgtc    4920
gcccttattc cctttttgc ggcattttgc cttcctgttt ttgctcaccc agaaacgctg    4980
gtgaaagtaa aagatgctga agatcagttg ggtgcacgag tgggttacat cgaactggat    5040
ctcaacagcg gtaagatcct tgagagtttt cgccccgaag aacgttttcc aatgatgagc    5100
acttttaaag ttctgctatg tggcgcggta ttatcccgta ttgacgccgg gcaagagcaa    5160
ctcggtcgcc gcatacacta ttctcagaat gacttggttg agtactcacc agtcacagaa    5220
aagcatctta cggatggcat gacagtaaga gaattatgca gtgctgccat aaccatgagt    5280
gataacactg cggccaactt acttctgaca acgatcggag gaccgaagga gctaaccgct    5340
ttttttgcaca acatggggga tcatgtaact cgccttgatc gttgggaacc ggagctgaat    5400
gaagccatac caaacgacga gcgtgacacc acgatgcctg tagcaatggc aacaacgttg    5460
cgcaaactat taactggcga actacttact ctagcttccc ggcaacaatt aatagactgg    5520
atggaggcgg ataaagttgc aggaccactt ctgcgctcgg cccttccggc tggctggttt    5580
attgctgata aatctggagc cggtgagcgt gggtctcgcg gtatcattgc agcactgggg    5640
ccagatggta agccctcccg tatcgtagtt atctacacga cggggagtca ggcaactatg    5700
gatgaacgaa atagacagat cgctgagata ggtgcctcac tgattaagca ttggtaactg    5760
tcagaccaag tttactcata tatactttag attgatttaa aacttcattt ttaatttaaa    5820
aggatctagg tgaagatcct tttgataat ctcatgacca aaatccctta acgtgagttt    5880
tcgttccact gagcgtcaga ccccgtagaa aagatcaaag gatcttcttg agatcctttt    5940
tttctgcgcg taatctgctg cttgcaaaca aaaaaaccac cgctaccagc ggtggtttgt    6000
ttgccggatc aagagctacc aactcttttt ccgaaggtaa ctggcttcag cagagcgcag    6060
ataccaaata ctgtccttct agtgtagccg tagttaggcc accacttcaa gaactctgta    6120
gcaccgccta catacctcgc tctgctaatc ctgttaccag tggctgctgc cagtggcgat    6180
aagtcgtgtc ttaccgggtt ggactcaaga cgatagttac cggataaggc gcagcggtcg    6240
```

```
ggctgaacgg ggggttcgtg cacacagccc agcttggagc gaacgaccta caccgaactg    6300
agatacctac agcgtgagct atgagaaagc gccacgcttc ccgaagggag aaaggcggac    6360
aggtatccgg taagcggcag ggtcggaaca ggagagcgca cgagggagct tccaggggga    6420
aacgcctggt atctttatag tcctgtcggg tttcgccacc tctgacttga gcgtcgattt    6480
ttgtgatgct cgtcaggggg cggagccta tggaaaaacg ccagcaacgc ggccttttta    6540
cggttcctgg cctttttgctg gccttttgct cacatgttct ttcctgcgtt atccctgat    6600 tctgtggata accgtattac cgcctttgag tgagctgata ccgctcgccg cagccgaacg    6660
accgagcgca gcgagtcagt gagcgaggaa gcggaaga                           6698
```

<210> SEQ ID NO 10
<211> LENGTH: 1765
<212> TYPE: DNA
<213> ORGANISM: artificial sequence
<220> FEATURE:
<223> OTHER INFORMATION: part p362 plasmid containing F gene and H6 promoter

<400> SEQUENCE: 10

```
ttctttattc tatacttaaa aagtgaaaat aaatacaaag gttcttgagg gttgtgttaa      60
attgaaagcg agaaataatc ataaattatt tcattatcgc gatatccgtt aagtttgtat     120
cgtaatggcc acccaggagg tgcgcctgaa gtgcctgctg tgtggcatca tcgtgctggt     180
gctgagcctg gagggactgg gaatcctgca ctacgaaaaa ctgtccaaga tcggcctggt     240 gaagggatc acccggaagt ataaaatcaa gagcaatccc ctgacaaagg acatcgtgat     300
caaaatgatc cctaatgtga gcaacgtgtc caagtgcacc ggcacagtga tggagaacta     360
caaatctagg ctgaccggga tcctgagccc tatcaaggga gccatcgaac tgtataacaa     420
taacacacat gacctggtgg gcgatgtgaa actggccggg gtggtcatgg ccggaatcgc     480
tatcggcatc gctaccgctg ctcagatcac agctggagtg gctctgtacg aggccatgaa     540
gaatgctgac aatatcaaca aactgaagag ctccatcgag tccaccaacg aagccgtggt     600
gaagctgcag gagaccgctg aaaaaacagt gtacgtgctg acagccctgc aggactatat     660
caataccaac ctggtgccaa caatcgatca gatcagctgt aagcagaccg aactggccct     720
ggacctggct ctgtctaaat acctgagcga tctgctgttc gtgtttggcc caaatctgca     780 ggatccgtg tccaactcta tgaccatcca ggccatctcc caggctttcg gcgggaacta     840
cgagaccctg ctgaggacac tggggtatgc caccgaggac tttgacgatc tgctggaaag     900
cgattccatc gctggacaga tcgtgtacgt ggacctgtct agctactata tcatcgtgag     960
agtgtacttc ccaatcctga ccgagatcca gcaggcctat gtgcaggaac tgctgccgt    1020 gagcttcaat aacgataatt ccgagtggat ctctatcgtg cctaactttg tgctgatccg    1080
caataccctg atctctaaca tcgaagtgaa gtactgcctg atcacaaaga aaagcgtgat    1140
ctgtaaccag gactatgcca ccccatgac agctagcgtg cggagtgcc tgaccggatc    1200 caccgataag tgtcctaggg aactggtggt gtcctctcac gtgccaagat cgccctgtc    1260 tggaggcgtg ctgtttgcta actgcatcag cgtgacctgc cagtgtcaga ccacaggcag    1320
agccatctct cagagcgggg agcagacact gctgatgatc gacaatacca catgtaccac    1380
agtggtgctg ggcaacatca tcatctccct ggggaagtac ctgggatcta tcaattataa    1440
ctccgaatct atcgccgtgg ggccccctgt gtacaccgac aaagtggaca tcagcagcca    1500
gatctctagc atgaatcaga gcctgcagca gtccaaagac tatatcaagg aggcccagaa    1560
```

-continued

```
aatcctggat accgtgaacc catctctgat cagcatgctg tccatgatca tcctgtacgt   1620
gctgtccatc gccgctctgt gcatcggact gatcaccttc atcagctttg tgatcgtgga   1680
gaagaaacgc ggcaattact cccggctgga cgataggcag gtgagacccg tgtctaacgg   1740
agacctgtac tatatcggca cctga                                          1765
```

<210> SEQ ID NO 11
<211> LENGTH: 3942
<212> TYPE: DNA
<213> ORGANISM: artificial sequence
<220> FEATURE:
<223> OTHER INFORMATION: part p362 plasmid containing F gene, H6
      promoter and C5 arms

<400> SEQUENCE: 11

```
ggaaacagct atgaccatga ttacgaattg cggccgcaat tctgaatgtt aaatgttata     60
ctttggatga agctataaat atgcattgga aaataatcc atttaaagaa aggattcaaa    120
tactacaaaa cctaagcgat aatatgttaa ctaagcttat tcttaacgac gctttaaata    180
tacacaaata aacataattt ttgtataacc taacaaataa ctaaaacata aaataataa     240 aaggaaatgt aatatcgtaa ttattttact caggaatggg gttaaatatt tatatcacgt    300
gtatatctat actgttatcg tatactcttt acaattacta ttacgaatat gcaagagata    360
ataagattac gtatttaaga gaatcttgtc atgataattg ggtacgacat agtgataaat    420
gctatttcgc atcgttacat aaagtcagtt ggaaagatgg atttgacaga tgtaacttaa    480
taggtgcaaa aatgttaaat aacagcattc tatcggaaga taggatacca gttatattat    540
acaaaaatca ctggttggat aaaacagatt ctgcaatatt cgtaaaagat gaagattact    600
gcgaatttgt aaactatgac aataaaaagc catttatctc aacgacatcg tgtaattctt    660
ccatgtttta tgtatgtgtt tcagatatta tgagattact ataaactttt tgtatactta    720
tattccgtaa actatattaa tcatgaagaa atgaaaaag tatagaagct gttcacgagc    780
ggttgttgaa acaacaaaa ttatacattc aagatggctt acatatacgt ctgtgaggct    840
atcatggata atgacaatgc atctctaaat aggttttgg acaatggatt cgaccctaac    900
acggaatatg gtactctaca atctcctctt gaaatggctg taatgttcaa gaataccgag    960
gctataaaaa tcttgatgag gtatggagct aaacctgtag ttactgaatg cacaacttct   1020
tgtctgcatg atgcggtgtt gagagacgac tacaaaatag tgaaagatct gttgaagaat   1080
aactatgtaa acaatgttct ttacagcgga ggctttactc ctttgtgttt ggcagcttac   1140
cttaacaaag ttaatttggt taaacttcta ttggctcatt cggcggatgt agatatttca   1200
aacacggatc ggttaactcc tctacatata gccgtatcaa ataaaaattt aacaatggtt   1260
aaacttctat tgaacaaagg tgctgatact gacttgctgg ataacatggg acgtactcct   1320
ttaatgatcg ctgtacaatc tggaaatatt gaaatatgta gcacactact aaaaaaaat   1380 aaaatgtcca gaactgggaa aaattgatct tgccagctgt aattcatggt agaaaagaag   1440
tgctcaggct acttttcaac aaaggagcag atgtaaacta catctttgaa agaaatggaa   1500
aatcatatac tgttttggaa ttgattaaag aaagttactc tgagcacaa aagaggtagc   1560 tgaagtggta ctctcaaagg tacgtgacta attagctata aaaaggatcc gggttaatta   1620
attagtcatc aggcagggcg agaacgagac tatctgctcg ttaattaatt agagcttctt   1680
tattctatac ttaaaaagtg aaaataaata caaaggttct tgagggttgt gttaaattga   1740
aagcgagaaa taatcataaa ttatttcatt atcgcgatat ccgttaagtt tgtatcgtaa   1800
```

```
tggccaccca ggaggtgcgc ctgaagtgcc tgctgtgtgg catcatcgtg ctggtgctga    1860
gcctggaggg actgggaatc ctgcactacg aaaaactgtc caagatcggc ctggtgaagg    1920
ggatcacccg gaagtataaa atcaagagca atcccctgac aaaggacatc gtgatcaaaa    1980
tgatccctaa tgtgagcaac gtgtccaagt gcaccggcac agtgatggag aactacaaat    2040
ctaggctgac cgggatcctg agccctatca agggagccat cgaactgtat aacaataaca    2100
cacatgacct ggtgggcgat gtgaaactgg ccggggtggt catggccgga atcgctatcg    2160
gcatcgctac cgctgctcag atcacagctg gagtggctct gtacgaggcc atgaagaatg    2220
ctgacaatat caacaaactg aagagctcca tcgagtccac caacgaagcc gtggtgaagc    2280
tgcaggagac cgctgaaaaa acagtgtacg tgctgacagc cctgcaggac tatatcaata    2340
ccaacctggt gccaacaatc gatcagatca gctgtaagca gaccgaactg gccctggacc    2400
tggctctgtc taaatacctg agcgatctgc tgttcgtgtt tggcccaaat ctgcaggatc    2460
ccgtgtccaa ctctatgacc atccaggcca tctcccaggc tttcggcggg aactacgaga    2520
ccctgctgag gacactgggg tatgccaccg aggactttga cgatctgctg gaaagcgatt    2580
ccatcgctgg acagatcgtg tacgtggacc tgtctagcta ctatatcatc gtgagagtgt    2640
acttcccaat cctgaccgag atccagcagg cctatgtgca ggaactgctg cccgtgagct    2700
tcaataacga taattccgag tggatctcta tcgtgcctaa ctttgtgctg atccgcaata    2760
ccctgatctc taacatcgaa gtgaagtact gcctgatcac aaagaaaagc gtgatctgta    2820
accaggacta tgccaccccc atgacagcta gcgtgcggga gtgcctgacc ggatccaccg    2880
ataagtgtcc tagggaactg gtggtgtcct ctcacgtgcc aagattcgcc ctgtctggag    2940
gcgtgctgtt tgctaactgc atcagcgtga cctgccagtg tcagaccaca ggcagagcca    3000
tctctcagag cggggagcag acactgctga tgatcgacaa taccacatgt accacagtgg    3060
tgctgggcaa catcatcatc tccctgggga agtacctggg atctatcaat tataactccg    3120
aatctatcgc cgtggggccc cctgtgtaca ccgacaaagt ggacatcagc agccagatct    3180
ctagcatgaa tcagagcctg cagcagtcca aagactatat caaggaggcc cagaaaatcc    3240
tggataccgt gaacccatct ctgatcagca tgctgtccat gatcatcctg tacgtgctgt    3300
ccatcgccgc tctgtgcatc ggactgatca ccttcatcag cttttgtgatc gtggagaaga    3360 aacgcggcaa ttactcccgg ctggacgata ggcaggtgag acccgtgtct aacggagacc    3420
tgtactatat cggcacctga tttttatggt accctcgagt ctagaatcga tcccgggttt    3480
ttatgactag ttaatcacgg ccgcttataa agatctaaaa tgcataattt ctaaataatg    3540
aaaaaaagta catcatgagc aacgcgttag tatattttac aatggagatt aacgctctat    3600
accgttctat gtttattgat tcagatgatg ttttagaaaa gaaagttatt gaatatgaaa    3660
actttaatga agatgaagat gacgacgatg attattgttg taaatctgtt ttagatgaag    3720
aagatgacgc gctaaagtat actatggtta caaagtataa gtctatacta ctaatggcga    3780
cttgtgcaag aaggtatagt atagtgaaaa tgttgttaga ttatgattat gaaaaaccaa    3840
ataaatcaga tccatatcta aaggtatctc ctttgcacat aatttcatct attcctagtt    3900
tagaatacct gcagccaagc ttggcactgg ccgtcgtttt ac    3942
```

<210> SEQ ID NO 12
<211> LENGTH: 6527
<212> TYPE: DNA
<213> ORGANISM: artificial sequence
<220> FEATURE:

<223> OTHER INFORMATION: entire p362 plasmid sequence containing F gene

<400> SEQUENCE: 12

```
gcgcccaata cgcaaaccgc ctctcccgc gcgttggccg attcattaat gcagctggca        60
cgacaggttt cccgactgga aagcgggcag tgagcgcaac gcaattaatg tgagttagct      120
cactcattag gcaccccagg ctttacactt tatgcttccg gctcgtatgt tgtgtggaat      180
tgtgagcgga taacaatttc acacaggaaa cagctatgac catgattacg aattgcggcc      240
gcaattctga atgttaaatg ttatactttg gatgaagcta taaatatgca ttggaaaaat      300
aatccattta agaaaggat tcaaatacta caaaacctaa gcgataatat gttaactaag       360
cttattctta acgacgcttt aaatatacac aaataaacat aatttttgta taacctaaca      420
aataactaaa acataaaaat aataaaagga aatgtaatat cgtaattatt ttactcagga      480
atggggttaa atatttatat cacgtgtata tctatactgt tatcgtatac tctttacaat      540
tactattacg aatatgcaag agataataag attacgtatt taagagaatc ttgtcatgat      600
aattgggtac gacatagtga taaatgctat ttcgcatcgt tacataaagt cagttggaaa      660
gatggatttg acagatgtaa cttaataggt gcaaaaatgt taaataacag cattctatcg      720
gaagatagga taccagttat attatacaaa atcactggt tggataaaac agattctgca      780
atattcgtaa aagatgaaga ttactgcgaa tttgtaaact atgacaataa aaagccattt      840
atctcaacga catcgtgtaa ttcttccatg ttttatgtat gtgtttcaga tattatgaga      900
ttactataaa cttttttgtat acttatattc cgtaaactat attaatcatg aagaaaatga    960
aaagtatag aagctgttca cgagcggttg ttgaaaacaa caaaattata cattcaagat     1020
ggcttacata tacgtctgtg aggctatcat ggataatgac aatgcatctc taaataggtt    1080
tttgacaat ggattcgacc ctaacacgga atatggtact ctacaatctc tcttgaaat     1140
ggctgtaatg ttcaagaata ccgaggctat aaaaatcttg atgaggtatg gagctaaacc    1200
tgtagttact gaatgcacaa cttccttgtct gcatgatgcg gtgttgagag acgactacaa    1260
aatagtgaaa gatctgttga agaataacta tgtaaacaat gttctttaca gcggaggctt    1320
tactcctttg tgtttggcag cttaccttaa caagttaat ttggttaaac ttctattggc     1380
tcattcggcg gatgtagata tttcaaacac ggatcggtta actcctctac atatagccgt    1440
atcaaataaa aatttaacaa tggttaaact tctattgaac aaaggtgctg atactgactt    1500
gctggataac atgggacgta ctcctttaat gatcgctgta caatctggaa atattgaaat    1560
atgtagcaca ctacttaaaa aaaataaaat gtccagaact gggaaaaatt gatcttgcca    1620
gctgtaattc atggtagaaa agaagtgctc aggctacttt tcaacaaagg agcagatgta    1680
aactacatct ttgaaagaaa tggaaaatca tatactgttt tggaattgat taagaaaagt    1740
tactctgaga cacaaaagag gtagctgaag tggtactctc aaaggtacgt gactaattag    1800
ctataaaaag gatccgggtt aattaattag tcatcaggca gggcgagaac gagactatct    1860
gctcgttaat taattagagc ttcttttattc tatacttaaa aagtgaaaat aaatacaaag    1920
gttcttgagg gttgtgttaa attgaaagcg agaaataatc ataaattatt tcattatcgc    1980
gatatccgtt aagtttgtat cgtaatggcc acccaggagg tgcgcctgaa gtgcctgctg    2040
tgtggcatca tcgtgctggt gctgagcctg gagggactgg gaatcctgca ctacgaaaaa    2100
ctgtccaaga tcggcctggt gaagggatc acccggaagt ataaaatcaa gagcaatccc    2160
ctgacaaagg acatcgtgat caaaatgatc cctaatgtga gcaacgtgtc caagtgcacc    2220
ggcacagtga tggagaacta caaatctagg ctgaccggga tcctgagccc tatcaaggga    2280
```

```
gccatcgaac tgtataacaa taacacacat gacctggtgg gcgatgtgaa actggccggg    2340
gtggtcatgg ccggaatcgc tatcggcatc gctaccgctg ctcagatcac agctggagtg    2400
gctctgtacg aggccatgaa gaatgctgac aatatcaaca aactgaagag ctccatcgag    2460
tccaccaacg aagccgtggt gaagctgcag gagaccgctg aaaaaacagt gtacgtgctg    2520
acagccctgc aggactatat caataccaac ctggtgccaa caatcgatca gatcagctgt    2580
aagcagaccg aactggccct ggacctggct ctgtctaaat acctgagcga tctgctgttc    2640
gtgtttggcc caaatctgca ggatcccgtg tccaactcta tgaccatcca ggccatctcc    2700
caggcttccg gcgggaacta cgagaccctg ctgaggacac tggggtatgc caccgaggac    2760
tttgacgatc tgctggaaag cgattccatc gctggacaga tcgtgtacgt ggacctgtct    2820
agctactata tcatcgtgag agtgtacttc ccaatcctga ccgagatcca gcaggcctat    2880
gtgcaggaac tgctgcccgt gagcttcaat aacgataatt ccgagtggat ctctatcgtg    2940
cctaactttg tgctgatccg caataccctg atctctaaca tcgaagtgaa gtactgcctg    3000
atcacaaaga aaagcgtgat ctgtaaccag gactatgcca cccccatgac agctagcgtg    3060
cgggagtgcc tgaccggatc caccgataag tgtcctaggg aactggtggt gtcctctcac    3120
gtgccaagat tcgccctgtc tggaggcgtg ctgtttgcta actgcatcag cgtgacctgc    3180
cagtgtcaga ccacaggcag agccatctct cagagcgggg agcagacact gctgatgatc    3240
gacaatacca catgtaccac agtggtgctg ggcaacatca tcatctccct ggggaagtac    3300
ctgggatcta tcaattataa ctccgaatct atcgccgtgg ggcccctgt gtacaccgac    3360 aaagtggaca tcagcagcca gatctctagc atgaatcaga gcctgcagca gtccaaagac    3420
tatatcaagg aggcccagaa aatcctggat accgtgaacc catctctgat cagcatgctg    3480
tccatgatca tcctgtacgt gctgtccatc gccgctctgt gcatcggact gatcaccttc    3540
atcagctttg tgatcgtgga gaagaaacgc ggcaattact cccggctgga cgataggcag    3600
gtgagacccg tgtctaacgg agacctgtac tatatcggca cctgatttt atggtaccct    3660 cgagtctaga atcgatcccg ggttttatg actagttaat cacggccgct ataaagatc    3720 taaaatgcat aatttctaaa taatgaaaaa aagtacatca tgagcaacgc gttagtatat    3780
tttacaatgg agattaacgc tctataccgt tctatgttta ttgattcaga tgatgtttta    3840
gaaaagaaag ttattgaata tgaaaacttt aatgaagatg aagatgacga cgatgattat    3900
tgttgtaaat ctgttttaga tgaagaagat gacgcgctaa agtatactat ggttacaaag    3960
tataagtcta tactactaat ggcgacttgt gcaagaaggt atagtatagt gaaaatgttg    4020
ttagattatg attatgaaaa accaaataaa tcagatccat atctaaaggt atctcctttg    4080
cacataattt catctattcc tagtttagaa tacctgcagc caagcttggc actggccgtc    4140
gttttacaac gtcgtgactg ggaaaaccct ggcgttaccc aacttaatcg ccttgcagca    4200
catccccctt tcgccagctg gcgtaatagc gaagaggccc gcaccgatcg cccttcccaa    4260
cagttgcgca gcctgaatgg cgaatggcgc ctgatgcggt attttctcct tacgcatctg    4320
tgcggtattt cacaccgcat atggtgcact ctcagtacaa tctgctctga tgccgcatag    4380
ttaagccagc cccgacaccc gccaacaccc gctgacgcgc cctgacgggc ttgtctgctc    4440
ccggcatccg cttacagaca agctgtgacc gtctccggga gctgcatgtg tcagaggttt    4500
tcaccgtcat caccgaaacg cgcgagacga aagggcctcg tgatacgcct atttttatag    4560
gttaatgtca tgataataat ggtttcttag acgtcaggtg gcacttttcg gggaaatgtg    4620
```

```
cgcggaaccc ctatttgttt attttttctaa atacattcaa atatgtatcc gctcatgaga    4680
caataaccct gataaatgct tcaataatat tgaaaaagga agagtatgag tattcaacat    4740
ttccgtgtcg cccttattcc cttttttgcg catttttgcc ttcctgtttt tgctcaccca    4800
gaaacgctgg tgaaagtaaa agatgctgaa gatcagttgg gtgcacgagt gggttacatc    4860
gaactggatc tcaacagcgg taagatcctt gagagttttc gccccgaaga acgttttcca    4920
atgatgagca cttttaaagt tctgctatgt ggcgcggtat tatcccgtat tgacgccggg    4980
caagagcaac tcggtcgccg catacactat tctcagaatg acttggttga gtactcacca    5040
gtcacagaaa agcatcttac ggatggcatg acagtaagag aattatgcag tgctgccata    5100
accatgagtg ataacactgc ggccaactta cttctgacaa cgatcggagg accgaaggag    5160
ctaaccgctt ttttgcacaa catgggggat catgtaactc gccttgatcg ttgggaaccg    5220
gagctgaatg aagccatacc aaacgacgag cgtgacacca cgatgcctgt agcaatggca    5280
acaacgttgc gcaaactatt aactggcgaa ctacttactc tagcttcccg gcaacaatta    5340
atagactgga tggaggcgga taaagttgca ggaccacttc tgcgctcggc ccttccggct    5400
ggctggttta ttgctgataa atctggagcc ggtgagcgtg ggtctcgcgg tatcattgca    5460
gcactggggc cagatggtaa gccctcccgt atcgtagtta tctacacgac ggggagtcag    5520
gcaactatgg atgaacgaaa tagacagatc gctgagatag gtgcctcact gattaagcat    5580
tggtaactgt cagaccaagt ttactcatat atactttaga ttgatttaaa acttcattttt    5640 taatttaaaa ggatctaggt gaagatcctt tttgataatc tcatgaccaa aatcccttaa    5700
cgtgagtttt cgttccactg agcgtcagac cccgtagaaa agatcaaagg atcttcttga    5760 gatcctttt ttctgcgcgt aatctgctgc ttgcaaacaa aaaaaccacc gctaccagcg    5820
gtggtttgtt tgccggatca agagctacca actctttttc cgaaggtaac tggcttcagc    5880
agagcgcaga taccaaatac tgtccttcta gtgtagccgt agttaggcca ccacttcaag    5940
aactctgtag caccgcctac atacctcgct ctgctaatcc tgttaccagt ggctgctgcc    6000
agtggcgata agtcgtgtct taccgggttg gactcaagac gatagttacc ggataaggcg    6060
cagcggtcgg gctgaacggg gggttcgtgc acacagccca gcttggagcg aacgacctac    6120
accgaactga gatacctaca gcgtgagcta tgagaaagcg ccacgcttcc cgaagggaga    6180
aaggcggaca ggtatccggt aagcggcagg gtcggaacag gagagcgcac gagggagctt    6240
ccagggggaa acgcctggta tctttatagt cctgtcgggt ttcgccacct ctgacttgag    6300
cgtcgatttt tgtgatgctc gtcaggggg cggagcctat ggaaaaacgc cagcaacgcg    6360
gcctttttac ggttcctggc cttttgctgg ccttttgctc acatgttctt tcctgcgtta    6420
tcccctgatt ctgtggataa ccgtattacc gcctttgagt gagctgatac cgctcgccgc    6480
agccgaacga ccgagcgcag cgagtcagtg agcgaggaag cggaaga              6527
```

<210> SEQ ID NO 13
<211> LENGTH: 20
<212> TYPE: DNA
<213> ORGANISM: artificial sequence
<220> FEATURE:
<223> OTHER INFORMATION: HenG.1F primer

<400> SEQUENCE: 13
ggctctgacc gacaaaatcg                                              20

<210> SEQ ID NO 14
<211> LENGTH: 20

-continued

```
<212> TYPE: DNA
<213> ORGANISM: artificial sequence
<220> FEATURE:
<223> OTHER INFORMATION: HenG.1R primer
<400> SEQUENCE: 14
gaactgcagg atgatgtccc 20

<210> SEQ ID NO 15
<211> LENGTH: 25
<212> TYPE: DNA
<213> ORGANISM: artificial sequence
<220> FEATURE:
<223> OTHER INFORMATION: C5R.1F primer
<400> SEQUENCE: 15
attctatcgg aagataggat accag 25

<210> SEQ ID NO 16
<211> LENGTH: 25
<212> TYPE: DNA
<213> ORGANISM: artificial sequence
<220> FEATURE:
<223> OTHER INFORMATION: C5L.2R primer
<400> SEQUENCE: 16
ggagatacct ttagatatgg atctg 25

<210> SEQ ID NO 17
<211> LENGTH: 20
<212> TYPE: DNA
<213> ORGANISM: artificial sequence
<220> FEATURE:
<223> OTHER INFORMATION: HenF.1F primer
<400> SEQUENCE: 17
ccatcgaact gtataacaat 20

<210> SEQ ID NO 18
<211> LENGTH: 20
<212> TYPE: DNA
<213> ORGANISM: artificial sequence
<220> FEATURE:
<223> OTHER INFORMATION: HenF.1R primer
<400> SEQUENCE: 18
ggagatgatg atgttgccca 20

<210> SEQ ID NO 19
<211> LENGTH: 1641
<212> TYPE: DNA
<213> ORGANISM: artificial sequence
<220> FEATURE:
<223> OTHER INFORMATION: DNA encoding Nipah F protein
<400> SEQUENCE: 19
atggtagtta tacttgacaa gagatgttat tgtaatcttt taatattgat tttgatgatc 60
tcggagtgta gtgttgggat tctacattat gagaaattga gtaaaattgg acttgtcaaa 120
ggagtaacaa gaaaatacaa gattaaaagc aatcctctca caaaagacat tgttataaaa 180
atgattccga atgtgtcgaa catgtctcag tgcacaggga gtgtcatgga aaattataaa 240
acacgattaa acggtatctt aacacctata aagggagcgt tagagatcta caaaaacaac 300
actcatgacc ttgtcggtga tgtgagatta gccggagtta taatggcagg agttgctatt 360

```
gggattgcaa ccgcagctca aatcactgca ggtgtagcac tatatgaggc aatgaagaat    420
gctgacaaca tcaacaaact caaaagcagc attgaatcaa ctaatgaagc tgtcgttaaa    480
cttcaagaga ctgcagaaaa gacagtctat gtgctgactg ctctacagga ttacattaat    540
actaatttag taccgacaat tgacaagata agctgcaaac agacagaact ctcactagat    600
ctggcattat caaagtacct ctctgatttg ctttttgtat ttggccccaa ccttcaagac    660
ccagtttcta attcaatgac tatacaggct atatctcagg cattcggtgg aaattatgaa    720
acactgctaa gaacattggg ttacgctaca gaagactttg atgatcttct agaaagtgac    780
agcataacag tcaaatcat ctatgttgat ctaagtagct actatataat tgtcagggtt    840
tattttccta ttctgactga aattcaacag gcctatatcc aagagttgtt accagtgagc    900
ttcaacaatg ataattcaga atggatcagt attgtcccaa atttcatatt ggtaaggaat    960
acattaatat caaatataga gattggattt tgcctaatta caaagaggag cgtgatctgc   1020
aaccaagatt atgccacacc tatgaccaac aacatgagag aatgtttaac gggatcgact   1080
gagaagtgtc ctcgagagct ggttgtttca tcacatgttc ccagatttgc actatctaac   1140
ggggttctgt tgccaattg cataagtgtt acatgtcagt gtcaaacaac aggcagggca   1200
atctcacaat caggagaaca aactctgctg atgattgaca caccacctg tcctacagcc   1260
gtactcggta atgtgattat cagcttaggg aaatatctgg ggtcagtaaa ttataattct   1320
gaaggcattg ctatcggtcc tccagtcttt acagataaag ttgatatatc aagtcagata   1380
tccagcatga atcagtcctt acaacagtct aaggactata tcaaagaggc tcaacgactc   1440
cttgatactg ttaatccatc attaataagc atgttgtcta tgatcatact gtatgtatta   1500
tcgatcgcat cgttgtgtat agggttgatt acatttatca gttttatcat tgttgagaaa   1560
aagagaaaca cctacagcag attagaggat aggagagtca gacctacaag cagtgggat   1620
ctctactaca ttgggacata g                                              1641
```

<210> SEQ ID NO 20  
<211> LENGTH: 546  
<212> TYPE: PRT  
<213> ORGANISM: artificial sequence  
<220> FEATURE:  
<223> OTHER INFORMATION: Nipah F protein

<400> SEQUENCE: 20

```
Met Val Val Ile Leu Asp Lys Arg Cys Tyr Cys Asn Leu Leu Ile Leu
1               5                   10                  15

Ile Leu Met Ile Ser Glu Cys Ser Val Gly Ile Leu His Tyr Glu Lys
            20                  25                  30

Leu Ser Lys Ile Gly Leu Val Lys Gly Val Thr Arg Lys Tyr Lys Ile
        35                  40                  45

Lys Ser Asn Pro Leu Thr Lys Asp Ile Val Ile Lys Met Ile Pro Asn
    50                  55                  60

Val Ser Asn Met Ser Gln Cys Thr Gly Ser Val Met Glu Asn Tyr Lys
65                  70                  75                  80

Thr Arg Leu Asn Gly Ile Leu Thr Pro Ile Lys Gly Ala Leu Glu Ile
                85                  90                  95

Tyr Lys Asn Asn Thr His Asp Leu Val Gly Asp Val Arg Leu Ala Gly
            100                 105                 110

Val Ile Met Ala Gly Val Ala Ile Gly Ile Ala Thr Ala Ala Gln Ile
        115                 120                 125

Thr Ala Gly Val Ala Leu Tyr Glu Ala Met Lys Asn Ala Asp Asn Ile
```

```
                130                 135                 140
Asn Lys Leu Lys Ser Ser Ile Glu Ser Thr Asn Glu Ala Val Val Lys
145                 150                 155                 160

Leu Gln Glu Thr Ala Glu Lys Thr Val Tyr Val Leu Thr Ala Leu Gln
                165                 170                 175

Asp Tyr Ile Asn Thr Asn Leu Val Pro Thr Ile Asp Lys Ile Ser Cys
                180                 185                 190

Lys Gln Thr Glu Leu Ser Leu Asp Leu Ala Leu Ser Lys Tyr Leu Ser
                195                 200                 205

Asp Leu Leu Phe Val Phe Gly Pro Asn Leu Gln Asp Pro Val Ser Asn
                210                 215                 220

Ser Met Thr Ile Gln Ala Ile Ser Gln Ala Phe Gly Gly Asn Tyr Glu
225                 230                 235                 240

Thr Leu Leu Arg Thr Leu Gly Tyr Ala Thr Glu Asp Phe Asp Asp Leu
                245                 250                 255

Leu Glu Ser Asp Ser Ile Thr Gly Gln Ile Ile Tyr Val Asp Leu Ser
                260                 265                 270

Ser Tyr Tyr Ile Ile Val Arg Val Tyr Phe Pro Ile Leu Thr Glu Ile
                275                 280                 285

Gln Gln Ala Tyr Ile Gln Glu Leu Leu Pro Val Ser Phe Asn Asn Asp
290                 295                 300

Asn Ser Glu Trp Ile Ser Ile Val Pro Asn Phe Ile Leu Val Arg Asn
305                 310                 315                 320

Thr Leu Ile Ser Asn Ile Glu Ile Gly Phe Cys Leu Ile Thr Lys Arg
                325                 330                 335

Ser Val Ile Cys Asn Gln Asp Tyr Ala Thr Pro Met Thr Asn Asn Met
                340                 345                 350

Arg Glu Cys Leu Thr Gly Ser Thr Glu Lys Cys Pro Arg Glu Leu Val
                355                 360                 365

Val Ser Ser His Val Pro Arg Phe Ala Leu Ser Asn Gly Val Leu Phe
370                 375                 380

Ala Asn Cys Ile Ser Val Thr Cys Gln Cys Gln Thr Thr Gly Arg Ala
385                 390                 395                 400

Ile Ser Gln Ser Gly Glu Gln Thr Leu Leu Met Ile Asp Asn Thr Thr
                405                 410                 415

Cys Pro Thr Ala Val Leu Gly Asn Val Ile Ile Ser Leu Gly Lys Tyr
                420                 425                 430

Leu Gly Ser Val Asn Tyr Asn Ser Glu Gly Ile Ala Ile Gly Pro Pro
                435                 440                 445

Val Phe Thr Asp Lys Val Asp Ile Ser Ser Gln Ile Ser Ser Met Asn
                450                 455                 460

Gln Ser Leu Gln Gln Ser Lys Asp Tyr Ile Lys Glu Ala Gln Arg Leu
465                 470                 475                 480

Leu Asp Thr Val Asn Pro Ser Leu Ile Ser Met Leu Ser Met Ile Ile
                485                 490                 495

Leu Tyr Val Leu Ser Ile Ala Ser Leu Cys Ile Gly Leu Ile Thr Phe
                500                 505                 510

Ile Ser Phe Ile Ile Val Glu Lys Lys Arg Asn Thr Tyr Ser Arg Leu
                515                 520                 525

Glu Asp Arg Arg Val Arg Pro Thr Ser Ser Gly Asp Leu Tyr Tyr Ile
530                 535                 540

Gly Thr
545
```

<210> SEQ ID NO 21
<211> LENGTH: 1809
<212> TYPE: DNA
<213> ORGANISM: artificial sequence
<220> FEATURE:
<223> OTHER INFORMATION: DNA encoding Nipah G protein

<400> SEQUENCE: 21
atgccggcag aaaacaagaa agttagattc gaaaatacta cttcagacaa agggaaaatt 60
cctagtaaag ttattaagag ctactacgga accatggaca ttaagaaaat aaatgaagga 120
ttattggaca gcaaaatatt aagtgctttc aacacagtaa tagcattgct tggatctatc 180
gtgatcatag tgatgaatat aatgatcatc caaaattaca caagatcaac agacaatcag 240
gccgtgatca aagatgcgtt gcagggtatc caacagcaga tcaaagggct tgctgacaaa 300
atcggcacag agatagggcc caaagtatca ctgattgaca catccagtac cattactatc 360
ccagctaaca ttgggctgtt aggttcaaag atcagccagt cgactgcaag tataaatgag 420
aatgtgaatg aaaaatgcaa attcacactg cctcccttga aaatccacga atgtaacatt 480
tcttgtccta acccactccc ttttagagag tataggccac agacagaagg ggtgagcaat 540
ctagtaggat tacctaataa tatttgcctg caaaagacat ctaatcagat attgaagcca 600
aagctgattt catacacttt acccgtagtc ggtcaaagtg gtacctgtat cacagaccca 660
ttgctggcta tggacgaggg ctattttgca tatagccacc tggaaagaat cggatcatgt 720
tcaagagggg tctccaaaca aagaataata ggagttggag aggtactaga cagaggtgat 780
gaagttcctt ctttatttat gaccaatgtc tggaccccac caaatccaaa caccgtttac 840
cactgtagtg ctgtatacaa caatgaattc tattatgtac tttgtgcagt gtcaactgtt 900
ggagacccta ttctgaatag cacctactgg tccggatctc taatgatgac ccgtctagct 960
gtgaaaccca agagtaatgg tgggggttac aatcaacatc aacttgccct acgaagtatc 1020
gagaaaggga ggtatgataa agttatgccg tatggacctt caggcatcaa acagggtgac 1080
accctgtatt ttcctgctgt aggatttttg gtcaggacag agtttaaata caatgattca 1140
aattgtccca tcacgaagtg tcaatacagt aaacctgaaa attgcaggct atctatgggg 1200
attagaccaa acagccatta tatccttcga tctggactat taaaatacaa tctatcagat 1260
ggggagaacc ccaaagttgt attcattgaa atatctgatc aaagattatc tattggatct 1320
cctagcaaaa tctatgattc tttgggtcaa cctgttttct accaagcgtc attttcatgg 1380
gatactatga ttaaatttgg agatgttcta acagtcaacc ctctggttgt caattggcgt 1440
aataacacgg taatatcaag acccgggcaa tcacaatgcc ctagattcaa tacatgtcca 1500
gagatctgct gggaaggagt ttataatgat gcattcctaa ttgacagaat caattggata 1560
agcgcgggtg tattccttga cagcaatcag accgcagaaa atcctgtttt tactgtattc 1620
aaagataatg aaatacttta tagggcacaa ctggcttctg aggacaccaa tgcacaaaaa 1680
acaataacta attgttttct cttgaagaat aagatttggt gcatatcatt ggttgagata 1740
tatgacacag gagacaatgt cataagaccc aaactattcg cggttaagat accagagcaa 1800
tgtacataa 1809

<210> SEQ ID NO 22
<211> LENGTH: 602
<212> TYPE: PRT
<213> ORGANISM: artificial sequence
<220> FEATURE:

-continued

<223> OTHER INFORMATION: Nipah G protein

<400> SEQUENCE: 22

```
Met Pro Ala Glu Asn Lys Lys Val Arg Phe Glu Asn Thr Thr Ser Asp
1               5                   10                  15

Lys Gly Lys Ile Pro Ser Lys Val Ile Lys Ser Tyr Tyr Gly Thr Met
            20                  25                  30

Asp Ile Lys Lys Ile Asn Glu Gly Leu Leu Asp Ser Lys Ile Leu Ser
        35                  40                  45

Ala Phe Asn Thr Val Ile Ala Leu Leu Gly Ser Ile Val Ile Ile Val
    50                  55                  60

Met Asn Ile Met Ile Ile Gln Asn Tyr Thr Arg Ser Thr Asp Asn Gln
65                  70                  75                  80

Ala Val Ile Lys Asp Ala Leu Gln Gly Ile Gln Gln Gln Ile Lys Gly
                85                  90                  95

Leu Ala Asp Lys Ile Gly Thr Glu Ile Gly Pro Lys Val Ser Leu Ile
            100                 105                 110

Asp Thr Ser Ser Thr Ile Thr Ile Pro Ala Asn Ile Gly Leu Leu Gly
        115                 120                 125

Ser Lys Ile Ser Gln Ser Thr Ala Ser Ile Asn Glu Asn Val Asn Glu
    130                 135                 140

Lys Cys Lys Phe Thr Leu Pro Pro Leu Lys Ile His Glu Cys Asn Ile
145                 150                 155                 160

Ser Cys Pro Asn Pro Leu Pro Phe Arg Glu Tyr Arg Pro Gln Thr Glu
                165                 170                 175

Gly Val Ser Asn Leu Val Gly Leu Pro Asn Asn Ile Cys Leu Gln Lys
            180                 185                 190

Thr Ser Asn Gln Ile Leu Lys Pro Lys Leu Ile Ser Tyr Thr Leu Pro
        195                 200                 205

Val Val Gly Gln Ser Gly Thr Cys Ile Thr Asp Pro Leu Leu Ala Met
    210                 215                 220

Asp Glu Gly Tyr Phe Ala Tyr Ser His Leu Glu Arg Ile Gly Ser Cys
225                 230                 235                 240

Ser Arg Gly Val Ser Lys Gln Arg Ile Ile Gly Val Gly Glu Val Leu
                245                 250                 255

Asp Arg Gly Asp Glu Val Pro Ser Leu Phe Met Thr Asn Val Trp Thr
            260                 265                 270

Pro Pro Asn Pro Asn Thr Val Tyr His Cys Ser Ala Val Tyr Asn Asn
        275                 280                 285

Glu Phe Tyr Tyr Val Leu Cys Ala Val Ser Thr Val Gly Asp Pro Ile
    290                 295                 300

Leu Asn Ser Thr Tyr Trp Ser Gly Ser Leu Met Met Thr Arg Leu Ala
305                 310                 315                 320

Val Lys Pro Lys Ser Asn Gly Gly Gly Tyr Asn Gln His Gln Leu Ala
                325                 330                 335

Leu Arg Ser Ile Glu Lys Gly Arg Tyr Asp Lys Val Met Pro Tyr Gly
            340                 345                 350

Pro Ser Gly Ile Lys Gln Gly Asp Thr Leu Tyr Phe Pro Ala Val Gly
        355                 360                 365

Phe Leu Val Arg Thr Glu Phe Lys Tyr Asn Asp Ser Asn Cys Pro Ile
    370                 375                 380

Thr Lys Cys Gln Tyr Ser Lys Pro Glu Asn Cys Arg Leu Ser Met Gly
385                 390                 395                 400
```

-continued

Ile Arg Pro Asn Ser His Tyr Ile Leu Arg Ser Gly Leu Leu Lys Tyr
                405                 410                 415

Asn Leu Ser Asp Gly Glu Asn Pro Lys Val Val Phe Ile Glu Ile Ser
            420                 425                 430

Asp Gln Arg Leu Ser Ile Gly Ser Pro Ser Lys Ile Tyr Asp Ser Leu
        435                 440                 445

Gly Gln Pro Val Phe Tyr Gln Ala Ser Phe Ser Trp Asp Thr Met Ile
    450                 455                 460

Lys Phe Gly Asp Val Leu Thr Val Asn Pro Leu Val Val Asn Trp Arg
465                 470                 475                 480

Asn Asn Thr Val Ile Ser Arg Pro Gly Gln Ser Gln Cys Pro Arg Phe
                485                 490                 495

Asn Thr Cys Pro Glu Ile Cys Trp Glu Gly Val Tyr Asn Asp Ala Phe
            500                 505                 510

Leu Ile Asp Arg Ile Asn Trp Ile Ser Ala Gly Val Phe Leu Asp Ser
        515                 520                 525

Asn Gln Thr Ala Glu Asn Pro Val Phe Thr Val Phe Lys Asp Asn Glu
    530                 535                 540

Ile Leu Tyr Arg Ala Gln Leu Ala Ser Glu Asp Thr Asn Ala Gln Lys
545                 550                 555                 560

Thr Ile Thr Asn Cys Phe Leu Leu Lys Asn Lys Ile Trp Cys Ile Ser
                565                 570                 575

Leu Val Glu Ile Tyr Asp Thr Gly Asp Asn Val Ile Arg Pro Lys Leu
            580                 585                 590

Phe Ala Val Lys Ile Pro Glu Gln Cys Thr
        595                 600

<210> SEQ ID NO 23
<211> LENGTH: 546
<212> TYPE: PRT
<213> ORGANISM: artificial sequence
<220> FEATURE:
<223> OTHER INFORMATION: Hendra F protein AAB39505

<400> SEQUENCE: 23

Met Ala Thr Gln Glu Val Arg Leu Lys Cys Leu Leu Cys Gly Ile Ile
1               5                   10                  15

Val Leu Val Leu Ser Leu Glu Gly Leu Gly Ile Leu His Tyr Glu Lys
            20                  25                  30

Leu Ser Lys Ile Gly Leu Val Lys Gly Ile Thr Arg Lys Tyr Lys Ile
        35                  40                  45

Lys Ser Asn Pro Leu Thr Lys Asp Ile Val Ile Lys Met Ile Pro Asn
    50                  55                  60

Val Ser Asn Val Ser Lys Cys Thr Gly Thr Val Met Glu Asn Tyr Lys
65                  70                  75                  80

Ser Arg Leu Thr Gly Ile Leu Ser Pro Ile Lys Gly Ala Ile Glu Leu
                85                  90                  95

Tyr Asn Asn Asn Thr His Asp Leu Val Gly Asp Val Lys Leu Ala Gly
            100                 105                 110

Val Val Met Ala Gly Ile Ala Ile Gly Ile Ala Thr Ala Ala Gln Ile
        115                 120                 125

Thr Ala Gly Val Ala Leu Tyr Glu Ala Met Lys Asn Ala Asp Asn Ile
    130                 135                 140

Asn Lys Leu Lys Ser Ser Ile Glu Ser Thr Asn Glu Ala Val Val Lys
145                 150                 155                 160

```
Leu Gln Glu Thr Ala Glu Lys Thr Val Tyr Val Leu Thr Ala Leu Gln
                165                 170                 175
Asp Tyr Ile Asn Thr Asn Leu Val Pro Thr Ile Asp Gln Ile Ser Cys
            180                 185                 190
Lys Gln Thr Glu Leu Ala Leu Asp Leu Ala Leu Ser Lys Tyr Leu Leu
        195                 200                 205
Ile Cys Ser Cys Phe Gly Pro Asn Leu Gln Asp Pro Val Ser Asn Ser
210                 215                 220
Met Thr Ile Gln Ala Ile Ser Gln Ala Phe Gly Gly Asn Tyr Glu Thr
225                 230                 235                 240
Leu Leu Arg Thr Leu Gly Tyr Ala Thr Glu Asp Phe Asp Asp Leu Leu
                245                 250                 255
Glu Ser Asp Ser Ile Thr Gly Gln Ile Val Tyr Val Asp Leu Ser Ser
            260                 265                 270
Tyr Tyr Ile Ile Val Arg Val Tyr Phe Pro Ile Leu Thr Glu Ile Gln
        275                 280                 285
Gln Ala Tyr Val Gln Glu Leu Leu Pro Val Ser Phe Asn Asn Asp Asn
290                 295                 300
Ser Glu Trp Ile Ser Ile Val Pro Asn Phe Val Leu Ile Arg Asn Thr
305                 310                 315                 320
Leu Ile Ser Asn Ile Glu Val Lys Tyr Cys Leu Ile Thr Lys Lys Ser
                325                 330                 335
Val Ile Cys Asn Gln Asp Tyr Ala Thr Pro Met Thr Ala Ser Val Arg
            340                 345                 350
Glu Cys Leu Thr Gly Ser Thr Asp Lys Cys Pro Arg Glu Leu Val Val
        355                 360                 365
Ser Ser His Val Pro Arg Phe Ala Leu Ser Gly Gly Val Leu Phe Ala
370                 375                 380
Asn Cys Ile Ser Val Thr Cys Gln Cys Gln Thr Thr Gly Arg Ala Ile
385                 390                 395                 400
Ser Gln Ser Arg Glu Gly Thr Leu Leu Met Ile Asp Asn Thr Thr Cys
                405                 410                 415
Thr Thr Val Val Leu Gly Asn Ile Ile Ile Ser Leu Pro Lys Tyr Leu
            420                 425                 430
Gly Ser Ile Lys Leu Gln Val Leu Arg Ala Leu Leu Leu Gly His Gln
        435                 440                 445
Ser Ile Gln Thr Lys Val Asp Ile Ser Ser Gln Ile Ser Ser Met Asn
450                 455                 460
Gln Ser Leu Gln Gln Ser Lys Asp Tyr Ile Lys Glu Ala Gln Lys Ile
465                 470                 475                 480
Leu Asp Thr Val Asn Pro Ser Leu Ile Ser Met Leu Ser Met Ile Ile
                485                 490                 495
Leu Tyr Val Leu Ser Ile Ala Ala Leu Cys Ile Gly Leu Ile Thr Phe
            500                 505                 510
Ile Ser Phe Val Ile Val Glu Lys Lys Arg Gly Asn Tyr Ser Arg Leu
        515                 520                 525
Asp Asp Arg Gln Val Arg Pro Val Ser Asn Gly Asp Leu Tyr Tyr Ile
530                 535                 540
Gly Thr
545

<210> SEQ ID NO 24
<211> LENGTH: 552
<212> TYPE: PRT
```

<213> ORGANISM: artificial sequence
<220> FEATURE:
<223> OTHER INFORMATION: Hendra F protein AAV80428

<400> SEQUENCE: 24

```
Met Val Val Ile Leu Asp Lys Arg Cys Tyr Cys Asn Leu Leu Ile Leu
1               5                   10                  15

Ile Leu Met Ile Ser Glu Cys Ser Val Gly Ile Leu His Tyr Glu Lys
            20                  25                  30

Leu Ser Lys Ile Gly Leu Val Lys Gly Val Thr Arg Lys Tyr Lys Ile
        35                  40                  45

Lys Ser Asn Pro Leu Thr Lys Asp Ile Val Ile Lys Met Ile Pro Asn
50                  55                  60

Val Ser Asn Met Ser Gln Cys Thr Gly Ser Val Met Glu Asn Tyr Lys
65                  70                  75                  80

Thr Arg Leu Asn Gly Ile Leu Thr Pro Ile Lys Gly Ala Leu Glu Ile
                85                  90                  95

Tyr Lys Asn Asn Thr His Asp Leu Val Gly Asp Val Arg Leu Ala Gly
            100                 105                 110

Val Ile Met Ala Gly Val Ala Ile Gly Ile Ala Thr Ala Ala Gln Ile
        115                 120                 125

Thr Ala Gly Val Ala Leu Tyr Glu Ala Met Lys Asn Ala Asp Asn Ile
130                 135                 140

Asn Lys Leu Lys Ser Ser Ile Glu Ser Thr Asn Glu Ala Val Val Lys
145                 150                 155                 160

Leu Gln Glu Thr Ala Glu Lys Thr Val Tyr Val Leu Thr Ala Leu Gln
                165                 170                 175

Asp Tyr Ile Asn Thr Asn Leu Val Pro Thr Ile Asp Lys Ile Ser Cys
            180                 185                 190

Lys Gln Thr Glu Leu Ser Leu Asp Leu Ala Leu Ser Lys Tyr Leu Ser
        195                 200                 205

Asp Leu Leu Phe Val Phe Gly Pro Asn Leu Gln Asp Pro Val Ser Asn
210                 215                 220

Ser Met Thr Ile Gln Ala Ile Ser Gln Ala Phe Gly Gly Asn Tyr Glu
225                 230                 235                 240

Thr Leu Leu Arg Thr Leu Gly Tyr Ala Thr Glu Asp Phe Asp Asp Leu
                245                 250                 255

Leu Glu Ser Asp Ser Ile Thr Gly Gln Ile Ile Tyr Val Asp Leu Ser
            260                 265                 270

Ser Tyr Tyr Ile Ile Val Arg Val Tyr Phe Pro Ile Leu Thr Glu Ile
        275                 280                 285

Gln Gln Ala Tyr Ile Gln Glu Leu Leu Pro Val Ser Phe Asn Asn Asp
290                 295                 300

Asn Ser Glu Trp Ile Ser Ile Val Pro Asn Phe Ile Leu Val Arg Asn
305                 310                 315                 320

Thr Leu Ile Ser Asn Ile Glu Ile Gly Phe Cys Leu Ile Thr Lys Arg
                325                 330                 335

Ser Val Ile Cys Asn Gln Asp Tyr Ala Thr Pro Met Thr Asn Asn Met
            340                 345                 350

Arg Glu Cys Leu Thr Gly Ser Thr Glu Lys Cys Pro Arg Glu Leu Val
        355                 360                 365

Val Ser Ser His Val Pro Arg Phe Ala Leu Ser Asn Gly Val Leu Phe
370                 375                 380

Ala Asn Cys Ile Ser Val Thr Cys Gln Cys Gln Thr Thr Gly Arg Ala
```

-continued

```
             385                 390                 395                 400
Ile Ser Gln Ser Gly Glu Gln Thr Leu Leu Met Ile Asp Asn Thr Thr
                405                 410                 415

Cys Pro Thr Ala Val Leu Gly Asn Val Ile Ile Ser Leu Gly Lys Tyr
                420                 425                 430

Leu Gly Ser Val Asn Tyr Asn Ser Glu Gly Ile Ala Ile Gly Pro Pro
                435                 440                 445

Val Phe Thr Asp Lys Val Asp Ile Ser Ser Gln Ile Ser Ser Met Asn
                450                 455                 460

Gln Ser Leu Gln Gln Ser Lys Asp Tyr Ile Lys Glu Ala Gln Arg Leu
465                 470                 475                 480

Leu Asp Thr Val Asn Pro Ser Leu Ile Ser Met Leu Ser Met Ile Ile
                485                 490                 495

Leu Tyr Val Leu Ser Ile Ala Ser Leu Cys Ile Gly Leu Ile Thr Phe
                500                 505                 510

Ile Ser Phe Ile Ile Val Glu Lys Lys Arg Asn Thr Tyr Ser Arg Leu
                515                 520                 525

Glu Asp Arg Arg Val Arg Pro Thr Ser Ser Gly Asp Leu Tyr Tyr Ile
                530                 535                 540

Gly Thr Asp Thr Tyr Arg Tyr Ile
545                 550

<210> SEQ ID NO 25
<211> LENGTH: 546
<212> TYPE: PRT
<213> ORGANISM: artificial sequence
<220> FEATURE:
<223> OTHER INFORMATION: Hendra F protein NP_112026

<400> SEQUENCE: 25

Met Val Val Ile Leu As

Asp Leu Leu Phe Val Phe Gly Pro Asn Leu Gln Asp Pro Val Ser Asn
210                 215                 220

Ser Met Thr Ile Gln Ala Ile Ser Gln Ala Phe Gly Gly Asn Tyr Glu
225                 230                 235                 240

Thr Leu Leu Arg Thr Leu Gly Tyr Ala Thr Glu Asp Phe Asp Asp Leu
            245                 250                 255

Leu Glu Ser Asp Ser Ile Thr Gly Gln Ile Ile Tyr Val Asp Leu Ser
            260                 265                 270

Ser Tyr Tyr Ile Ile Val Arg Val Tyr Phe Pro Ile Leu Thr Glu Ile
            275                 280                 285

Gln Gln Ala Tyr Ile Gln Glu Leu Leu Pro Val Ser Phe Asn Asn Asp
290                 295                 300

Asn Ser Glu Trp Ile Ser Ile Val Pro Asn Phe Ile Leu Val Arg Asn
305                 310                 315                 320

Thr Leu Ile Ser Asn Ile Glu Ile Gly Phe Cys Leu Ile Thr Lys Arg
                325                 330                 335

Ser Val Ile Cys Asn Gln Asp Tyr Ala Thr Pro Met Thr Asn Asn Met
            340                 345                 350

Arg Glu Cys Leu Thr Gly Ser Thr Glu Lys Cys Pro Arg Glu Leu Val
            355                 360                 365

Val Ser Ser His Val Pro Arg Phe Ala Leu Ser Asn Gly Val Leu Phe
370                 375                 380

Ala Asn Cys Ile Ser Val Thr Cys Gln Cys Gln Thr Thr Gly Arg Ala
385                 390                 395                 400

Ile Ser Gln Ser Gly Glu Gln Thr Leu Leu Met Ile Asp Asn Thr Thr
                405                 410                 415

Cys Pro Thr Ala Val Leu Gly Asn Val Ile Ile Ser Leu Gly Lys Tyr
            420                 425                 430

Leu Gly Ser Val Asn Tyr Asn Ser Glu Gly Ile Ala Ile Gly Pro Pro
            435                 440                 445

Val Phe Thr Asp Lys Val Asp Ile Ser Ser Gln Ile Ser Ser Met Asn
450                 455                 460

Gln Ser Leu Gln Gln Ser Lys Asp Tyr Ile Lys Glu Ala Gln Arg Leu
465                 470                 475                 480

Leu Asp Thr Val Asn Pro Ser Leu Ile Ser Met Leu Ser Met Ile Ile
                485                 490                 495

Leu Tyr Val Leu Ser Ile Ala Ser Leu Cys Ile Gly Leu Ile Thr Phe
            500                 505                 510

Ile Ser Phe Ile Ile Val Glu Lys Lys Arg Asn Thr Tyr Ser Arg Leu
            515                 520                 525

Glu Asp Arg Arg Val Arg Pro Thr Ser Ser Gly Asp Leu Tyr Tyr Ile
530                 535                 540

Gly Thr
545

<210> SEQ ID NO 26
<211> LENGTH: 546
<212> TYPE: PRT
<213> ORGANISM: artificial sequence
<220> FEATURE:
<223> OTHER INFORMATION: Hendra F protein AEQ38114

<400> SEQUENCE: 26

Met Ala Thr Gln Glu Val Arg Leu Lys Cys Leu Leu Cys Gly Ile

-continued

```
1               5                   10                  15
Val Leu Val Leu Ser Leu Glu Gly Leu Gly Ile Leu His Tyr Glu Lys
                20                  25                  30
Leu Ser Lys Ile Gly Leu Val Lys Gly Ile Thr Arg Lys Tyr Lys Ile
                35                  40                  45
Lys Ser Asn Pro Leu Thr Lys Asp Ile Val Lys Met Ile Pro Asn
 50                  55                  60
Val Ser Asn Val Ser Lys Cys Thr Gly Thr Val Met Glu Asn Tyr Lys
 65                  70                  75                  80
Ser Arg Leu Thr Gly Ile Leu Ser Pro Ile Lys Gly Ala Ile Glu Leu
                85                  90                  95
Tyr Asn Asn Asn Thr His Asp Leu Val Gly Asp Val Lys Leu Ala Gly
                100                 105                 110
Val Val Met Ala Gly Ile Ala Ile Gly Ile Ala Thr Ala Ala Gln Ile
                115                 120                 125
Thr Ala Gly Val Ala Leu Tyr Glu Ala Met Lys Asn Ala Asp Asn Ile
                130                 135                 140
Asn Lys Leu Lys Ser Ser Ile Glu Ser Thr Asn Glu Ala Val Val Lys
145                 150                 155                 160
Leu Gln Glu Thr Ala Glu Lys Thr Val Tyr Val Leu Thr Ala Leu Gln
                165                 170                 175
Asp Tyr Ile Asn Thr Asn Leu Val Pro Thr Ile Asp Gln Ile Ser Cys
                180                 185                 190
Lys Gln Thr Glu Leu Ala Leu Asp Leu Ala Leu Ser Lys Tyr Leu Ser
                195                 200                 205
Asp Leu Leu Phe Val Phe Gly Pro Asn Leu Gln Asp Pro Val Ser Asn
 210                 215                 220
Ser Met Thr Ile Gln Ala Ile Ser Gln Ala Phe Gly Gly Asn Tyr Glu
225                 230                 235                 240
Thr Leu Leu Arg Thr Leu Gly Tyr Ala Thr Glu Asp Phe Asp Asp Leu
                245                 250                 255
Leu Glu Ser Asp Ser Ile Thr Gly Gln Ile Val Tyr Val Asp Leu Ser
                260                 265                 270
Ser Tyr Tyr Ile Ile Val Arg Val Tyr Phe Pro Ile Leu Thr Glu Ile
                275                 280                 285
Gln Gln Ala Tyr Val Gln Glu Leu Leu Pro Val Ser Phe Asn Asn Asp
                290                 295                 300
Asn Ser Glu Trp Ile Ser Ile Val Pro Asn Phe Val Leu Ile Arg Asn
305                 310                 315                 320
Thr Leu Ile Ser Asn Ile Glu Val Lys Tyr Cys Leu Ile Thr Lys Lys
                325                 330                 335
Ser Val Ile Cys Asn Gln Asp Tyr Ala Thr Pro Met Thr Ala Ser Val
                340                 345                 350
Arg Glu Cys Leu Thr Gly Ser Thr Asp Lys Cys Pro Arg Glu Leu Val
                355                 360                 365
Val Ser Ser His Val Pro Arg Phe Ala Leu Ser Gly Gly Val Leu Phe
                370                 375                 380
Ala Asn Cys Ile Ser Val Thr Cys Gln Cys Gln Thr Thr Gly Arg Ala
385                 390                 395                 400
Ile Ser Gln Ser Gly Glu Gln Thr Leu Leu Met Ile Asp Asn Thr Thr
                405                 410                 415
Cys Thr Thr Val Val Leu Gly Asn Ile Ile Ile Ser Leu Gly Lys Tyr
                420                 425                 430
```

```
Leu Gly Ser Ile Asn Tyr Asn Ser Glu Ser Ile Ala Val Gly Pro Pro
            435                 440                 445

Val Tyr Thr Asp Lys Val Asp Ile Ser Ser Gln Ile Ser Ser Met Asn
    450                 455                 460

Gln Ser Leu Gln Gln Ser Lys Asp Tyr Ile Lys Glu Ala Gln Lys Ile
465                 470                 475                 480

Leu Asp Thr Val Asn Pro Ser Leu Ile Ser Met Leu Ser Met Ile Ile
                485                 490                 495

Leu Tyr Val Leu Ser Ile Ala Ala Leu Cys Ile Gly Leu Ile Thr Phe
            500                 505                 510

Ile Ser Phe Ile Ile Val Glu Lys Lys Arg Gly Asn Tyr Ser Arg Leu
            515                 520                 525

Asp Asp Arg Gln Val Arg Pro Val Ser Asn Gly Asp Leu Tyr Tyr Ile
    530                 535                 540

Gly Thr
545

<210> SEQ ID NO 27
<211> LENGTH: 546
<212> TYPE: PRT
<213> ORGANISM: artificial sequence
<220> FEATURE:
<223> OTHER INFORMATION: Hendra F protein AEB21197

<400> SEQUENCE: 27

Met Ala Thr Gln Glu Val Arg Leu Lys Cys Leu Leu Cys Gly Ile Ile
1               5                   10                  15

Val Leu Val Leu Ser Leu Glu Gly Leu Gly Ile Leu His Tyr Glu Lys
            20                  25                  30

Leu Ser Lys Ile Gly Leu Val Lys Gly Ile Thr Arg Lys Tyr Lys Ile
        35                  40                  45

Lys Ser Asn Pro Leu Thr Lys Asp Ile Val Ile Lys Met Ile Pro Asn
 50                 55                  60

Val Ser Asn Val Ser Lys Cys Thr Gly Thr Val Met Glu Asn Tyr Lys
65                  70                  75                  80

Ser Arg Leu Thr Gly Ile Leu Ser Pro Ile Lys Gly Ala Ile Glu Leu
                85                  90                  95

Tyr Asn Asn Asn Thr His Asp Leu Val Gly Asp Val Lys Leu Ala Gly
            100                 105                 110

Val Val Met Ala Gly Ile Ala Ile Gly Ile Ala Thr Ala Ala Gln Ile
        115                 120                 125

Thr Ala Gly Val Ala Leu Tyr Glu Ala Met Lys Asn Ala Asp Asn Ile
130                 135                 140

Asn Lys Leu Lys Ser Ser Ile Glu Ser Thr Asn Glu Ala Val Val Lys
145                 150                 155                 160

Leu Gln Glu Thr Ala Glu Lys Thr Val Tyr Val Leu Thr Ala Leu Gln
                165                 170                 175

Asp Tyr Ile Asn Thr Asn Leu Val Pro Thr Ile Asp Gln Ile Ser Cys
            180                 185                 190

Lys Gln Thr Glu Leu Ala Leu Asp Leu Ala Leu Ser Lys Tyr Leu Ser
        195                 200                 205

Asp Leu Leu Phe Val Phe Gly Pro Asn Leu Gln Asp Pro Val Ser Asn
    210                 215                 220

Ser Met Thr Ile Gln Ala Ile Ser Gln Ala Phe Gly Gly Asn Tyr Glu
225                 230                 235                 240
```

```
Thr Leu Leu Arg Thr Leu Gly Tyr Ala Thr Glu Asp Phe Asp Asp Leu
            245                 250                 255

Leu Glu Ser Asp Ser Ile Thr Gly Gln Ile Val Tyr Val Asp Leu Ser
            260                 265                 270

Ser Tyr Tyr Ile Ile Val Arg Val Tyr Phe Pro Ile Leu Thr Glu Ile
            275                 280                 285

Gln Gln Ala Tyr Val Gln Glu Leu Leu Pro Val Ser Phe Asn Asn Asp
            290                 295                 300

Asn Ser Glu Trp Ile Ser Ile Val Pro Asn Phe Val Leu Ile Arg Asn
305                 310                 315                 320

Thr Leu Ile Ser Asn Ile Glu Val Lys Tyr Cys Leu Ile Thr Lys Lys
            325                 330                 335

Ser Val Ile Cys Asn Gln Asp Tyr Ala Thr Pro Met Thr Ala Ser Val
            340                 345                 350

Arg Glu Cys Leu Thr Gly Ser Thr Asp Lys Cys Pro Arg Glu Leu Val
            355                 360                 365

Val Ser Ser His Val Pro Arg Phe Ala Leu Ser Gly Gly Val Leu Phe
            370                 375                 380

Ala Asn Cys Ile Ser Val Thr Cys Gln Cys Gln Thr Thr Gly Arg Ala
385                 390                 395                 400

Ile Ser Gln Ser Gly Glu Gln Thr Leu Leu Met Ile Asp Asn Thr Thr
            405                 410                 415

Cys Thr Thr Val Val Leu Gly Asn Ile Ile Ile Ser Leu Gly Lys Tyr
            420                 425                 430

Leu Gly Ser Ile Asn Tyr Asn Ser Glu Ser Ile Ala Val Gly Pro Pro
            435                 440                 445

Val Tyr Thr Asp Lys Val Asp Ile Ser Ser Gln Ile Ser Ser Met Asn
            450                 455                 460

Gln Ser Leu Gln Gln Ser Lys Asp Tyr Ile Lys Glu Ala Gln Lys Ile
465                 470                 475                 480

Leu Asp Thr Val Asn Pro Ser Leu Ile Ser Met Leu Ser Met Ile Ile
            485                 490                 495

Leu Tyr Val Leu Ser Ile Ala Ala Leu Cys Ile Gly Leu Ile Thr Phe
            500                 505                 510

Ile Ser Phe Val Ile Val Glu Lys Lys Arg Gly Asn Tyr Ser Arg Leu
            515                 520                 525

Asp Asp Arg Gln Val Arg Pro Val Ser Asn Gly Asp Leu Tyr Tyr Ile
            530                 535                 540

Gly Thr
545

<210> SEQ ID NO 28
<211> LENGTH: 611
<212> TYPE: PRT
<213> ORGANISM: artificial sequence
<220> FEATURE:
<223> OTHER INFORMATION: Hendra F protein AAV80425

<400> SEQUENCE: 28

Met Gly Pro Ala Glu Asn Lys Lys Val Arg Phe Glu Asn Thr Thr Ser
1               5                   10                  15

Asp Lys Gly Lys Ile Pro Ser Lys Val Ile Lys Ser Tyr Tyr Gly Thr
            20                  25                  30

Met Asp Ile Lys Lys Ile Asn Glu Gly Leu Leu Asp Ser Lys Ile Leu
            35                  40                  45
```

```
Ser Ala Phe Asn Thr Val Ile Ala Leu Leu Gly Ser Ile Val Ile
    50                  55                  60
Val Met Asn Ile Met Ile Gln Asn Tyr Thr Arg Ser Thr Asp Asn
65                  70                  75                  80
Gln Ala Val Ile Lys Asp Ala Leu Gln Gly Ile Gln Gln Ile Lys
                85                  90                  95
Gly Leu Ala Asp Lys Ile Gly Thr Glu Ile Gly Pro Lys Val Ser Leu
            100                 105                 110
Ile Asp Thr Ser Ser Thr Ile Thr Ile Pro Ala Asn Ile Gly Leu Leu
            115                 120                 125
Gly Ser Lys Ile Ser Gln Ser Thr Ala Ser Ile Asn Glu Asn Val Asn
            130                 135                 140
Glu Lys Cys Lys Phe Thr Leu Pro Pro Leu Lys Ile His Glu Cys Asn
145                 150                 155                 160
Ile Ser Cys Pro Asn Pro Leu Pro Phe Arg Glu Tyr Arg Pro Gln Thr
                165                 170                 175
Glu Gly Val Ser Asn Leu Val Gly Leu Pro Asn Asn Ile Cys Leu Gln
            180                 185                 190
Lys Thr Ser Asn Gln Ile Leu Lys Pro Lys Leu Ile Ser Tyr Thr Leu
            195                 200                 205
Pro Val Val Gly Gln Ser Gly Thr Cys Ile Thr Asp Pro Leu Leu Ala
210                 215                 220
Met Asp Glu Gly Tyr Phe Ala Tyr Ser His Leu Glu Arg Ile Gly Ser
225                 230                 235                 240
Cys Ser Arg Gly Val Ser Lys Gln Arg Ile Ile Gly Val Gly Glu Val
                245                 250                 255
Leu Asp Arg Gly Asp Glu Val Pro Ser Leu Phe Met Thr Asn Val Trp
            260                 265                 270
Thr Pro Pro Asn Pro Asn Thr Val Tyr His Cys Ser Ala Val Tyr Asn
            275                 280                 285
Asn Glu Phe Tyr Tyr Val Leu Cys Ala Val Ser Thr Val Gly Asp Pro
            290                 295                 300
Ile Leu Asn Ser Thr Tyr Trp Ser Gly Ser Leu Met Met Thr Arg Leu
305                 310                 315                 320
Ala Val Lys Pro Lys Ser Asn Gly Gly Gly Tyr Asn Gln His Gln Leu
                325                 330                 335
Ala Leu Arg Ser Ile Glu Lys Gly Arg Tyr Asp Lys Val Met Pro Tyr
            340                 345                 350
Gly Pro Ser Gly Ile Lys Gln Gly Asp Thr Leu Tyr Phe Pro Ala Val
            355                 360                 365
Gly Phe Leu Val Arg Thr Glu Phe Lys Tyr Asn Asp Ser Asn Cys Pro
370                 375                 380
Ile Thr Lys Cys Gln Tyr Ser Lys Pro Glu Asn Cys Arg Leu Ser Met
385                 390                 395                 400
Gly Ile Arg Pro Asn Ser His Tyr Ile Leu Arg Ser Gly Leu Leu Lys
                405                 410                 415
Tyr Asn Leu Ser Asp Gly Glu Asn Pro Lys Val Val Phe Ile Glu Ile
            420                 425                 430
Ser Asp Gln Arg Leu Ser Ile Gly Ser Pro Ser Lys Ile Tyr Asp Ser
            435                 440                 445
Leu Gly Gln Pro Val Phe Tyr Gln Ala Ser Phe Ser Trp Asp Thr Met
            450                 455                 460
```

```
Ile Lys Phe Gly Asp Val Leu Thr Val Asn Pro Leu Val Val Asn Trp
465                 470                 475                 480

Arg Asn Asn Thr Val Ile Ser Arg Pro Gly Gln Ser Gln Cys Pro Arg
                485                 490                 495

Phe Asn Thr Cys Pro Glu Ile Cys Trp Glu Gly Val Tyr Asn Asp Ala
            500                 505                 510

Phe Leu Ile Asp Arg Ile Asn Trp Ile Ser Ala Gly Val Phe Leu Asp
        515                 520                 525

Ser Asn Gln Thr Ala Glu Asn Pro Val Phe Thr Val Phe Lys Asp Asn
    530                 535                 540

Glu Ile Leu Tyr Arg Ala Gln Leu Ala Ser Glu Asp Thr Asn Ala Gln
545                 550                 555                 560

Lys Thr Ile Thr Asn Cys Phe Leu Leu Lys Asn Lys Ile Trp Cys Ile
                565                 570                 575

Ser Leu Val Glu Ile Tyr Asp Thr Gly Asp Asn Val Ile Arg Pro Lys
            580                 585                 590

Leu Phe Ala Val Lys Ile Pro Glu Gln Cys Tyr Pro Tyr Asp Val Pro
        595                 600                 605

Asp Tyr Ala
    610

<210> SEQ ID NO 29
<211> LENGTH: 604
<212> TYPE: PRT
<213> ORGANISM: artificial sequence
<220> FEATURE:
<223> OTHER INFORMATION: Hendra G protein AEB21216

<400> SEQUENCE: 29

Met Met Ala Asp Ser Lys Leu Val Ser Pro Asn Asn Asn Leu Ser Gly
1               5

```
Ile Asn Thr Arg Glu Gly Val Cys Ile Thr Asp Pro Leu Leu Ala Val
210                 215                 220
Asp Asn Gly Phe Phe Ala Tyr Ser His Leu Glu Lys Ile Gly Ser Cys
225                 230                 235                 240
Thr Arg Gly Ile Ala Lys Gln Arg Ile Ile Gly Val Gly Val Leu
            245                 250                 255
Asp Arg Gly Asp Lys Val Pro Ser Met Phe Met Thr Asn Val Trp Thr
    260                 265                 270
Pro Pro Asn Pro Ser Thr Ile His Cys Ser Ser Thr Tyr His Glu
        275                 280                 285
Asp Phe Tyr Tyr Thr Leu Cys Ala Val Ser His Val Gly Asp Pro Ile
290                 295                 300
Leu Asn Ser Thr Ser Trp Thr Glu Ser Leu Ser Leu Ile Arg Leu Ala
305                 310                 315                 320
Val Arg Pro Lys Ser Asp Ser Gly Asp Tyr Asn Gln Lys Tyr Ile Ala
            325                 330                 335
Ile Asn Lys Val Glu Arg Gly Lys Tyr Asp Lys Val Met Pro Tyr Gly
            340                 345                 350
Pro Ser Gly Ile Lys Gln Gly Asp Thr Leu Tyr Phe Pro Ala Val Gly
        355                 360                 365
Phe Leu Pro Arg Thr Glu Phe Gln Tyr Asn Asp Ser Asn Cys Pro Ile
370                 375                 380
Ile His Cys Lys Tyr Ser Lys Ala Glu Asn Cys Arg Leu Ser Met Gly
385                 390                 395                 400
Val Asn Ser Lys Ser His Tyr Ile Leu Arg Ser Gly Leu Leu Lys Tyr
            405                 410                 415
Asn Leu Ser Leu Gly Gly Asp Ile Ile Leu Gln Phe Ile Glu Ile Ala
            420                 425                 430
Asp Asn Arg Leu Thr Ile Gly Ser Pro Ser Lys Ile Tyr Asn Ser Leu
    435                 440                 445
Gly Gln Pro Val Phe Tyr Gln Ala Ser Tyr Ser Trp Asp Thr Met Ile
450                 455                 460
Lys Leu Gly Asp Val Asp Thr Val Asp Pro Leu Arg Val Gln Trp Arg
465                 470                 475                 480
Asn Asn Ser Val Ile Ser Arg Pro Gly Gln Ser Gln Cys Pro Arg Phe
            485                 490                 495
Asn Val Cys Pro Glu Val Cys Trp Glu Gly Thr Tyr Asn Asp Ala Phe
        500                 505                 510
Leu Ile Asp Arg Leu Asn Trp Val Ser Ala Gly Val Tyr Leu Asn Ser
515                 520                 525
Asn Gln Thr Ala Glu Asn Pro Val Phe Ala Val Phe Lys Asp Asn Glu
    530                 535                 540
Ile Leu Tyr Gln Val Pro Leu Ala Glu Asp Asp Thr Asn Ala Gln Lys
545                 550                 555                 560
Thr Ile Thr Asp Cys Phe Leu Leu Glu Asn Val Ile Trp Cys Ile Ser
            565                 570                 575
Leu Val Glu Ile Tyr Asp Thr Gly Asp Ser Val Ile Arg Pro Lys Leu
            580                 585                 590
Phe Ala Val Lys Ile Pro Ala Gln Cys Ser Glu Ser
        595                 600

<210> SEQ ID NO 30
<211> LENGTH: 604
<212> TYPE: PRT
```

<213> ORGANISM: artificial sequence
<220> FEATURE:
<223> OTHER INFORMATION: hendra G protein AEB21206

```
            385                 390                 395                 400
Val Asn Ser Lys Ser His Tyr Ile Leu Arg Ser G

-continued

```
          145                 150                 155                 160
    Ser Cys Pro Asn Pro Leu Pro Phe Arg Glu Tyr Arg Pro Ile Ser Gln
                    165                 170                 175
    Gly Val Ser Asp Leu Val Gly Leu Pro Asn Gln Ile Cys Leu Gln Lys
                    180                 185                 190
    Thr Thr Ser Thr Ile Leu Lys Pro Arg Leu Ile Ser Tyr Thr Leu Pro
                    195                 200                 205
    Ile Asn Thr Arg Glu Gly Val Cys Ile Thr Asp Pro Leu Leu Ala Val
        210                 215                 220
    Asp Asn Gly Phe Phe Ala Tyr Ser His Leu Glu Lys Ile Gly Ser Cys
    225                 230                 235                 240
    Thr Arg Gly Ile Ala Lys Gln Arg Ile Ile Gly Val Gly Glu Val Leu
                    245                 250                 255
    Asp Arg Gly Asp Lys Val Pro Ser Met Phe Met Thr Asn Val Trp Thr
                    260                 265                 270
    Pro Pro Asn Pro Ser Thr Ile His His Cys Ser Ser Thr Tyr His Glu
                    275                 280                 285
    Asp Phe Tyr Tyr Thr Leu Cys Ala Val Ser His Val Gly Asp Pro Ile
                    290                 295                 300
    Leu Asn Ser Thr Ser Trp Thr Glu Ser Leu Ser Leu Ile Arg Leu Ala
    305                 310                 315                 320
    Val Arg Pro Lys Ser Asp Ser Gly Asp Tyr Asn Gln Lys Tyr Ile Ala
                    325                 330                 335
    Ile Thr Lys Val Glu Arg Gly Lys Tyr Asp Lys Val Met Pro Tyr Gly
                    340                 345                 350
    Pro Ser Gly Ile Lys Gln Gly Asp Thr Leu Tyr Phe Pro Ala Val Gly
                    355                 360                 365
    Phe Leu Pro Arg Thr Glu Phe Gln Tyr Asn Asp Ser Asn Cys Pro Ile
                    370                 375                 380
    Ile His Cys Lys Tyr Ser Lys Ala Glu Asn Cys Arg Leu Ser Met Gly
    385                 390                 395                 400
    Val Asn Ser Lys Ser His Tyr Ile Leu Arg Ser Gly Leu Leu Lys Tyr
                    405                 410                 415
    Asn Leu Ser Leu Gly Gly Asp Ile Ile Leu Gln Phe Ile Glu Ile Ala
                    420                 425                 430
    Asp Asn Arg Leu Thr Ile Gly Ser Pro Ser Lys Ile Tyr Asn Ser Leu
                    435                 440                 445
    Gly Gln Pro Val Phe Tyr Gln Ala Ser Tyr Ser Trp Asp Thr Met Ile
                    450                 455                 460
    Lys Leu Gly Asp Val Asp Thr Val Asp Pro Leu Arg Val Gln Trp Arg
    465                 470                 475                 480
    Asn Asn Ser Val Ile Ser Arg Pro Gly Gln Ser Gln Cys Pro Arg Phe
                    485                 490                 495
    Asn Val Cys Pro Glu Val Cys Trp Glu Gly Ser Tyr Asn Asp Ala Phe
                    500                 505                 510
    Leu Ile Asp Arg Leu Asn Trp Val Ser Ala Gly Val Tyr Leu Asn Ser
                    515                 520                 525
    Asn Gln Thr Ala Glu Asn Pro Val Phe Ala Val Phe Lys Asp Asn Glu
                    530                 535                 540
    Ile Leu Tyr Gln Val Pro Leu Ala Glu Asp Asp Thr Asn Ala Gln Lys
    545                 550                 555                 560
    Thr Ile Thr Asp Cys Phe Leu Leu Glu Asn Val Ile Trp Cys Ile Ser
                    565                 570                 575
```

Leu Val Glu Ile Tyr Asp Thr Gly Asp Ser Val Ile Arg Pro Lys Leu
            580                 585                 590

Phe Ala Val Lys Ile Pro Ala Gln Cys Ser Glu Ser Tyr Pro Tyr Asp
            595                 600                 605

Val Pro Asp Tyr Ala
            610

<210> SEQ ID NO 32
<211> LENGTH: 604
<212> TYPE: PRT
<213> ORGANISM: artificial sequence
<220> FEATURE:
<223> OTHER INFORMATION: Hendra G protein AEQ38108

<400

-continued

```
Val Arg Pro Lys Ser Asp Ser Gly Asp Tyr Asn Gln Lys Tyr Ile Thr
            325                 330                 335

Ile Thr Lys Val Glu Arg Gly Lys Tyr Asp Lys Val Met Pro Tyr Gly
            340                 345                 350

Pro Ser Gly Ile Lys Gln Gly Asn Thr Leu Tyr Phe Pro Ala Val Gly
            355                 360                 365

Phe Leu Pro Arg Thr Glu Phe Gln Tyr Asn Asp Ser Asn Cys Pro Ile
            370                 375                 380

Ile His Cys Lys Tyr Ser Lys Ala Glu Asn Cys Arg Leu Ser Met Gly
385                 390                 395                 400

Val Asn Ser Lys Ser His Tyr Ile Leu Arg Ser Gly Leu Leu Lys Tyr
            405                 410                 415

Asn Leu Ser Leu Gly Gly Asp Ile Ile Leu Gln Phe Ile Glu Ile Ala
            420                 425                 430

Asp Asn Arg Leu Thr Ile Gly Ser Pro Ser Lys Ile Tyr Asn Ser Leu
            435                 440                 445

Gly Gln Pro Val Phe Tyr Gln Ala Ser Tyr Ser Trp Asp Thr Met Ile
            450                 455                 460

Lys Leu Gly Asp Val Asp Thr Val Asp Pro Leu Arg Val Gln Trp Arg
465                 470                 475                 480

Asn Asn Ser Val Ile Ser Arg Pro Gly Gln Ser Gln Cys Pro Arg Phe
            485                 490                 495

Asn Val Cys Pro Glu Val Cys Trp Glu Gly Thr Tyr Asn Asp Ala Phe
            500                 505                 510

Leu Ile Asp Arg Leu Asn Trp Val Ser Ala Gly Val Tyr Leu Asn Ser
            515                 520                 525

Asn Gln Thr Ala Glu Asn Pro Val Phe Ala Val Phe Lys Asp Asn Glu
            530                 535                 540

Ile Leu Tyr Gln Val Pro Leu Ala Glu Asp Thr Asn Ala Gln Lys
545                 550                 555                 560

Thr Ile Thr Asp Cys Phe Leu Leu Glu Asn Val Ile Trp Cys Ile Ser
            565                 570                 575

Leu Val Glu Ile Tyr Asp Thr Gly Asp Ser Val Ile Arg Pro Lys Leu
            580                 585                 590

Phe Ala Val Lys Ile Pro Ala Gln Cys Ser Glu Ser
            595                 600
```

<210> SEQ ID NO 33
<211> LENGTH: 604
<212> TYPE: PRT
<213> ORGANISM: artificial sequence
<220> FEATURE:
<223> OTHER INFORMATION: Hendra G protein AEQ38115

<400> SEQUENCE: 33

Met Met Ala Asp Ser Lys Leu Val Ser Leu Asn Asn Asn Leu Ser Gly
1 5 10 15

Lys Ile Lys Asp Gln Gly Lys Val Ile Lys Asn Tyr Tyr Gly Thr Met
20 25 30

Asp Ile Lys Lys Ile Asn Asp Gly Leu Leu Asp Ser Lys Ile Leu Gly
35 40 45

Ala Phe Asn Thr Val Ile Ala Leu Leu Gly Ser Ile Ile Ile Ile Val
50 55 60

Met Asn Ile Met Ile Ile Gln Asn Tyr Thr Arg Thr Thr Asp Asn Gln
65 70 75 80

```
Ala Leu Ile Lys Glu Ser Leu Gln Ser Val Gln Gln Gln Ile Lys Ala
             85                  90                  95

Leu Thr Asp Lys Ile Gly Thr Glu Ile Gly Pro Lys Val Ser Leu Ile
            100                 105                 110

Asp Thr Ser Ser Thr Ile Thr Ile Pro Ala Asn Ile Gly Leu Leu Gly
            115                 120                 125

Ser Lys Ile Ser Gln Ser Thr Ser Ser Ile Asn Glu Asn Val Asn Asp
            130                 135                 140

Lys Cys Lys Phe Thr Leu Pro Pro Leu Lys Ile His Glu Cys Asn Ile
145                 150                 155                 160

Ser Cys Pro Asn Pro Leu Pro Phe Arg Glu Tyr Arg Pro Ile Ser Gln
                165                 170                 175

Gly Val Ser Asp Leu Val Gly Leu Pro Asn Gln Ile Cys Leu Gln Lys
                180                 185                 190

Thr Thr Ser Thr Ile Leu Lys Pro Arg Leu Ile Ser Tyr Thr Leu Pro
            195                 200                 205

Ile Asn Thr Arg Glu Gly Val Cys Ile Thr Asp Pro Leu Leu Ala Val
            210                 215                 220

Asp Asn Gly Phe Phe Ala Tyr Ser His Leu Glu Lys Ile Gly Ser Cys
225                 230                 235                 240

Thr Arg Gly Ile Ala Lys Gln Arg Ile Ile Gly Val Gly Glu Val Leu
                245                 250                 255

Asp Arg Gly Asp Lys Val Pro Ser Met Phe Met Thr Asn Val Trp Thr
                260                 265                 270

Pro Pro Asn Pro Ser Thr Ile His His Cys Ser Ser Thr Tyr His Glu
            275                 280                 285

Asp Phe Tyr Tyr Thr Leu Cys Ala Val Ser His Val Gly Asp Pro Ile
            290                 295                 300

Leu Asn Ser Thr Ser Trp Thr Glu Ser Leu Ser Leu Ile Arg Leu Ala
305                 310                 315                 320

Val Arg Pro Lys Ser Asp Asn Gly Asp Tyr Asn Gln Lys Tyr Ile Ala
                325                 330                 335

Ile Thr Lys Val Glu Arg Gly Lys Tyr Asp Lys Val Met Pro Tyr Gly
            340                 345                 350

Pro Ser Gly Ile Lys Gln Gly Asp Thr Leu Tyr Phe Pro Ala Val Gly
            355                 360                 365

Phe Leu Pro Arg Thr Glu Phe Gln Tyr Asn Asp Ser Asn Cys Pro Ile
370                 375                 380

Ile His Cys Lys Tyr Ser Lys Ala Glu Asn Cys Arg Leu Ser Met Gly
385                 390                 395                 400

Val Asn Ser Lys Ser His Tyr Ile Leu Arg Ser Gly Leu Leu Lys Tyr
                405                 410                 415

Asn Leu Ser Leu Gly Gly Asp Ile Ile Leu Gln Phe Ile Glu Ile Ala
            420                 425                 430

Asp Asn Arg Leu Thr Ile Gly Ser Pro Ser Lys Ile Tyr Asn Ser Leu
            435                 440                 445

Gly Gln Pro Val Phe Tyr Gln Ala Ser Tyr Ser Trp Asp Thr Met Ile
            450                 455                 460

Lys Leu Gly Asp Val Asp Thr Val Asp Pro Leu Arg Val Gln Trp Arg
465                 470                 475                 480

Asn Asn Ser Val Ile Ser Arg Pro Gly Gln Ser Gln Cys Pro Arg Phe
                485                 490                 495
```

-continued

```
Asn Val Cys Pro Glu Val Cys Trp Glu Gly Thr Tyr Asn Asp Ala Phe
            500             505             510

Leu Ile Asp Arg Leu Asn Trp Val Ser Ala Gly Val Tyr Leu Asn Ser
        515             520             525

Asn Gln Thr Ala Glu Asn Pro Val Phe Ala Val Phe Lys Asp Asn Glu
    530             535             540

Ile Leu Tyr Gln Val Pro Leu Ala Glu Asp Asp Thr Asn Ala Gln Lys
545             550             555             560

Thr Ile Thr Asp Cys Phe Leu Leu Glu Asn Val Ile Trp Cys Ile Ser
            565             570             575

Leu Val Glu Ile Tyr Asp Thr Gly Asp Ser Val Ile Arg Pro Lys Leu
            580             585             590

Phe Ala Val Lys Ile Pro Ala Gln Cys Ser Glu Ser
        595             600
```

HENDRA VIRUS RECOMBINANT COMPOSITIONS AND USES THEREOF

CROSS-REFERENCE TO RELATED APPLICATIONS

This application is a division of, and claims benefits of, U.S. patent application Serial No. 13/478,165, filed May 23, 2012, and which claims priority to U.S. provisional patent application Serial No. 61/491,037 filed May 27, 2011.

FIELD OF THE INVENTION

The present invention relates to formulations for combating Hendra virus and Nipah virus in animals. Specifically, the present invention provides vectors that contain and express in vivo or in vitro Hendra virus F and G antigens that elicit an immune response in animals and human against Hendra virus and Nipah virus, including compositions comprising said vectors, methods of vaccination against Hendra virus and Nipah virus, and kits for use with such methods and compositions. The present invention also provides vectors that contain and express in vivo or in vitro Hendra F or G protein that elicit an immune response in animals against Hendra virus and Nipah, and compositions comprising said vectors.

BACKGROUND OF THE INVENTION

Hendra virus is the source of a recently emerging disease in animals and human. Hendra virus was first recognized in September 1994 after an outbreak of respiratory illness among twenty horses and two humans in Hendra, Queensland, Australia (Selvey L A, et al., Med J Australia 1995, 162:642-5). Thirteen horses and one human died. In 1995, a second unrelated outbreak was identified that had occurred in August 1994 in Mackay, Queensland, in which two horses died and one human became infected (Hooper P T, et al., Australian Vet J 1996; 74:244-5; Rogers R J, et al., Australia Vet J 1996; 74:243-4). Four of the seven people who contracted the virus from infected horses have died since the disease first emerged in 1994. The fatality rate has been reported at more than 70% in horses and 50% in humans.

Nipah virus is a member of the Paramyxoviridae family and is related to the Hendra virus (formerly called equine morbillivirus). The Nipah virus was initially isolated in 1999 upon examining samples from an outbreak of encephalitis and respiratory illness among adult men in Malaysia and Singapore (see, e.g., Chua et al., Lancet. 1999, 354 (9186): 1257-9 and Paton et al., Lancet. 1999 Oct. 9; 354(9186): 1253-6). The host for Nipah virus is still unknown, but flying foxes (bats of the *Pteropus* genus) are suspected to be the natural host. Infection with Nipah virus in humans has been associated with an encephalitis characterized by fever and drowsiness and more serious central nerve system disease, such as coma, seizures and inability to maintain breathing (see, e.g., Lee et al., Ann Neurol. 1999 September; 46(3): 428-32). Illness with Nipah virus begins with 3-14 days of fever and headache, followed by drowsiness and disorientation characterized by mental confusion. These signs and symptoms can progress to coma within 24-48 hours. Some patients have had a respiratory illness during the early part of their infections. Serious nerve disease with Nipah virus encephalitis has been marked by some sequelae, such as persistent convulsions and personality changes. During the Nipah virus disease outbreak in 1998-1999, about 40% of the patients with serious nerve disease who entered hospitals died from the illness (see, e.g., Lam & Chua, Clin Infect Dis. 2002 May 1; 34 Suppl 2:S48-51).

Hendra virus, like the majority of other paramyxoviruses, possess two surface glycoproteins, a fusion protein (F) and an attachment protein (G), that are involved in promotion of fusion between the viral membrane and the membrane of the target host cell. Hendra and Nipah viruses require both their attachment and fusion proteins to initiate membrane fusion (Bossart et al., J Virol. 2002; 76:11186-98). Various studies were conducted to understand the functions of the G and F proteins in virus infection. A soluble G glycoprotein of Hendra virus was constructed and showed the capability to bind to Hedra virus and Nipah virus infection-permissive cells (Bossart et al., J Virol. 2005; 79:6690-6702). Monoclonal antibodies specific for the Nipah virus fusion protein were shown to neutralize Hedra virus in vitro and protected hamsters from Hendra virus (Guillaume et al., Virology 2009; 387:459-465). A recombinant soluble Hendra G protein in CpG adjuvant was evaluated in a cat model (McEachern et al., Vaccine 2008; 26:3842-3852).

Currently there is no licensed Hendra vaccine. Therefore, there is a general need for a Hendra vaccine for the protection against Hendra virus and Nipah virus infection, prevention of the disease in animals and human and prevention of spreading of the virus to uninfected animals or human.

The invention provides a solution for optimizing the immunological and efficacious effect of Hendra virus vaccine while retaining high safety for the vaccinated animals.

SUMMARY OF THE INVENTION

An object of this invention can be any one or all of providing recombinant vectors or viruses as well as methods for making such viruses, and providing compositions and/or vaccines as well as methods for treatment and prophylaxis of infection by Hendra virus or Nipah virus.

The invention provides a recombinant vector, such as a recombinant virus, that contains and expresses at least one exogenous nucleic acid molecule and, the at least one exogenous nucleic acid molecule may comprise a nucleic acid molecule encoding an immunogen or epitope of interest from Hendra virus, such as F or G or a combination thereof.

The invention further provides compositions or vaccines comprising such an expression vector or the expression product(s) of such an expression vector. The compositions or vaccines may comprise two or more such expression vectors or the expression product(s) of such expression vectors. The invention further relates to a vaccine or composition which may comprise one or more aforementioned recombinant or expression vector a pharmaceutically or veterinarily acceptable carrier, excipient, adjuvant, or vehicle, and additionally one or more antigens. The additional antigen(s) may be Nipah virus antigen(s).

The invention further provides methods for inducing an immunological (or immunogenic) or protective response against Hendra virus or Nipah virus, as well as methods for preventing or treating the disease state(s) caused by Hendra virus or Nipah virus, comprising administering the expression vector or an expression product of the expression vector, or a composition comprising the expression vector, or a composition comprising an expression product of the expression vector.

The invention relates to expression products from the virus as well as antibodies generated from the expression products or the expression thereof in vivo and uses for such products and antibodies, e.g., in diagnostic applications. The invention also relates to a method of hyperimmunizing horses to induce polyclonal antibodies for serotherapy in animals and humans comprising at least one administration of the composition or vector of the present invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 is the table showing the SEQ ID NO assigned to the respective DNA and Protein sequences.

FIG. 2 depicts the plasmid maps of p362-Hendra G and p362-Hendra F.

FIG. 6 shows the vCP3005 (Hendra F) Western Blot result.

FIG. 7 depicts the fusion assay of vCP3004, vCP3005, and vCP3004+vCP3005.

FIGS. 8A-8C show the ELISA binding and blocking assays and SNT against Hendra.

FIGS. 9A-9C show the ELISA binding and blocking assays and SNT against Nipah.

FIGS. 11A-11J show DNA and protein sequences.

FIGS. 12A-12K show the protein and DNA sequence alignment and sequence identity percentages

DETAILED DESCRIPTION

Figure 3:
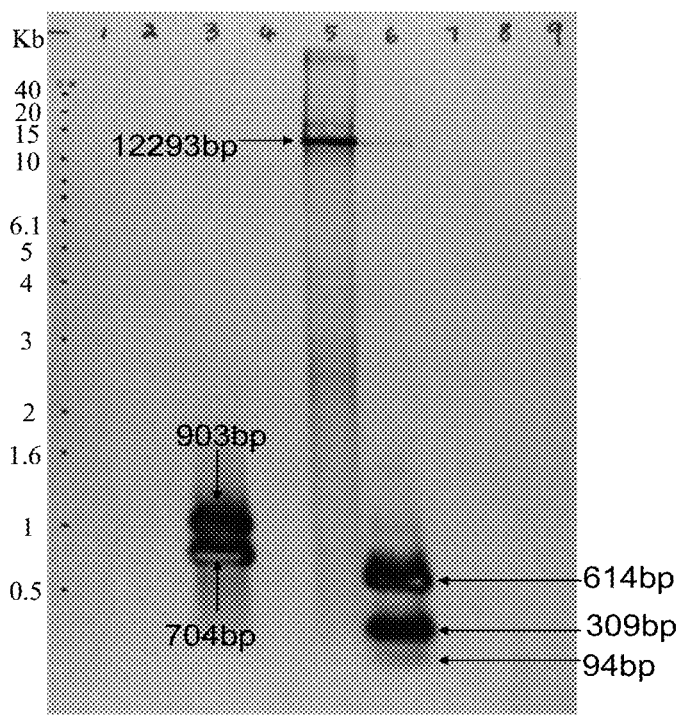
FIG. 3 shows the vCP3004 (Hendra G) Southern Blot result.

Compositions comprising one or more expression vector(s) comprising one or more polynucleotide(s) encoding one or more Hendra virus antigen(s), polypeptide(s) and fragments and variants thereof that elicit an immunogenic response in an animal or human are provided. The expression vector comprising the polynucleotide encoding Hendra virus antigen(s) or polypeptide(s) or fragments or variants may be formulated into vaccines or pharmaceutical compositions and used to elicit or stimulate a protective response in an animal or human. In one embodiment the Hendra virus antigen or polypeptide is a Hendra virus fusion protein (F), a Hendra virus attachment protein (G), or active fragment or variant thereof.

It is recognized that the polypeptides of the invention may be full length polypeptides or active fragments or variants thereof. By "active fragments" or "active variants" is intended that the fragments or variants retain the antigenic nature of the polypeptide. Thus, the present invention encompasses any Hendra virus polypeptide, antigen, epitope or immunogen that elicits an immunogenic response in an animal. The Hendra virus polypeptide, antigen, epitope or immunogen may be any Hendra virus polypeptide, antigen, epitope or immunogen, such as, but not limited to, a protein, peptide or fragment or variant thereof, that elicits, induces or stimulates a response in an animal.

A particular Hendra virus polypeptide of interest is Hendra virus fusion protein (F) and Hendra virus attachment protein (G). It is further recognized that precursors of any of these antigens can be used. The antigenic polypeptides of the invention are capable of protecting against Hendra virus. That is, they are capable of stimulating an immune response in an animal or human.

The term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "Hendra virus polypeptide or antigen" refers to any antigen or polypeptide identified in any Hendra virus strain. The antigen or polypeptide may be native to the particular Hendra virus strain. The antigen or polypeptide may be optimized from its native form. Hendra virus polypeptide or antigen include, for example, fusion protein (F), attachment protein (G), and Nucleocapsid (N) protein.

The term "immunogenic or antigenic polypeptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra.

As discussed herein, the invention encompasses active fragments and variants of the antigenic polypeptide. Thus, the term "immunogenic or antigenic polypeptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) nonpolar—alanine, valine, leucine, isoleucine, proline, phenylalanine, methionine, tryptophan; and (4) uncharged polar—glycine, asparagine, glutamine, cysteine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

By "animal" is intended mammals, birds, and the like. Animal or host as used herein includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), avian (e.g., chicken, duck, goose, turkey, quail, pheasant, parrot, finches, hawk, crow, ostrich, emu and cassowary), primate (e.g., prosimian, tarsier, monkey, gibbon, ape), ferrets, seals, and fish. The term "animal" also includes an individual animal in all stages of development, including embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Compositions

The present invention relates to a Hendra virus recombinant vaccine or composition which may comprise at least one recombinant or expression vector comprising one or more polynucleotide(s) encoding one or more Hendra virus polypeptide, antigen, epitope or immunogen. The vaccine or composition may further comprise a pharmaceutically or veterinarily acceptable carrier, excipient, adjuvant, or vehicle. The Hendra virus polypeptide, antigen, epitope or immunogen may be any Hendra virus polypeptide, antigen, epitope or immunogen, such as, but not limited to, a protein, peptide or fragment thereof, that elicits, induces or stimulates a response in an animal.

In another embodiment, the pharmaceutically or veterinarily acceptable carrier, excipient, adjuvant, or vehicle may be a water-in-oil emulsion. In yet another embodiment, the water-in-oil emulsion may be a water/oil/water (W/O/W) triple emulsion. In yet another embodiment, the pharmaceutically or veterinarily acceptable carrier, excipient, adjuvant, or vehicle may be an oil-in-water emulsion. In another embodiment, the pharmaceutically or veterinarily acceptable carriers, excipients, adjuvants, or vehicles may be polymers of acrylic or methacrylic acid, maleic anhydride and alkenyl derivative polymers.

In an embodiment, the Hendra virus polypeptide, antigen or fragment or variant thereof may be a Hendra virus F polypeptide or fragment or variant thereof. In an aspect of this embodiment, the Hendra virus F polypeptide or fragment or variant thereof is a recombinant polypeptide produced by a Hendra virus F gene. In another aspect of this embodiment, the Hendra virus F gene has at least 70% identity to the sequence as set forth in SEQ ID NO: 4 or 5. In another aspect of this embodiment, the Hendra virus F polypeptide or fragment or variant thereof has at least 80% identity to the sequence as set forth in SEQ ID NO: 6.

In another embodiment, the Hendra virus polypeptide, antigen or fragment or variant thereof may be a Hendra virus G polypeptide or fragment or variant thereof. In an aspect of this embodiment, the Hendra virus G polypeptide or fragment or variant thereof is a recombinant polypeptide produced by a Hendra virus G gene. In another aspect of this embodiment, the Hendra virus G gene has at least 70% identity to the sequence as set forth in SEQ ID NO: 1 or 2. In another aspect of this embodiment, the Hendra virus G polypeptide or fragment or variant thereof has at least 80% identity to the sequence as set forth in SEQ ID NO: 3.

Synthetic antigens are also included within the definition, for example, polyepitopes, flanking epitopes, and other recombinant or synthetically derived antigens. Immunogenic fragments, for purposes of the present invention, will usually include at least about 3 amino acids, at least about 5 amino acids, at least about 10-15 amino acids, or about 15-25 amino acids or more amino acids, of the molecule. There is no critical upper limit to the length of the fragment, which could comprise nearly the full-length of the protein sequence, or even a fusion protein comprising at least one epitope of the protein.

Accordingly, a minimum structure of a polynucleotide expressing an epitope is that it comprises or consists essentially of or consists of nucleotides encoding an epitope or antigenic determinant of a Hendra virus polypeptide. A polynucleotide encoding a fragment of a Hendra virus polypeptide may comprise or consist essentially of or consist of a minimum of 15 nucleotides, about 30-45 nucleotides, about 45-75, or at least 75, 87 or 150 consecutive or contiguous nucleotides of the sequence encoding the polypeptide. Epitope determination procedures, such as, generating overlapping peptide libraries (Hemmer et al., 1998), Pepscan (Geysen et al., 1984; Geysen et al., 1985; Van der Zee R. et al., 1989; Geysen, 1990; Multipin® Peptide Synthesis Kits de Chiron) and algorithms (De Groot et al., 1999; PCT/US2004/022605) can be used in the practice of the invention.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "purified" as used herein does not require absolute purity; rather, it is intended as a relative term. Thus, for example, a partially purified polypeptide preparation is one in which the polypeptide is more enriched than the polypeptide is in its natural environment. That is the polypeptide is separated from cellular components. By "substantially purified" is intended that at least 60%, at least 70%, at least 80%, at least 90%, at least 95%, or at least 98%, or more of the cellular components or materials have been removed. Likewise, a polypeptide may be partially purified. By "partially purified" is intended that less than 60% of the cellular components or material is removed. The same applies to polynucleotides. The polypeptides disclosed herein can be purified by any of the means known in the art.

Moreover, homologs of Hendra virus F or G polypeptides are intended to be within the scope of the present invention. As used herein, the term "homologs" includes orthologs, analogs and paralogs. The term "anologs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. For example, analogs, orthologs, and paralogs of a wild-type Hendra virus polypeptide can differ from the wild-type Hendra virus polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the wild-type Hendra virus polypeptide or polynucleotide sequences, and will exhibit a similar function.

In one embodiment, the present invention provides an expression vector comprising one or more polynucleotides encoding one or more polypeptides having at least 70%, at least 75%, at least 80%, at least 85%, at least 90%, at least 95%, 96%, 97%, 98% or 99% sequence identity to a polypeptide having a sequence as set forth in SEQ ID NO: 3 or 6. In another embodiment, the present invention provides fragments and variants of the Hendra virus F or G polypeptides identified above (SEQ ID NO: 3, 6) which may readily be prepared by one of skill in the art using well-known molecular biology techniques. Variants are homologous polypeptides having amino acid sequences at least 75%, 80%, 85%, 90%, 95%, 96%, 97%, 98%, or 99% identity to the amino acid sequences as set forth in SEQ ID NO: 3 or 6.

Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same genetic locus in those species. Any and all such nucleic acid variations and resulting amino acid polymorphisms or variations that are the result of natural allelic variation and that do not alter the functional activity of gene of interest, are intended to be within the scope of the invention.

As used herein, the term "derivative" or "variant" refers to a polypeptide, or a nucleic acid encoding a polypeptide, that has one or more conservative amino acid variations or other minor modifications such that (1) the corresponding polypeptide has substantially equivalent function when compared to the wild type polypeptide or (2) an antibody raised against the polypeptide is immunoreactive with the wild-type polypeptide. These variants or derivatives include polypeptides having minor modifications of the Hendra virus polypeptide primary amino acid sequences that may result in peptides which have substantially equivalent activity as compared to the unmodified counterpart polypeptide. Such modifications may be deliberate, as by site-directed mutagenesis, or may be spontaneous. The term "variant" further contemplates deletions, additions and substitutions to the sequence, so long as the polypeptide functions to produce an immunological response as defined herein.

An immunogenic fragment of a Hendra virus polypeptide includes at least 8, 10, 13, 14, 15, or 20 consecutive amino acids, at least 21 amino acids, at least 23 amino acids, at least 25 amino acids, or at least 30 amino acids of a Hendra virus polypeptide having a sequence as set forth in SEQ ID NO: 3, 6, or variants thereof.

In another aspect, the present invention provides an expression vector comprising a polynucleotide encoding a Hendra virus F polypeptide, such as a polynucleotide encoding a polypeptide having a sequence as set forth in SEQ ID NO: 6. In yet another aspect, the present invention provides an expression vector comprising a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 6, or a conservative variant, an allelic variant, a homolog or an immunogenic fragment comprising at least eight or at east ten consecutive amino acids of one of these polypeptides, or a combination of these polypeptides.

In yet another aspect, the present invention provides an expression vector comprising a polynucleotide encoding a Hendra virus G polypeptide, such as a polynucleotide encoding a polypeptide having a sequence as set forth in SEQ ID NO: 3. In yet another aspect, the present invention provides an expression vector comprising a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 3, or a conservative variant, an allelic variant, a homolog or an immunogenic fragment comprising at least eight or at east ten consecutive amino acids of one of these polypeptides, or a combination of these polypeptides.

In yet another aspect, the present invention provides an expression vector comprising two polynucleotides encoding a Hendra virus F polypeptide, such as a polynucleotide encoding a polypeptide having a sequence as set forth in SEQ ID NO: 6 and a Hendra virus G polypeptide, such as a polynucleotide encoding a polypeptide having a sequence as set forth in SEQ ID NO: 3.

In one embodiment the polynucleotide of the present invention includes a polynucleotide having a nucleotide sequence as set forth in SEQ ID NO: 1, 2, 4, 5, or a variant thereof. In another embodiment, the polynucleotide of the present invention includes a polynucleotide having at least 70%, at least 75%, at least 80%, at least 85%, at least 90%, at least 95%, at least 95%, 96%, 97%, 98% or 99% sequence identity to one of a polynucleotide having a sequence as set forth in SEQ ID NO: 1, 2, 4, 5, or a variant thereof.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for Hendra virus polypeptides, the DNA sequence of the Hendra virus gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of Hendra virus protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the Hendra virus polypeptide encoded by the nucleotide sequence is functionally unchanged.

The sequence identity between two amino acid sequences may be established by the NCBI (National Center for Biotechnology Information) pairwise blast and the blosum62 matrix, using the standard parameters (see, e.g., the BLAST or BLASTX algorithm available on the "National Center for Biotechnology Information" (NCBI, Bethesda, Md., USA) server, as well as in Altschul et al.).

The "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

The sequence identity or sequence similarity of two amino acid sequences, or the sequence identity between two nucleotide sequences can be determined using Vector NTI software package (Invitrogen, 1600 Faraday Ave., Carlsbad, Calif.).

The following documents provide algorithms for comparing the relative identity or homology of sequences, and additionally or alternatively with respect to the foregoing, the teachings in these references can be used for determining percent homology or identity: Needleman S B and Wunsch C D; Smith T F and Waterman M S; Smith T F, Waterman M S and Sadler J R; Feng D F and Dolittle R F; Higgins D G and Sharp P M; Thompson J D, Higgins D G and Gibson T J; and, Devereux J, Haeberlie P and Smithies O. And, without undue experimentation, the skilled artisan can consult with many other programs or references for determining percent homology.

Hybridization reactions can be performed under conditions of different stringency. Conditions that increase stringency of a hybridization reaction are well known. See for example, "Molecular Cloning: A Laboratory Manual", second edition (Sambrook et al., 1989).

The invention encompasses the Hendra virus polynucleotide(s) contained in a vector molecule or an expression vector and operably linked to a promoter element and optionally to an enhancer.

The present invention further encompasses a vaccine or composition which may comprise one or more aforementioned recombinant vector comprising one or more polynucleotides encoding one or more Hendra virus polypeptides or antigens, a pharmaceutically or veterinarily acceptable carrier, excipient, adjuvant, or vehicle. The present invention further relates to a vaccine or composition which may comprise one or more aforementioned recombinant or expression vector and additionally one or more antigens. The additional antigen(s) may be Nipah virus antigen(s). The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector needs not be capable of replication in the ultimate target cell or subject. The term includes cloning vectors and viral vectors.

The term "recombinant" means a polynucleotide with semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Elements for the expression of a Hendra virus polypeptide, antigen, epitope or immunogen are present in an inventive vector. In minimum manner, this comprises an initiation codon (ATG), a stop codon and a promoter, and optionally also a polyadenylation sequence for certain vectors such as plasmid and certain viral vectors, e.g., viral vectors other than poxviruses. When the polynucleotide encodes a polypeptide fragment, e.g. a Hendra virus polypeptide, in the vector, an ATG is placed at 5' of the reading frame and a stop codon is placed at 3'. Other elements for controlling expression may be present, such as enhancer sequences, stabilizing sequences, such as intron and signal sequences permitting the secretion of the protein.

The present invention also relates to compositions or vaccines comprising vectors. The composition or vaccine can comprise one or more vectors, e.g., expression vectors, such as in vivo expression vectors, comprising and expressing one or more Hendra virus polypeptides, antigens, epitopes or immunogens. In one embodiment, the vector contains and expresses one or more polynucleotides that comprise one or more polynucleotides coding for and/or expressing one or more Hendra virus antigen, polypeptide, epitope or immunogen, in a pharmaceutically or veterinarily acceptable carrier, excipient, adjuvant, or vehicle.

According to another embodiment, the vector or vectors in the composition or vaccine comprise, or consist essentially of, or consist of polynucleotide(s) encoding one or more proteins or fragment(s) of a Hendra virus polypeptide, antigen, epitope or immunogen. In another embodiment, the composition or vaccine comprises one, two, or more vectors comprising polynucleotides encoding and expressing, advantageously in vivo, a Hendra virus polypeptide, antigen, fusion protein or an epitope thereof. The invention is also directed at mixtures of vectors that comprise polynucleotides encoding and expressing different Hendra virus polypeptides, antigens, epitopes, fusion protein, or immunogens, e.g., a Hendra virus F and/or G polypeptide, antigen, epitope or immunogen from pathogens causing disease in different species such as, but not limited to, humans, horses, pigs, cows or cattle, dogs, and cats.

In the present invention a recombinant viral vector is used to express one or more coding sequences or fragments thereof encoding one or more Hendra virus polypeptide or fragment or variant thereof. Specifically, the viral vector can express one or more Hendra virus sequences, more specifically one or more Hendra virus genes or fragments thereof that encode Hendra virus F or G polypeptides. Viral vector contemplated herein includes, but not limited to, poxvirus [e.g., vaccinia virus or attenuated vaccinia virus, avipox virus or attenuated avipox virus (e.g., canarypox, fowlpox, dovepox, pigeonpox, quailpox, ALVAC, TROVAC; see e.g., U.S. Pat. Nos. 5,505,941, 5,494,8070), raccoonpox virus, swinepox virus, etc.], adenovirus (e.g., human adenovirus, canine adenovirus), herpesvirus (e.g. canine herpesvirus, feline herpesvirus, bovine herpesvirus, swine herpesvirus, equine herpesvirus), baculovirus, retrovirus, etc. In another embodiment, the avipox expression vector may be a canarypox vector, such as, ALVAC. In yet another embodiment, the avipox expression vector may be a fowlpox vector, such as, TROVAC. The Hendra virus polypeptide, antigen, epitope or immunogen may be a Hendra virus F or G protein. The one or more polynucleotides encoding Hendra virus F polypeptide, or Hendra virus G polypeptide, or both F and G proteins are inserted under the control of a specific poxvirus promoter, e.g., the vaccinia promoter 7.5 kDa (Cochran et al., 1985), the vaccinia promoter I3L (Riviere et al., 1992), the vaccinia promoter HA (Shida, 1986), the cowpox promoter ATI (Funahashi et al., 1988), the vaccinia promoter H6 (Taylor et al., 1988b; Guo et al., 1989; Perkus et al., 1989), inter alia.

According to a yet further embodiment of the invention, the expression vector is a plasmid vector, in particular an in vivo expression vector. In a specific, non-limiting example, the pVR1020 or 1012 plasmid (VICAL Inc.; Luke et al., 1997; Hartikka et al., 1996, see, e.g., U.S. Pat. Nos. 5,846, 946 and 6,451,769) can be utilized as a vector for the insertion of a polynucleotide sequence. The pVR1020 plasmid is derived from pVR1012 and contains the human tPA signal sequence. In one embodiment the human tPA signal comprises from amino acid M(1) to amino acid S(23) of GenBank accession number HUMTPA14. In another specific, non-limiting example, the plasmid utilized as a vector for the insertion of a polynucleotide sequence can contain the signal peptide sequence of equine IGF1 from amino acid M(24) to amino acid A(48) of GenBank accession number U28070. Additional information on DNA plasmids which may be consulted or employed in the practice are found, for example, in U.S. Pat. Nos. 6,852,705; 6,818,628; 6,586,412; 6,576,243; 6,558,674; 6,464,984; 6,451,770; 6,376,473 and 6,221,362.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

Each plasmid comprises or contains or consists essentially of, in addition to the polynucleotide(s) encoding the Hendra virus polypeptide(s), antigen(s), epitopes or immunogens, optionally fused with a heterologous peptide sequence, variant, analog or fragment, operably linked to a promoter or under the control of a promoter or dependent upon a promoter. In general, it is advantageous to employ a strong promoter functional in eukaryotic cells. The strong promoter may be, but not limited to, the immediate early cytomegalovirus promoter (CMV-IE) of human or murine origin, or optionally having another origin such as the rat or guinea pig.

In more general terms, the promoter has either a viral, or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa et al., 2000), or the actin promoter (Miyazaki et al., 1989).

As to the polyadenylation signal (polyA) for the plasmids and viral vectors other than poxviruses, use can be made of the poly(A) signal of the bovine growth hormone (bGH) gene (see U.S. Pat. No. 5,122,458), or the poly(A) signal of the rabbit β-globin gene or the poly(A) signal of the SV40 virus.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

Methods of Use and Article of Manufacture

The present invention includes the following method embodiments. In an embodiment, a method of vaccinating an animal comprising administering composition comprising a vector comprising one or more polynucleotides encoding one or more Hendra virus polypeptides or fragments or variants thereof and a pharmaceutical or veterinarily acceptable carrier, excipient, vehicle, or adjuvant to an animal and human is disclosed. In one aspect of this embodiment, the animal is an equine, a canine, a feline, or a porcine.

In yet another embodiment, a method of vaccinating an animal comprising a composition comprising one or more vectors comprising one or more polynucleotides encoding one or more Hendra virus polypeptides and optionally a pharmaceutical or veterinarily acceptable carrier, excipient, vehicle, or adjuvant and optionally one or more compositions comprising additional antigens is disclosed.

In one embodiment of the invention, a prime-boost regimen can be employed, which is comprised of at least one primary administration and at least one booster administration using at least one common polypeptide, antigen, epitope or immunogen. The administration may comprise one, two, or more vaccines or compositions comprising same or different antigens. Typically the immunological composition(s) or vaccine(s) used in primary administration is different in nature from those used as a booster. However, it is noted that the same composition(s) can be used as the primary administration and the booster administration. This administration protocol is called "prime-boost".

A prime-boost regimen comprises at least one prime-administration and at least one boost administration using at least one common polypeptide and/or variants or fragments thereof. The prime-administration may comprise one or more administrations. Similarly, the boost administration may comprise one or more administrations. The prime-administration may comprise one or more antigens and the boost administration may comprise one or more antigens.

In one aspect of the prime-boost protocol or regime of the invention, a prime-boost protocol may comprise the administration of a composition comprising a recombinant viral vector that contains and expresses one or more Hendra virus polypeptides, antigens and/or variants or fragments thereof in vivo followed by the administration of one or more recombinant Hendra virus polypeptides or antigens, or an inactivated viral composition or vaccine comprising the Hendra virus polypeptides or antigens, or a DNA plasmid-based composition or vaccine expressing one or more Hendra virus polypeptides or antigens. Likewise, a prime-boost protocol may comprise the administration of a composition comprising one or more recombinant Hendra virus antigens, or an inactivated viral composition or vaccine comprising the Hendra virus polypeptides or antigens, or a DNA plasmid-based composition or vaccine expressing the Hendra virus polypeptide or antigen followed by the administration of a recombinant viral vector that contains and expresses one or more Hendra virus polypeptides or antigens and/or variants or fragments thereof in vivo. It is further noted that both the primary and the secondary administrations may comprise the recombinant viral vector that contains and expresses one or more Hendra virus polypeptides of the invention. Thus, the recombinant Hendra viral vector of the invention may be administered in any order with one or more recombinant Hendra virus antigens, an inactivated viral composition or vaccine comprising the Hendra virus antigens, or a DNA plasmid-based composition or vaccine expressing one or more Hendra virus antigens, or alternatively may be used alone as both the primary and secondary compositions.

The dose volume of compositions for target species that are mammals, e.g., the dose volume of dog compositions, based on viral vectors, e.g., non-poxvirus-viral-vector-based compositions, is generally between about 0.1 to about 2.0 ml, between about 0.1 to about 1.0 ml, and between about 0.5 ml to about 1.0 ml.

The efficacy of the vaccines may be tested about 2 to 4 weeks after the last immunization by challenging animals, such as horses, cats, dogs, pigs, or experimental laboratory animals (such as ferrets and guinea pigs) with a virulent strain of Hendra virus strain. Both homologous and heterologous strains are used for challenge to test the efficacy of the vaccine. The animal may be challenged by spray, intra-nasally, intra-ocularly, intra-tracheally, and/or orally. The challenge viral may be about $10^{5-8}$ $EID_{50}$ in a volume depending upon the route of administration. For example, if the administration is by spray, a virus suspension is aerosolized to generate about 1 to 100 μm droplets, if the administration is intra-nasal, intra-tracheal or oral, the volume of the challenge virus is about 0.5 ml, 1-2 ml, and 5-10 ml, respectively. Animals may be observed daily for 14 days following challenge for clinical signs, for example, dehydration and fever. In addition, the groups of animals may be euthanized and evaluated for pathological findings of pulmonary and pleural hemorrhage, tracheitis, bronchitis, bronchiolitis, bronchopneumonia and internal organs. Orophayngeal swabs may be collected from all animals post challenge for virus isolation. The presence or absence of viral antigens in respiratory tissues may be evaluated by quantitative real time reverse transcriptase polymerase chain reaction (qRT-PCR). Blood samples may be collected before and post-challenge and may be analyzed for the presence of Hendra virus-specific antibody.

The various administrations are preferably carried out 1 to 6 weeks apart. Preferred time interval is 3 to 5 weeks, and optimally 4 weeks. According to one embodiment, a six-month booster interval or an annual booster interval is also envisioned. The animals, for examples horses, may be at least four months of age at the time of the first administration.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

The present invention contemplates at least one administration to an animal of an efficient amount of the therapeutic composition made according to the invention. The animal may be male, female, pregnant female and newborn. This administration may be via various routes including, but not limited to, intramuscular (IM), intradermal (ID) or subcutaneous (SC) injection or via intranasal or oral administration. The therapeutic composition according to the invention can also be administered by a needleless apparatus (as, for example with a Pigjet, Dermojet, Biojector, Avijet (Merial, Ga., USA), Vetj et or Vitajet apparatus (Bioject, Oregon, USA)). Another approach to administering plasmid compositions is to use electroporation (see, e.g. Tollefsen et al., 2002; Tollefsen et al., 2003; Babiuk et al., 2002; PCT Application No. WO99/01158). In another embodiment, the therapeutic composition is delivered to the animal by gene gun or gold particle bombardment.

The recombinant composition or vaccine can be administered to an animal or infected or transfected into cells in an amount of about 1.0 log 10 TCID50 (or CCID50) to about 20.0 log 10 TCID50 (or CCID50), about 1.0 log 10 TCID50 (or CCID50) to about 15.0 log 10 TCID50 (or CCID50), about 2.0 log 10 TCID50 (or CCID50) to about 10.0 log 10 TCID50 (or CCID50), or about 4.0 log 10 TCID50 (or CCID50) to about 8.0 log 10 TCID50 (or CCID50).

In one embodiment, the invention provides for the administration of a therapeutically effective amount of a formulation for the delivery and expression of a Hendra virus antigen or epitope in a target cell. Determination of the therapeutically effective amount is routine experimentation for one of ordinary skill in the art. In one embodiment, the formulation comprises an expression vector comprising a polynucleotide that expresses one or more Hendra virus antigens or epitopes and a pharmaceutically or veterinarily acceptable carrier, vehicle, adjuvant, or excipient.

The pharmaceutically or veterinarily acceptable carriers or vehicles or excipients or adjuvants are well known to the one skilled in the art. For example, a pharmaceutically or veterinarily acceptable carrier or vehicle or excipient or adjuvant can be a 0.9% NaCl (e.g., saline) solution or a phosphate buffer. Other pharmaceutically or veterinarily acceptable carrier or vehicle or excipient or adjuvant that can be used for methods of this invention include, but are not limited to, poly-(L-glutamate) or polyvinylpyrrolidone. The pharmaceutically or veterinarily acceptable carrier or vehicle or excipient or adjuvant may be any compound or combination of compounds facilitating the administration of the vector (or protein expressed from an inventive vector in vitro) and the transfection or infection and/or improves preservation of the vector or protein in a host. Doses and dose volumes are herein discussed in the general description and can also be determined by the skilled artisan from this disclosure read in conjunction with the knowledge in the art, without any undue experimentation.

The cationic lipids containing a quaternary ammonium salt which are advantageously but not exclusively suitable for plasmids, are those having the following formula:

$$R_1-O-CH_2-CH-CH_2-\overset{\overset{CH_3}{|}^+}{\underset{\underset{CH_3}{|}}{N}}-R_2-X$$
$$\phantom{R_1-O-CH_2-C}\underset{OR_1}{|}$$

in which R1 is a saturated or unsaturated straight-chain aliphatic radical having 12 to 18 carbon atoms, R2 is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr, 1994), to form DMRIE-DOPE.

When DOPE is present, the DMRIE:DOPE molar ratio is advantageously about 95:about 5 to about 5:about 95, more advantageously about 1:about 1, e.g., 1:1.

In another embodiment, pharmaceutically or veterinarily acceptable carrier, excipient, vehicle or adjuvant may be a water-in-oil emulsion. Examples of suitable water-in-oil emulsions include oil-based water-in-oil vaccinal emulsions which are stable and fluid at 4° C. containing: from 6 to 50 v/v % of an antigen-containing aqueous phase, preferably from 12 to 25 v/v %, from 50 to 94 v/v % of an oil phase containing in total or in part a non-metabolizable oil (e.g., mineral oil such as paraffin oil) and/or metabolizable oil (e.g., vegetable oil, or fatty acid, polyol or alcohol esters), from 0.2 to 20 p/v % of surfactants, preferably from 3 to 8 p/v %, the latter being in total or in part, or in a mixture either polyglycerol esters, said polyglycerol esters being preferably polyglycerol (poly)ricinoleates, or polyoxyethylene ricin oils or else hydrogenated polyoxyethylene ricin oils. Examples of surfactants that may be used in a water-in-oil emulsion include ethoxylated sorbitan esters (e.g., polyoxyethylene (20) sorbitan monooleate (TWEEN 80®), available from AppliChem, Inc., Cheshire, Conn.) and sorbitan esters (e.g., sorbitan monooleate (SPAN 80®), available from Sigma Aldrich, St. Louis, Mo.). In addition, with respect to a water-in-oil emulsion, see also U.S. Pat. No. 6,919,084. In some embodiments, the antigen-containing aqueous phase comprises a saline solution comprising one or more buffering agents. An example of a suitable buffering solution is phosphate buffered saline. In one embodiment, the water-in-oil emulsion may be a water/oil/water (W/O/W) triple emulsion (U.S. Pat. No. 6,358,500). Examples of other suitable emulsions are described in U.S. Pat. No. 7,371,395.

The immunological compositions and vaccines according to the invention may comprise or consist essentially of one or more pharmaceutically or veterinarily acceptable carriers, excipients, vehicles or adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on page 147 of "Vaccine Design, The Subunit and Adjuvant Approach" published by M. Powell, M. Newman, Plenum Press 1995, and the emulsion MF59 described on page 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The oil in water emulsion (3), which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters.

The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121.

Among the type (1) adjuvant polymers, preference is given to polymers of crosslinked acrylic or methacrylic acid, especially crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are crosslinked by allyl saccharose or by allyl pentaerythritol. Among them, reference is made to Carbopol 974P, 934P and 971P.

As to the maleic anhydride-alkenyl derivative copolymers, preference is given to EMA (Monsanto), which are straight-chain or crosslinked ethylene-maleic anhydride copolymers and they are, for example, crosslinked by divinyl ether.

With regard to structure, the acrylic or methacrylic acid polymers and EMA are preferably formed by basic units having the following formula:

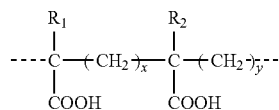

in which:
R1 and R2, which can be the same or different, represent H or CH3
x=0 or 1, preferably x=1
y=1 or 2, with x+y=2.
For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final immunological or vaccine composition can range between about 0.01 to about 1.5% w/v, about 0.05 to about 1% w/v, and about 0.1 to about 0.4% w/v.

The cytokine or cytokines (5) can be in protein form in the immunological or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector thereof.

The invention comprehends preparing such combination compositions; for instance by admixing the active components, advantageously together and with an adjuvant, carrier, cytokine, and/or diluent.

Cytokines that may be used in the present invention include, but are not limited to, granulocyte colony stimulating factor (G-CSF), granulocyte/macrophage colony stimulating factor (GM-CSF), interferon α (IFNα), interferon β (IFNβ), interferon γ, (IFNγ), interleukin-1α (IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNFα), tumor necrosis factor β (TNFβ), OX40L, and transforming growth factor β (TGFβ). It is understood that cytokines can be co-administered and/or sequentially administered with the immunological or vaccine composition of the present invention. Thus, for instance, the vaccine of the instant invention can also contain an exogenous nucleic acid molecule that expresses in vivo a suitable cytokine, e.g., a cytokine matched to this host to be vaccinated or in which an immunological response is to be elicited (for instance, a canine cytokine for preparations to be administered to canine).

The invention will now be further described by way of the following non-limiting examples.

EXAMPLES

Without further elaboration, it is believed that one skilled in the art can, using the preceding descriptions, practice the present invention to its fullest extent. The following detailed examples are to be construed as merely illustrative, and not limitations of the preceding disclosure in any way whatsoever. Those skilled in the art will promptly recognize appropriate variations from the procedures both as to reactants and as to reaction conditions and techniques.

Construction of DNA inserts, plasmids and recombinant viral or plant vectors was carried out using the standard molecular biology techniques described by J. Sambrook et al. (Molecular Cloning: A Laboratory Manual, 2nd Edition, Cold Spring Harbor Laboratory, Cold Spring Harbor, N.Y., 1989).

Example 1 Construction of Plasmid Containing Hendra Virus G Gene-pC5 H6p, Plasmid p362-Hendra G The synthetic Hendra virus G polypeptide (SEQ ID NO:2) optimized for expression in Equus caballus was cloned into pUC57 (GenScript Corporation, New Jersey, USA) vector. The EcoRV/KpnI fragment containing Hendra virus G fragment from the pUC57 vector was cloned into pCXL-148-2 (Merial Limited proprietary material) containing vaccinia H6 promoter resulting in plasmid p362-Hendra G (see FIG. 2 plasmid map).

Example 2 Construction of Plasmid Containing Hendra Virus F Gene-pC5 H6p, Plasmid p362-Hendra F The synthetic Hendra virus F polynucleotide (SEQ ID NO:5) optimized for expression in Equus caballus was cloned into pUC57 vector. The EcoRV/KpnI fragment containing Hendra virus F fragment from the pUC57 vector was cloned into pCXL-148-2 (Merial Limited proprietary material) containing vaccinia H6 promoter resulting in plasmid p362-Hendra F (see FIG. 2 plasmid map).

Example 3 Generation and Characterization of ALVAC Recombinant Containing Hendra Virus G Gene in C5 Loci of ALVAC (vCP3004)

A. Generation of vCP3004

The IVR (in vitro recombinant) was performed by transfection of Primary chicken embryo fibroblast (1°CEF) cells with NotI linearized donor plasmid p362-Hendra G. The transfected cells were subsequently infected with parental ALVAC as rescue virus at MOI (multiplicity of infection) of 10. After 24 hours, the transfected/infected cells were harvested, sonicated and used for recombinant virus screening. Recombinant plaques were screened based on the plaque lift hybridization method using Hendra G-specific probe which was labeled with horse radish peroxidase according to the manufacturer's protocol (GE Healthcare, Cat# RPN3001). After four sequential rounds of plaque purification, the recombinants designated as vCP3004.1.1.1.1. and vCP3004.5.3.2.2 were generated and confirmed by hybridization as 100% positive for the Hendra G insert and 100% negative for the C5 ORF.

B. Genomic Analysis

Genomic DNA from vCP3004.1.1.1.1 was extracted and digested with BamHI, HindIII and PstI, separated by agarose electrophoresis and then transferred to nylon membrane. Southern blot was performed by probing with a Hendra G probe. The primers used to generate the Hendra G probe are:

```
                                         (SEQ ID NO: 13)
HenG.1F GGCTCTGACCGACAAAATCG (SEQ ID NO: 14)
HenG.1R GAACTGCAGGATGATGTCCC
```

Specific 704 bp and 903 bp of BamHI digest bands, 12293 bp of HindIII digest band, 614 bp, 309 bp, and 94 bp of PstI digest bands were observed at the expected sizes, indicating the correct insertion of Hendra G into the C5 locus (see FIG. 3).

C. Expression Analysis

Figure 4:
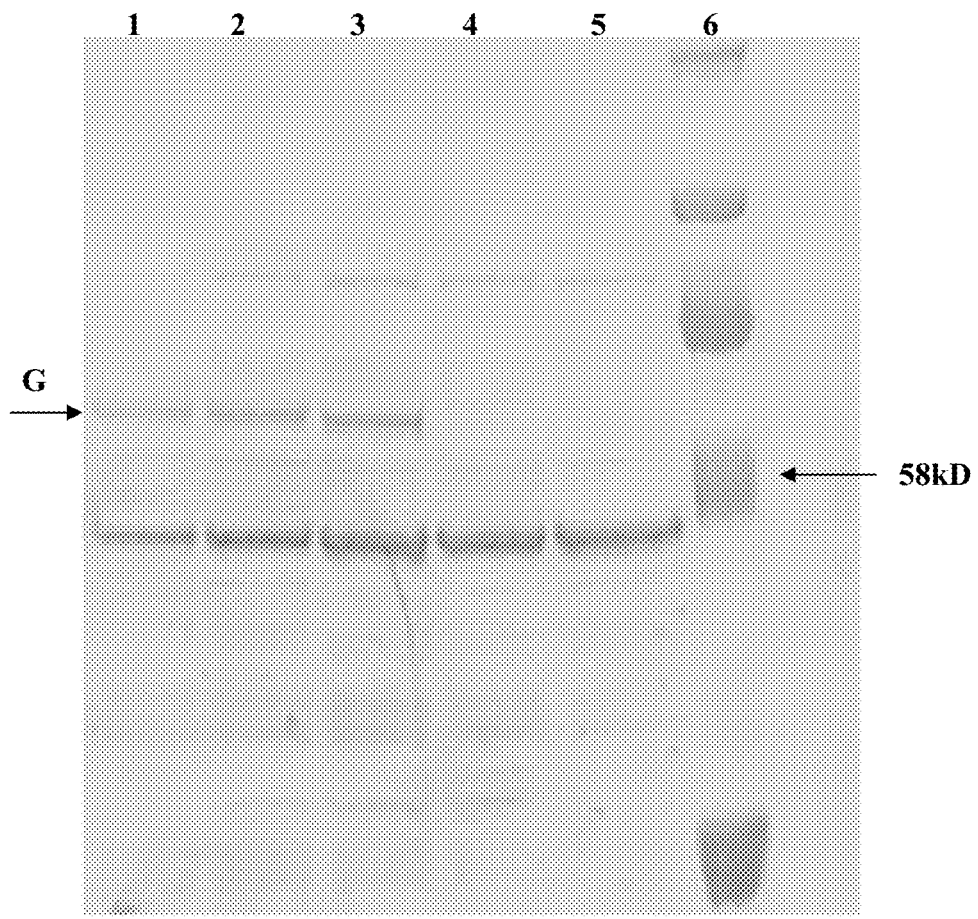
FIG. 4 shows the vCP3004 (Hendra G) Western Blot result.
Figure 5:
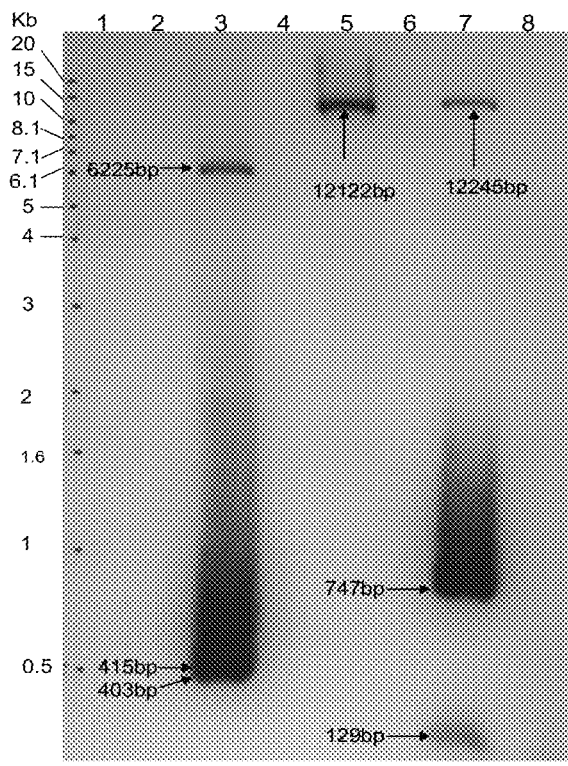
FIG. 5 shows the vCP3005 (Hendra F) Southern Blot result.
Figure 8A:
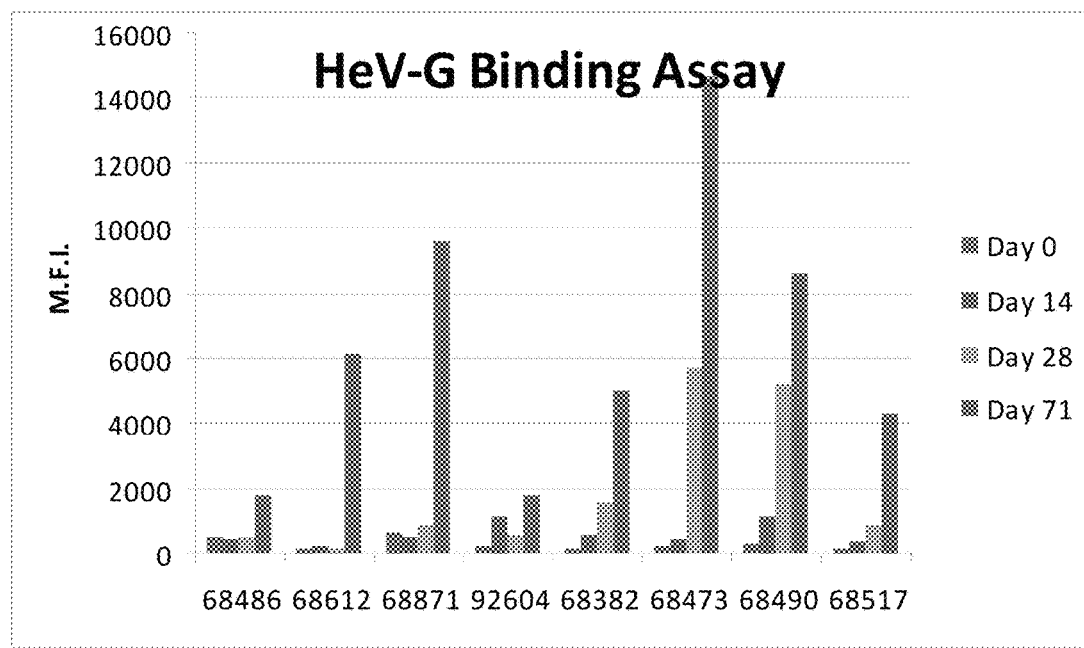
Figure 8B:
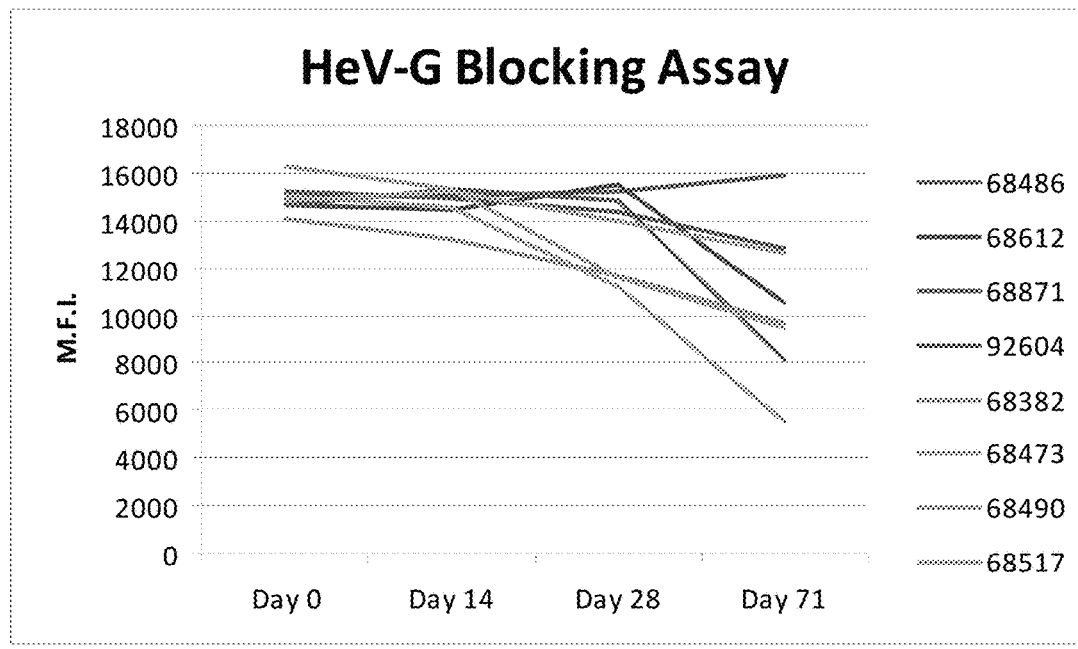

Primary CEF cells were infected with vCP3004.1.1.1.1 at MOI of 10 and incubated at 37° C. for 24 hours. The cells and culture supernatant were then harvested. Sample proteins were separated on a 10% SDS-PAGE gel, transferred to PVDF membrane. A serum raised in guinea pig reacted strongly with the G protein at an apparent molecular size of approximately 70 kDa. The result is shown in FIG. 4.

D. Sequence Analysis

A more detailed analysis of the P3 stock genomic DNA was performed by PCR amplification and sequence analysis of the flanking arms of the C5 locus and the Hendra G insert. Primers C5R.1F and C5L.2R located at the end of the arms of the C5 locus in the donor plasmid were used to amplify the entire C5R-Hendra G insert-C5L fragment.

```
                                         (SEQ ID NO: 15)
C5R.1F ATTCTATCGGAAGATAGGATACCAG (SEQ ID NO: 16)
C5L.2R GGAGATACCTTTAGATATGGATCTG
```

The results showed that the sequences of the Hendra G insert and the C5 left and right arms around the G insert in vCP3004.1.1.1.1 were correct.

Example 4 Generation and Characterization of ALVAC Recombinant Containing Hendra Virus F Gene in C5 Loci of ALVAC (vCP3005)

A. Generation of vCP3005

The IVR (in vitro recombinant) was performed by transfection of Primary chicken embryo fibroblast (1°CEF) cells with NotI linearized donor plasmid p362-Hendra F. The transfected cells were subsequently infected with parental ALVAC as rescue virus at MOT (multiplicity of infection) of 10. After 24 hours, the transfected/infected cells were harvested, sonicated and used for recombinant virus screening. Recombinant plaques were screened based on the plaque lift hybridization method using Hendra F-specific probe which was labelled with horse radish peroxidase according to the manufacturer's protocol (GE Healthcare, Cat# RPN3001). After four sequential rounds of plaque purification, the recombinants designated as vCP3005.3.4.1 and vCP3005.5.3.2 were generated and confirmed by hybridization as 100% positive for the Hendra F insert and 100% negative for the C5 ORF.

B. Genomic Analysis

Genomic DNA from vCP3005.3.4.1 was extracted and digested with BamHI, HindIII and PstI, separated by agarose electrophoresis and then transferred to nylon membrane. Southern blot was performed by probing with a Hendra F probe. The primers used to generate the Hendra F probe are:

```
                                    (SEQ ID NO: 17)
HenF.1F CCATCGAACTGTATAACAAT (SEQ ID NO: 18)
HenF.1R GGAGATGATGATGTTGCCCA
```

Specific 704 bp and 903 bp of BamHI digest bands, 12293 bp of HindII band, 614 bp, 309 bp and 94 bp of PstI digest bands were observed at the expected sizes, indicating the correct insertion of Hendra F into the C5 locus (see FIG. 5).

C. Expression Analysis

Primary CEF cells were infected with vCP3005.3.4.1 at MOT of 10 and incubated at 37° C. for 24 hours. The cells and culture supernatant were then harvested. Sample proteins were separated on a 10% SDS-PAGE gel, transferred to PVDF membrane. When a serum raised in guinea pig was used in the Western blot, a faint band corresponding to uncleaved F0 protein at approximately 60 kDa was recognized. The result is shown in FIG. 6.

D. Sequence Analysis

A more detailed analysis of the P3 stock genomic DNA was performed by PCR amplification and sequence analysis of the flanking arms of the C5 locus and the Hendra F insert. Primers C5R.1F (SEQ ID NO:15) and C5L.2R (SEQ ID NO:16) located at the end of the arms of the C5 locus in the donor plasmid were used to amplify the entire C5R-Hendra F inset-C5L fragment.

Example 5 Fusion Assay

Simultaneous co-infection of HEK293 cells with the ALVAC-Hendra G (vCP3004) and ALVAC-Hendra F (vCP3005) at an MOI of 10+10 resulted in syncytium formation, while single infections either ALVAC-Hendra F (vCP3005) or ALVAC-Hendra G (vCP3004) recombinant virus at MOI of 20 did not result in syncytium formation, demonstrating the functionality of both proteins (see FIG. 7).

Example 6 Serology Study of Horses Vaccinated with ALVAC-Hendra F or G and ALVAC-Nipah F or G The Canarypox vectors (ALVAC) containing polynucleotides (SEQ ID NO:19 and 21) encoding Nipah F protein (SEQ ID NO:20) and Nipah G protein (SEQ ID NO:22) were constructed as described in US patent application US 2007/0031455.

In this study, two groups of horses were vaccinated IM with the mixture of vCP-Hendra G vector (vCP3004) and vCP-Nipah F vector (ALVAC vector containing Nipah F) on D0 and D28. Group 1 received the vector mixture in Carbomer at 5.8 log 10 TCID50/dose. Group 2 received the vector mixture in Carbomer at 6.8 log 10 TCID50/dose. Sera were titrated for antibodies against Hendra G and F proteins and Nipah G and F proteins in serum neutralization titre (SNT) test. Sera were also tested in ELISA blocking and binding assays using antibodies against Hendra G protein and Nipah G protein respectively.

FIGS. 8A-C show the ELISA binding assay and blocking assay using antibodies against Hendra G protein, and SNT test against Hendra G and F proteins. FIGS. 9A-C show the binding assay and blocking assay using antibodies against Nipah G protein, and SNT test against Nipah G and F proteins.

The results showed that vaccination of horses with vCP-Hendra G vector and vCP-Nipah F vector induced anti-Hendra and anti-Nipah responses even as late as D70.

Example 8 Clinical and Serology Study of Vaccinated Horses and Canaries

Vaccinations of horses and canaries using vCP3004 (ALVAC-Hendra G)+vCP3005 (ALVAC-Hendra F), vCP3004 (ALVAC-Hendra G) alone and vCP3005 (ALVAC-Hendra F) alone were done on Day 0, Day 28 and D183. Blood, urine, nasal/oral/rectal and ocular swabs were collected and tested for spread/shed evaluation. The vCP3004 (ALVAC-Hendra G)+vCP3005 (ALVAC-Hendra F) experiment design is shown in Table 1 below.

TABLE 1 vCP3004 (ALVAC-Hendra G) + vCP3005 (ALVAC-Hendra F) vaccination and clinical test in horses

| Group | Vaccine | Target antigen titre (after dilution) | vaccination | Serum collection | Clinical exam | Biodiffusibility sampling |
|---|---|---|---|---|---|---|
| 1 (n = 4) 2 (n = 4) | Recombinant canary pox expressing Hendra F (vCP3005) and G (vCP3004) in Carbopol | $5.5\log_{10}CCID_{50}$/ dose $6.9\log_{10}CCID_{50}$/ dose | D0, D28 and D183 1 ml IM route | D0, D14, D28, D71, D85, D99, D127, D155, D183, D197, D204, D211 | D0, D0 + 4/6 h, D1 to D3, D28, D28 + 4/6 h, D29 to D31 | Not performed D0, D0 + 4/6 h, D1, D2, D3, D7, D14 |

The clinical result showed that vaccinations are safe for both groups. There is no difference between groups 1 and 2. Biodiffusibility data showed that no virus was detected in any samples.

Figure 10A:
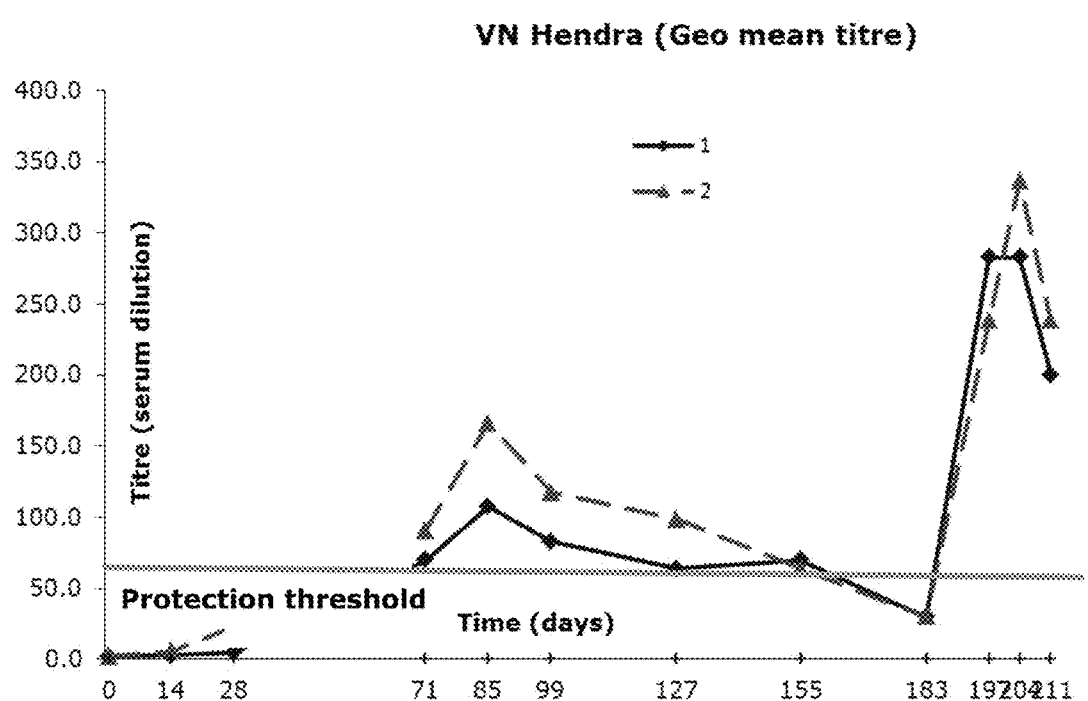
FIG. 10A-10B show the VN serology data of horses vaccinated with vCP3004+vCP3005 against Hendra and Nipah.

FIG. 10A shows the virus neutralization (VN) test against Hendra. Both groups showed above the theoretical protection threshold (64 titre) from D70 onward up to D155. After the third injection on D183, both groups showed clear booster effect.

Figure 10B:
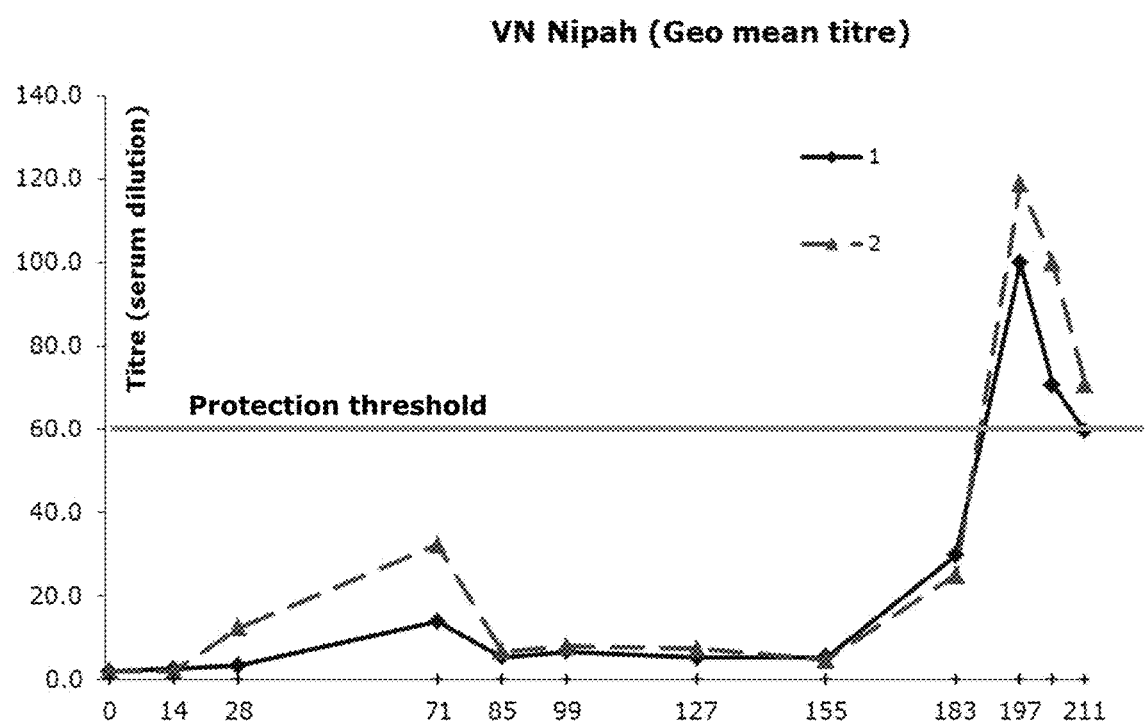

FIG. 10B shows the VN test against Nipah. The results showed good cross reactivity against Nipah. Most horses showed above the protection threshold (60 titre) after the third injection on D183, and some horses showed some protection even after the second injection on D28.

The vCP3004 (ALVAC-Hendra G) experiment design is shown in Table 2 below.

TABLE 2 vCP3004 (ALVAC-Hendra G) vaccination and clinical test in canaries

| | Group | Inoculation on D0 by transcutaneous route | Clinical exam | Euthanasia and Sampling* |
|---|---|---|---|---|
| A | A1 (n = 16) | vCP3004 50 μl (7.0log$_{10}$CCID$_{50}$/dose) | D0, D0 + 3 h/5 h, D1, D3, D6, D8, D10, D13, D15, D16 | 8 birds on D8 8 birds on D16 |
| | A2 (n = 4) | PBS + 50% glycerin (inoculated with placebo and remained in contact with canaries in A1) | | D16 |
| B | B1 (n = 16) | CPpp** 50 μl (7.0log$_{10}$CCID$_{50}$/dose) | | 8 birds on D8 8 birds on D16 |
| | B2 (n = 4) | PBS + 50% glycerin (inoculated with placebo and remained in contact with canaries in B1) | | D16 |

*Sampling: skin at the injection site for histology and virus isolation brain, lung, spleen, liver, kidney pooled for virus isolation
**CPpp: inactivated canarypox virus as a control.

No clinical signs were reported in any one of the four groups. There is no difference in histology between the vaccinated groups.

On D8, virus was detected on the skin of all canaries vaccinated with CPpp (ranging from 2.79 to 6.65 log$_{10}$ CCID$_{50}$/ml) and all but one canaries vaccinated with vCP3004 (ranging from 3.22 to 6.80 log$_{10}$ CCID$_{50}$/ml). On D16, no virus was detected in any vaccinated groups.

Sampling of the pool of organs showed that no virus was detected in any canaries in the two inoculated groups and the two contact groups on D8 and D16.

The results demonstrated the safety and the absence of spreading of vCP3004 administered at high titre by transcutaneous route to the canary. The absence of reactions and virus isolation in the sentinel canaries confirmed the absence of spread of vCP3004 in this species.

The vCP3005 (ALVAC-Hendra F) experiment design is shown in Table 3 below.

TABLE 3 vCP3005 (ALVAC-Hendra F) vaccination and clinical test design in canaries

| | Group | Inoculation on D0 by transcutaneous route | Clinical exam | Euthanasia and Sampling |
|---|---|---|---|---|
| A | A1 (n = 16) | vCP3005 50 μl (7.0log$_{10}$CCID$_{50}$/dose) | D0, D0 + 3 h/5 h, D1, D3, D6, D8, D10, D13, D15, D16 | 8 birds on D8 8 birds on D16 |
| | A2 (n = 4) | PBS + 50% glycerin (inoculated with placebo and remained in contact with canaries in A1) | | D16 |
| B | B1 (n = 16) | CPpp 50 μl (7.0log$_{10}$CCID$_{50}$/dose) | | 8 birds on D8 8 birds on D16 |
| | B2 (n = 4) | PBS + 50% glycerin (inoculated with placebo and remained in contact with canaries in B1) | | D16 |

The result showed that there was no clinical sign for any vaccinated group. On D8 and D16, after the first passage, no virus could be isolated from the organ samples in both inoculated groups and contact animals. This study demonstrated the safety and the absence of spreading of vCP3005 administered at high titre by transcutaneous route to the canary. The absence of reactions and virus isolation in the sentinel canaries confirmed the absence of spread of vCP3005 in this species.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

All documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

What is claimed is:

1. A method of vaccinating an animal to provide direct protection against Hendra virus and cross-protection against Nipah virus, comprising:
   administering to the animal a vaccine composition comprising (i) a first ALVAC vector encoding a Hendra virus G polypeptide having SEQ ID NO:3 and a second ALVAC vector encoding a Hendra virus F polypeptide having SEQ ID NO:6; or (ii) a single ALVAC vector encoding the Hendra virus G polypeptide and the Hendra virus F polypeptide, wherein the vaccine composition is administered to the animal at a dose of at least 5.5 $\log_{10}$ TCID$_{50}$.

2. The method of claim 1, wherein the vaccine composition further comprises an additional antigen.

3. The method of claim 2, wherein the additional antigen is a Nipah antigen.

4. The method of claim 1, wherein the Hendra virus G polypeptide is encoded by a polynucleotide having SEQ ID NO:1 or 2, and wherein the Hendra virus F polypeptide is encoded by a polynucleotide having SEQ ID NO: 4 or 5.

5. The method of claim 1, wherein the vaccine composition further comprises a pharmaceutically or veterinarily acceptable vehicle, adjuvant, diluent, or excipient.

6. The method of claim 1, wherein the method comprises a prime-boost administration protocol.

7. The method of claim 1, wherein the animal is a horse.

8. The method of claim 7, wherein the vaccine composition is administered to the horse at a dose of at least 5.5 $\log_{10}$ TCID$_{50}$.

9. The method of claim 1, wherein the vaccine composition comprises the first ALVAC vector and the second ALVAC vector.

10. The method of claim 1, wherein the vaccine composition comprises the single ALVAC vector.

11. The method of claim 1, wherein the vaccine composition is administered by intramuscular route.

* * * * *